(12) United States Patent
Langhammer et al.

(10) Patent No.: US 8,615,311 B2
(45) Date of Patent: Dec. 24, 2013

(54) MICROELECTORODE ARRAY, METHODS FOR PREPARING THE SAME AND USES THEREOF

(75) Inventors: Christopher Langhammer, Piscataway, NJ (US); Bonnie L. Firestein-Miller, Hillsborough, NJ (US); Jeffrey Zahn, Princeton, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 183 days.

(21) Appl. No.: 13/048,756

(22) Filed: Mar. 15, 2011

(65) Prior Publication Data
US 2012/0004716 A1    Jan. 5, 2012

Related U.S. Application Data

(60) Provisional application No. 61/313,828, filed on Mar. 15, 2010.

(51) Int. Cl.
*A61N 1/04*    (2006.01)

(52) U.S. Cl.
USPC ............ 607/148; 435/375; 435/325; 435/377

(58) Field of Classification Search
USPC ........................................................ 607/148
See application file for complete search history.

(56) References Cited

U.S. PATENT DOCUMENTS

8,318,488 B1 * 11/2012 Bohlen et al. ................. 435/375
2011/0076734 A1 * 3/2011 Zhou et al. ................. 435/173.1

* cited by examiner

*Primary Examiner* — Carl H Layno
*Assistant Examiner* — Jon Eric C Morales
(74) *Attorney, Agent, or Firm* — Fox Rothschild LLP; Gerard P. Norton; Carol E. Thorstad-Forsyth

(57) ABSTRACT

A microelectrode array having a substrate with a plurality of grooves and a plurality of electrical contact pads, the grooves each with at least one electrode electrically connected to at least one of the electrical contact pads, each of the grooves containing at least one myotube that overlays the at least one electrode.

9 Claims, 48 Drawing Sheets
(46 of 48 Drawing Sheet(s) Filed in Color)

FIGS. 2A-C
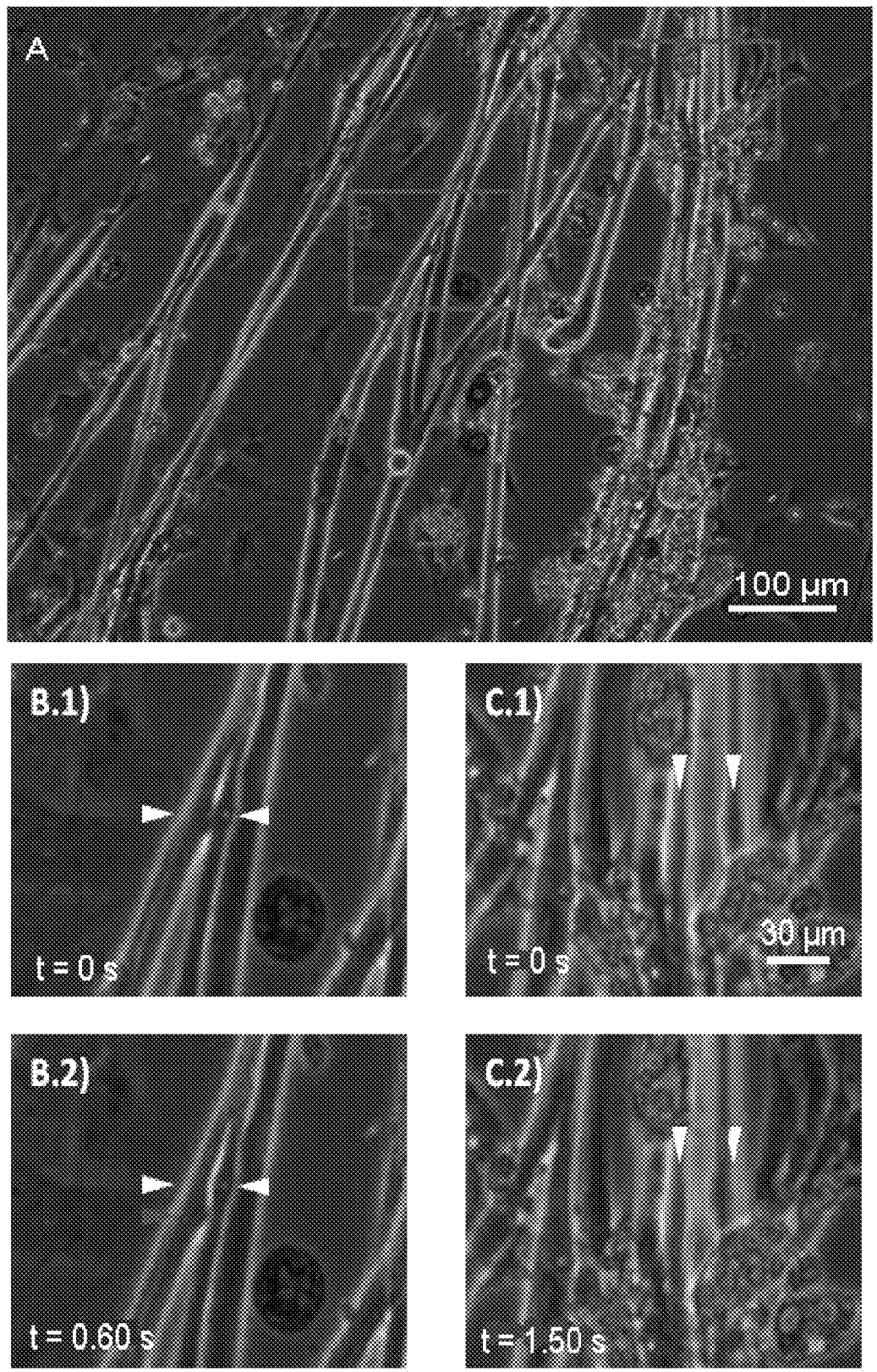

FIGS. 2D-F
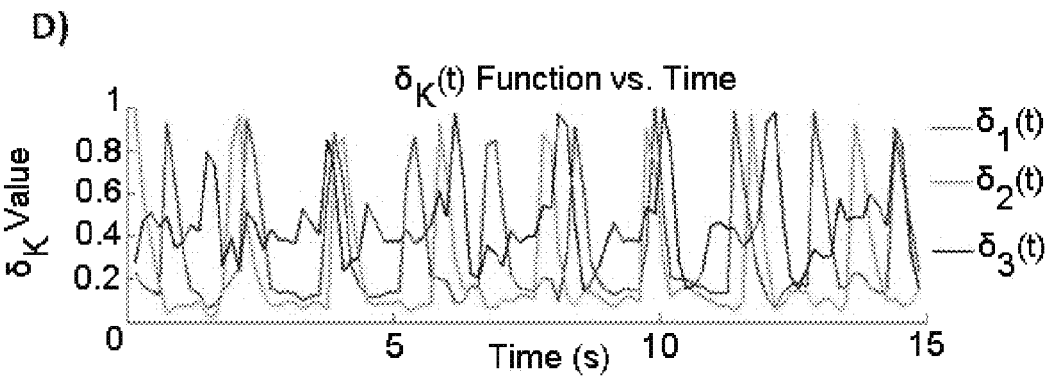
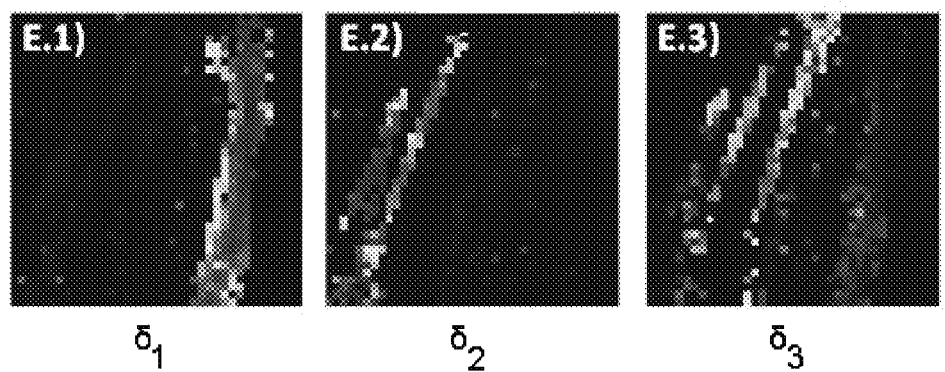
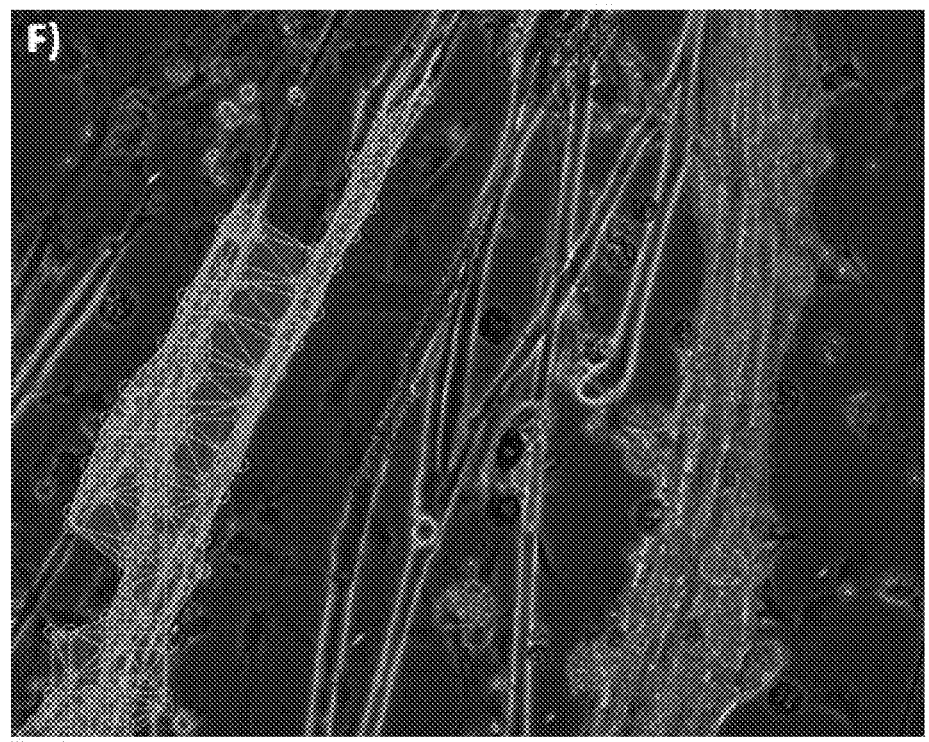

FIGS. 3A-B
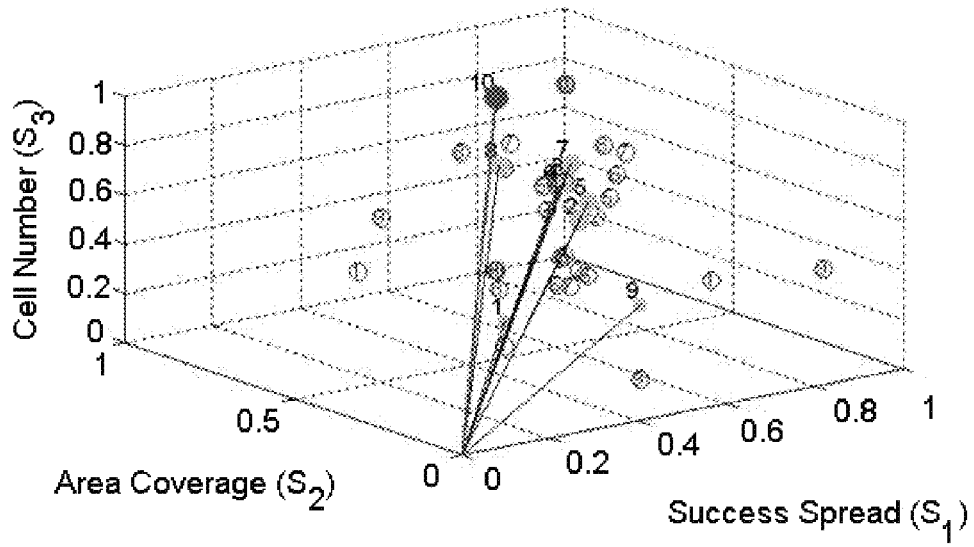
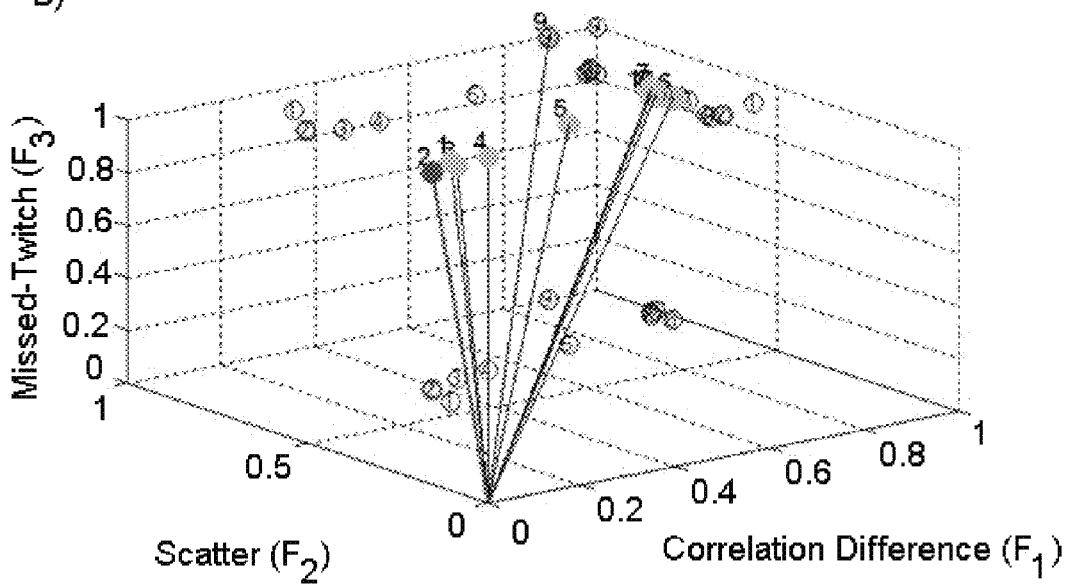

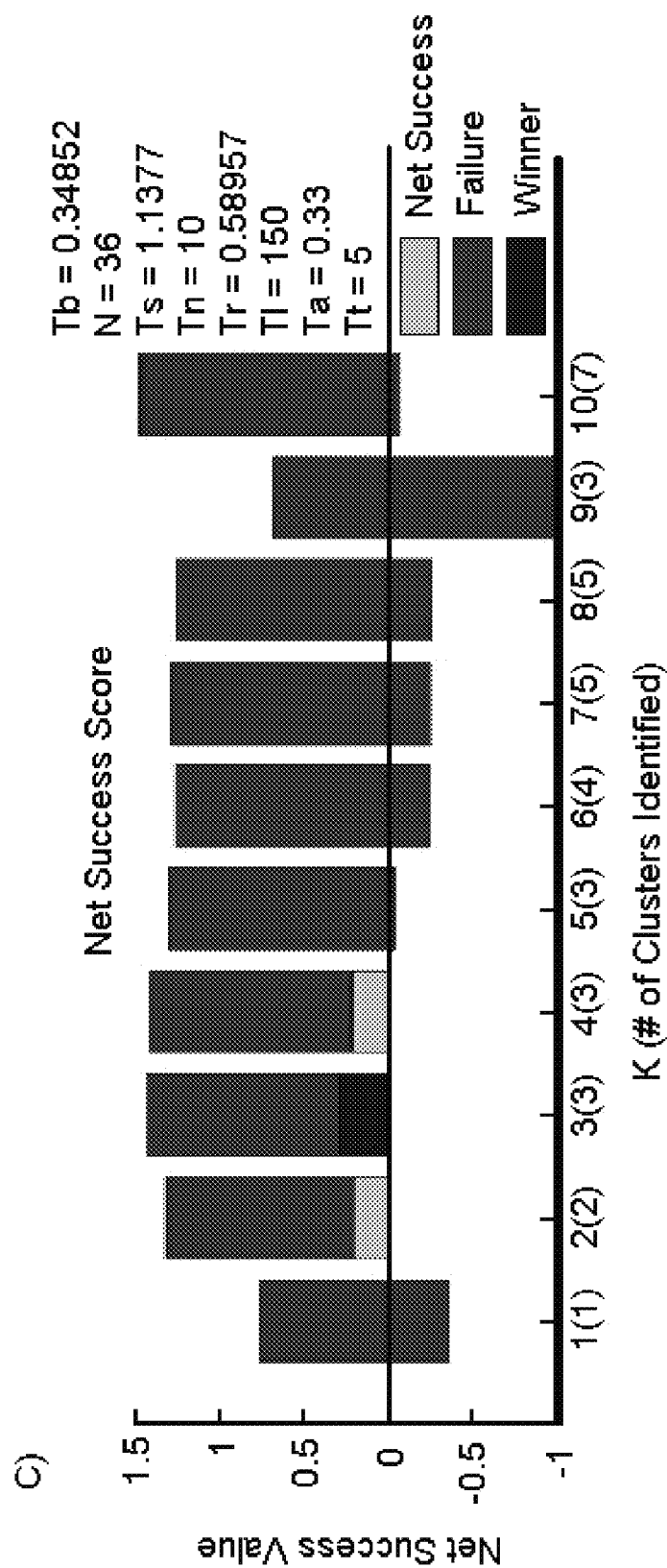
FIG 3.C

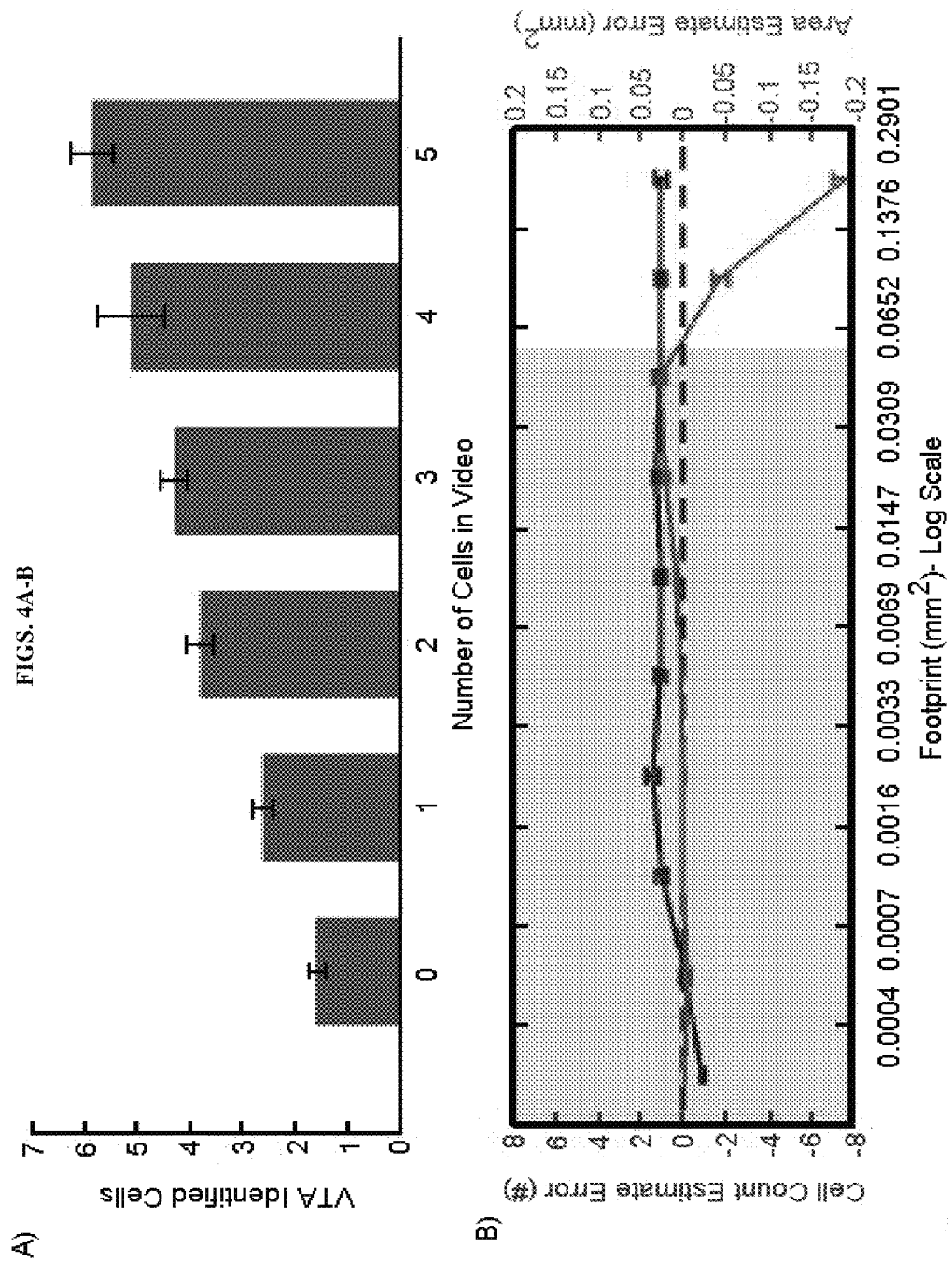
FIGS. 4A-B

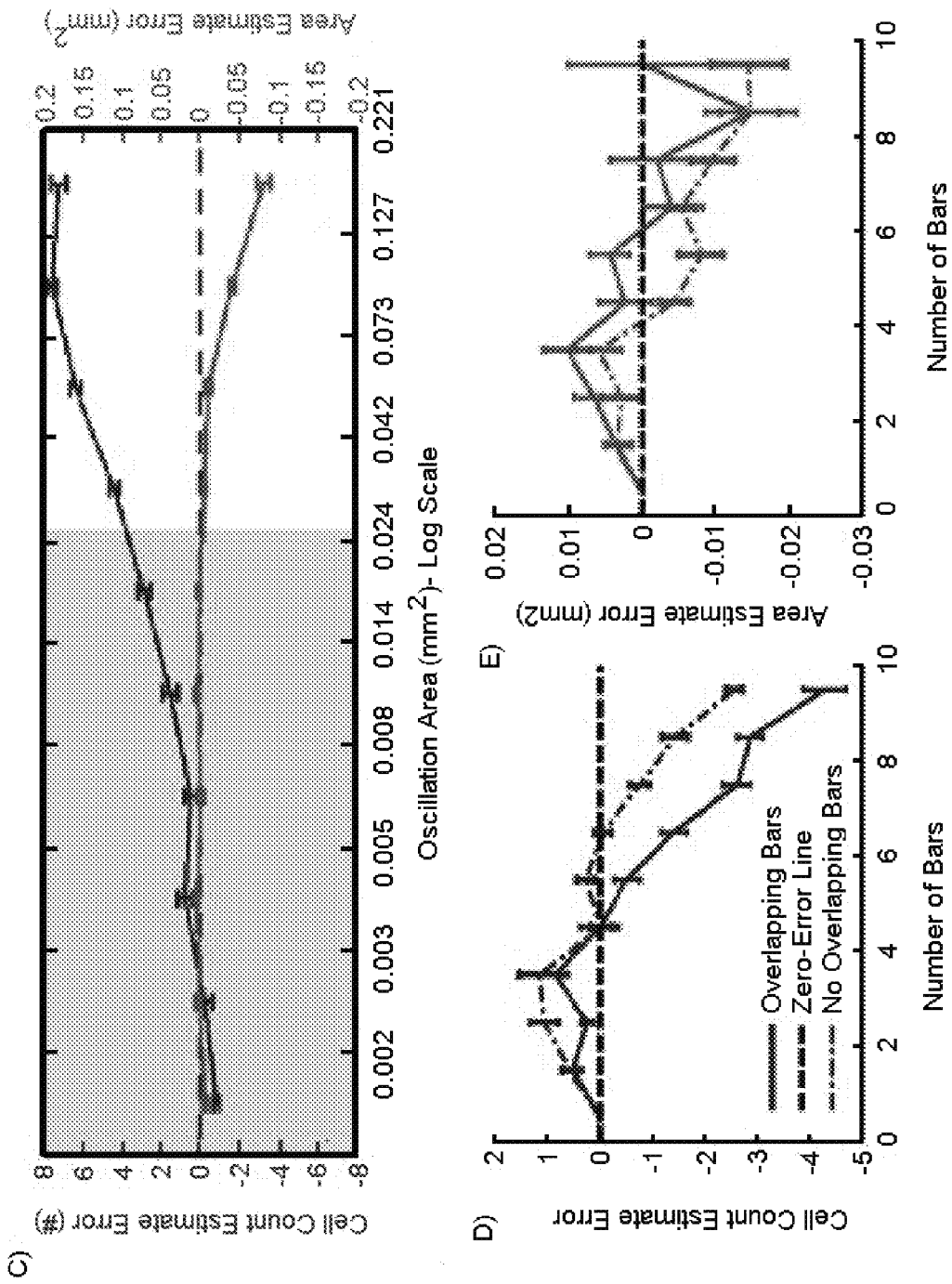
FIGS. 4C-E

FIGS. 5A-D
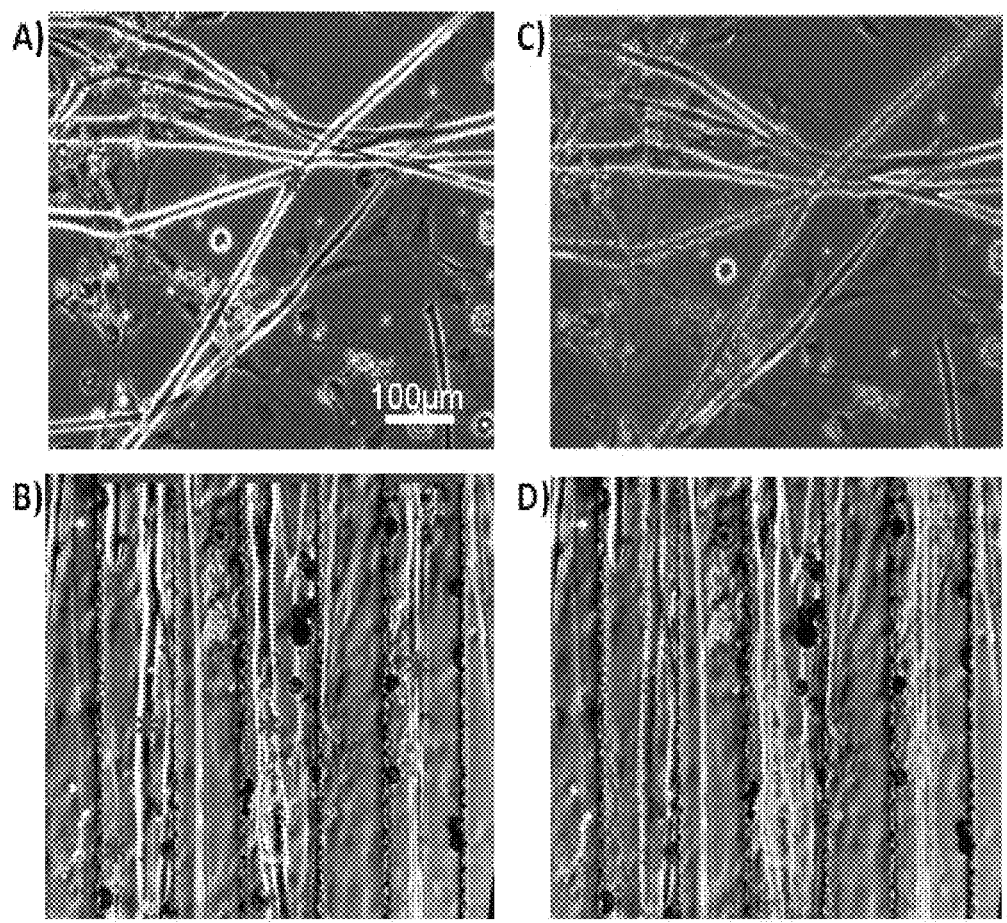

FIGS. 5E-I
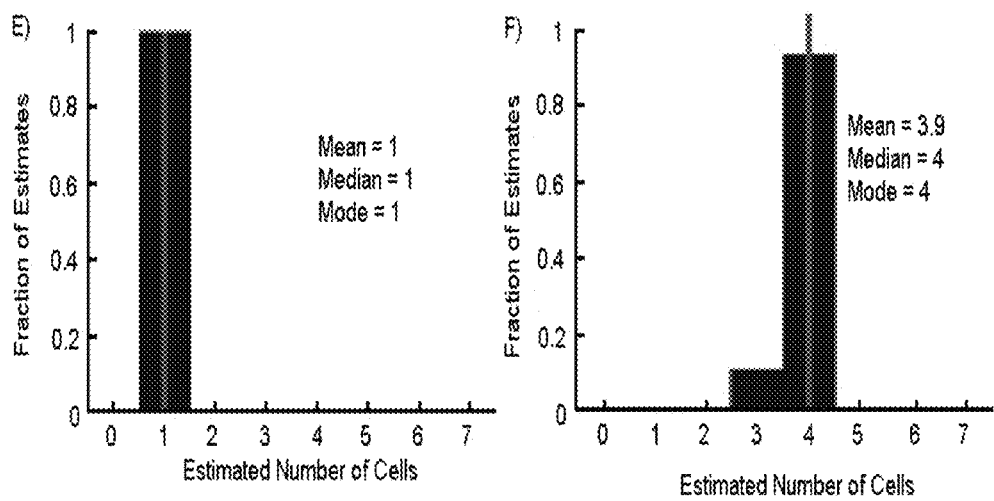
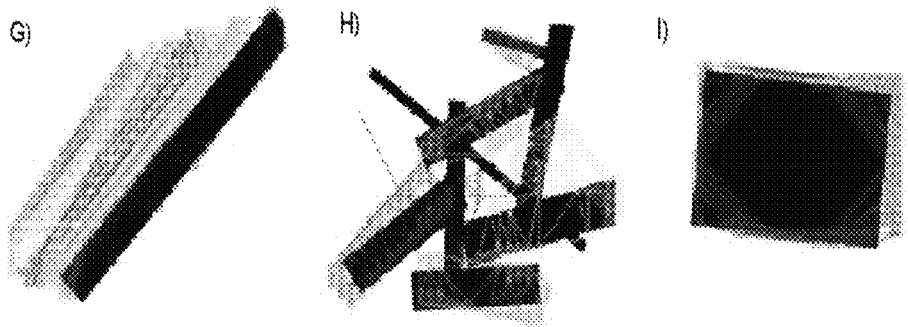

FIGS. 8A-C
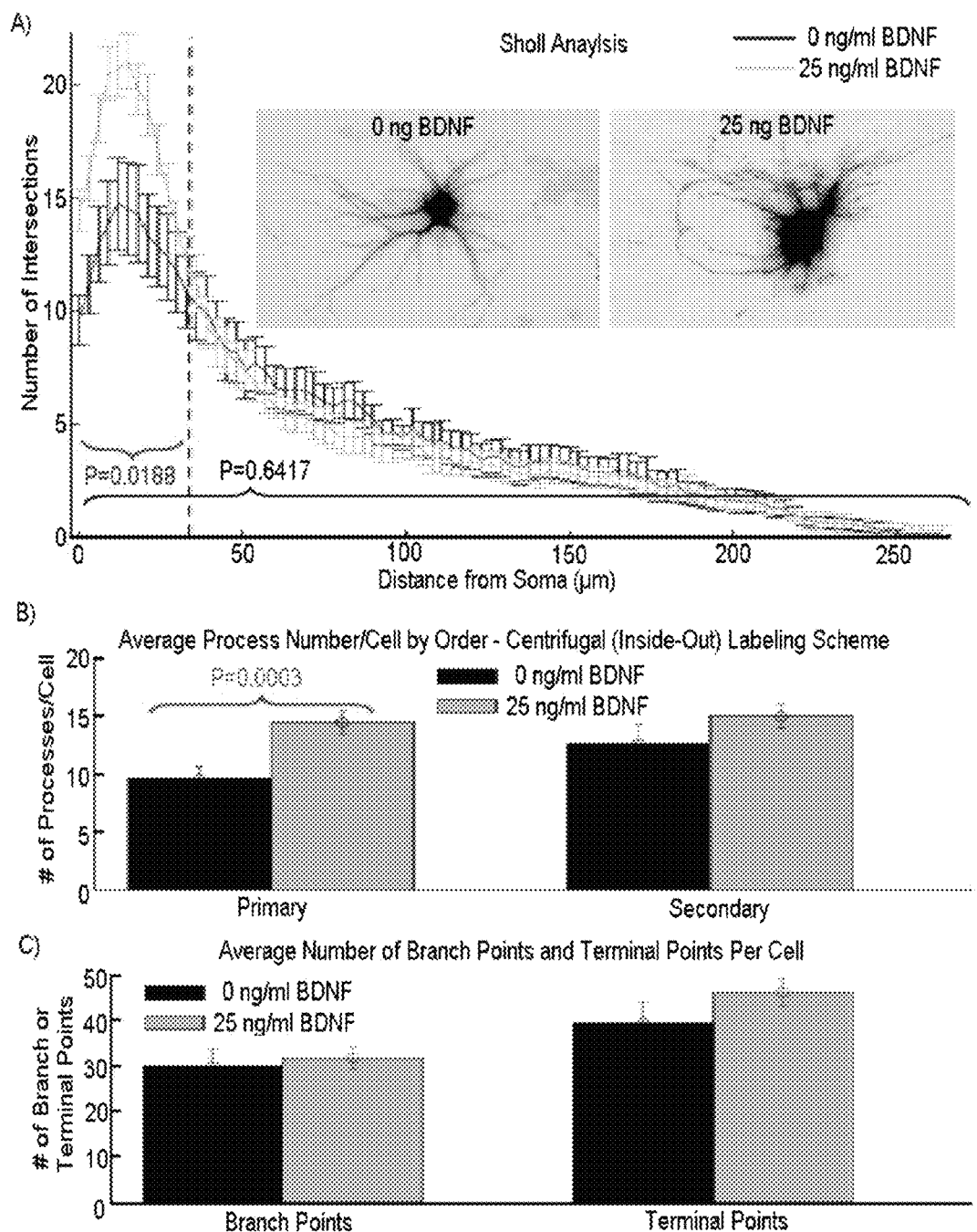

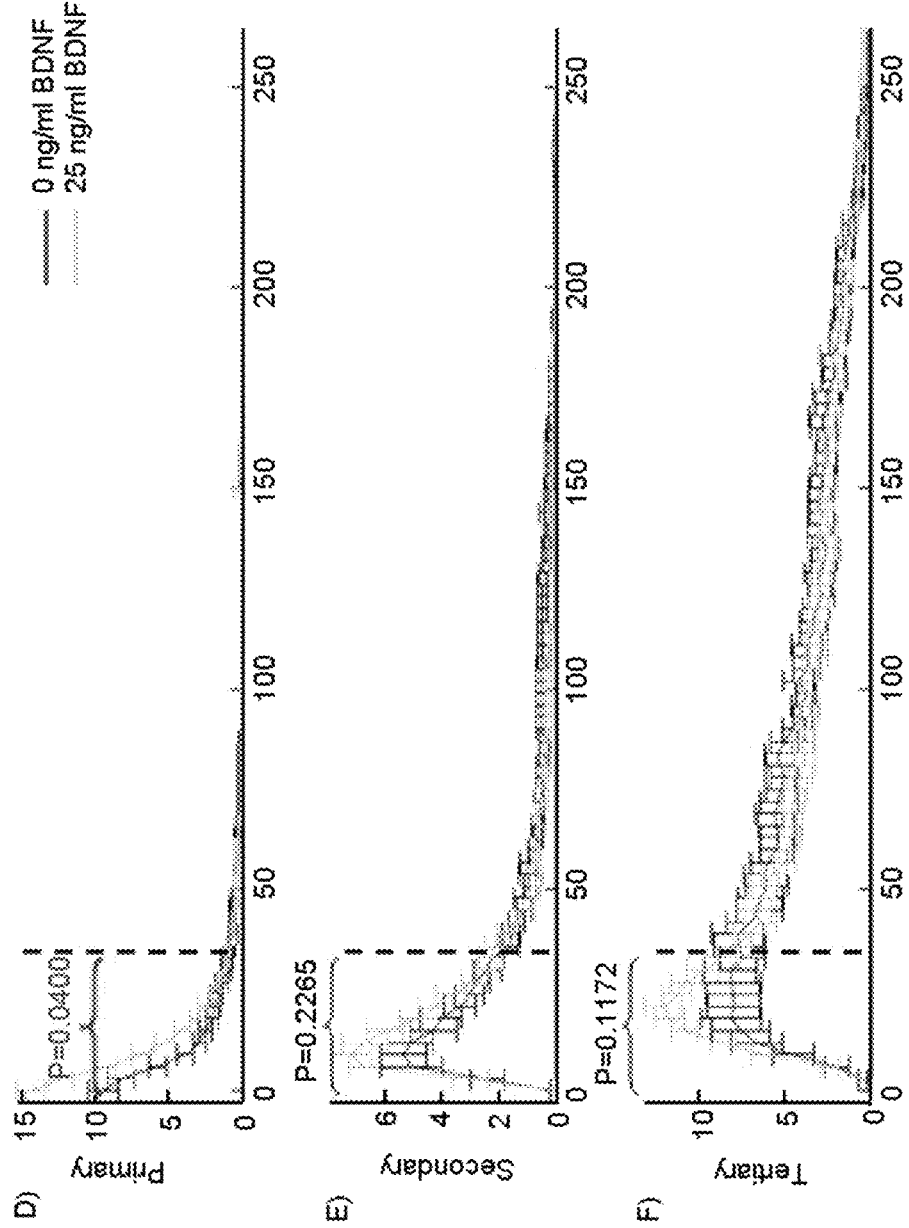

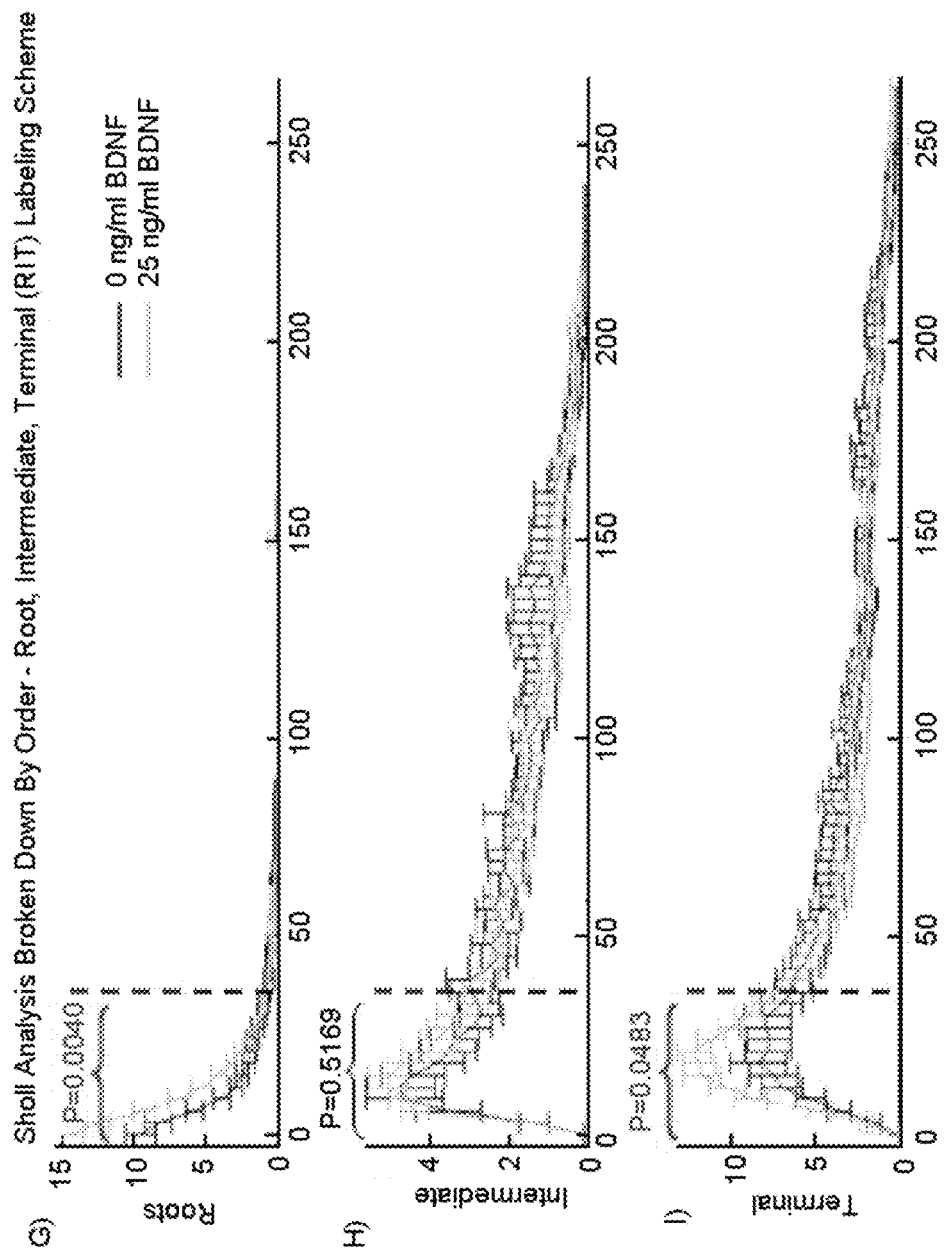
FIGS. 8G-I

FIGS. 10A-B
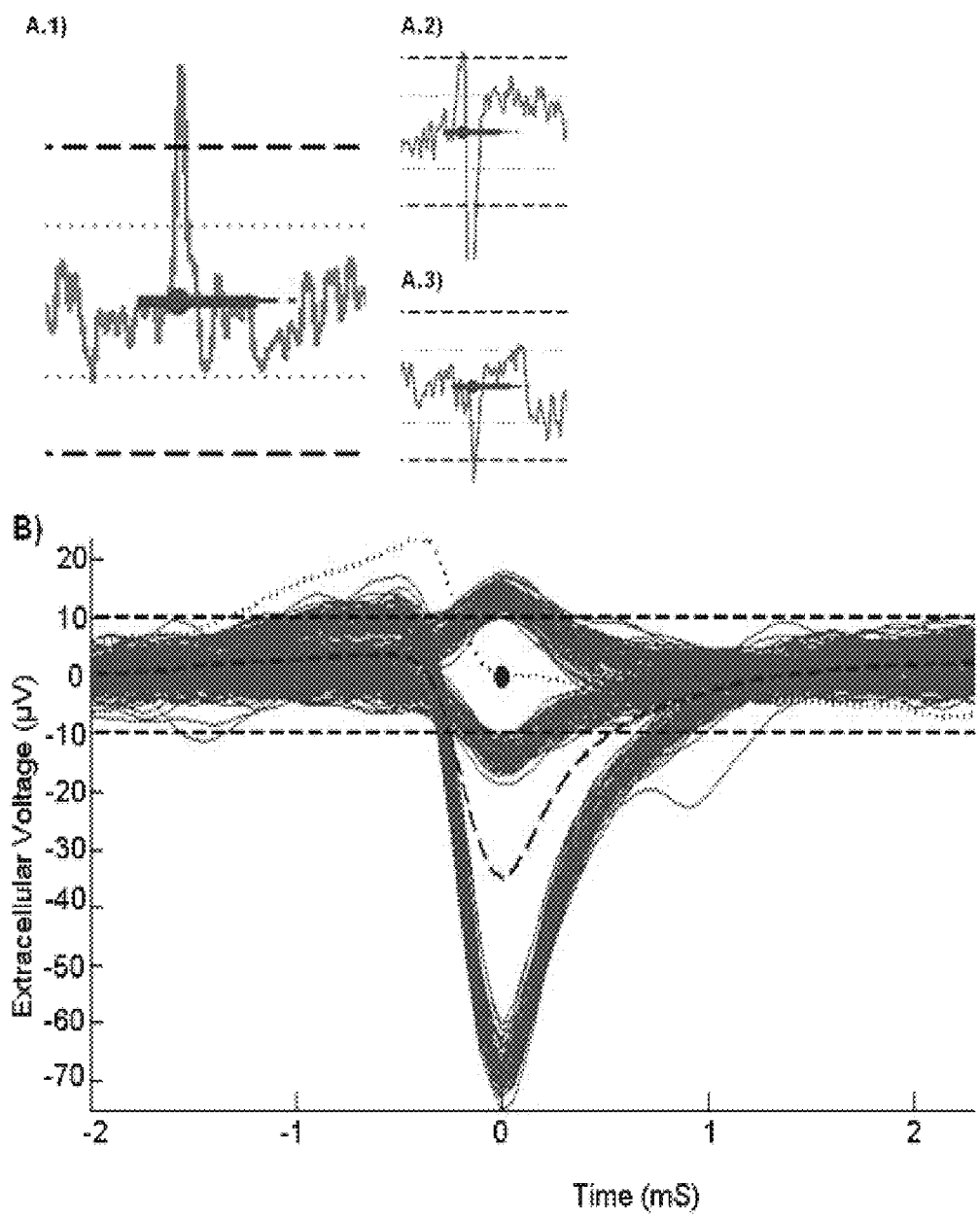

FIGS. 13A-B
A)
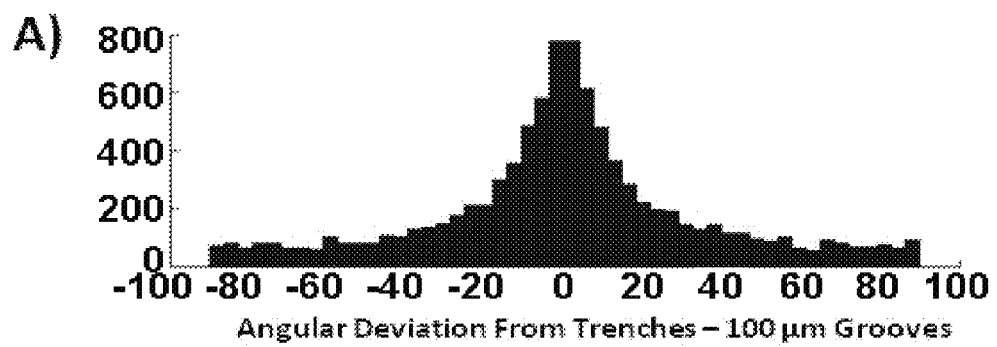
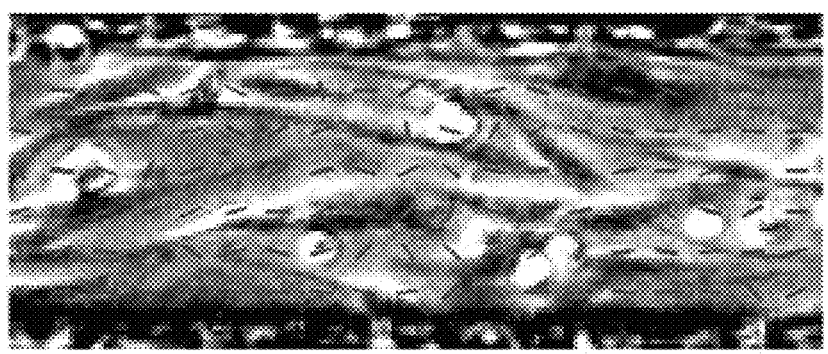
B)
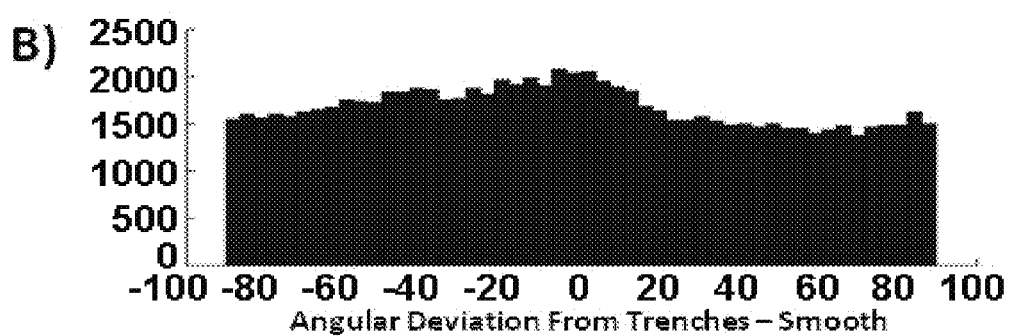

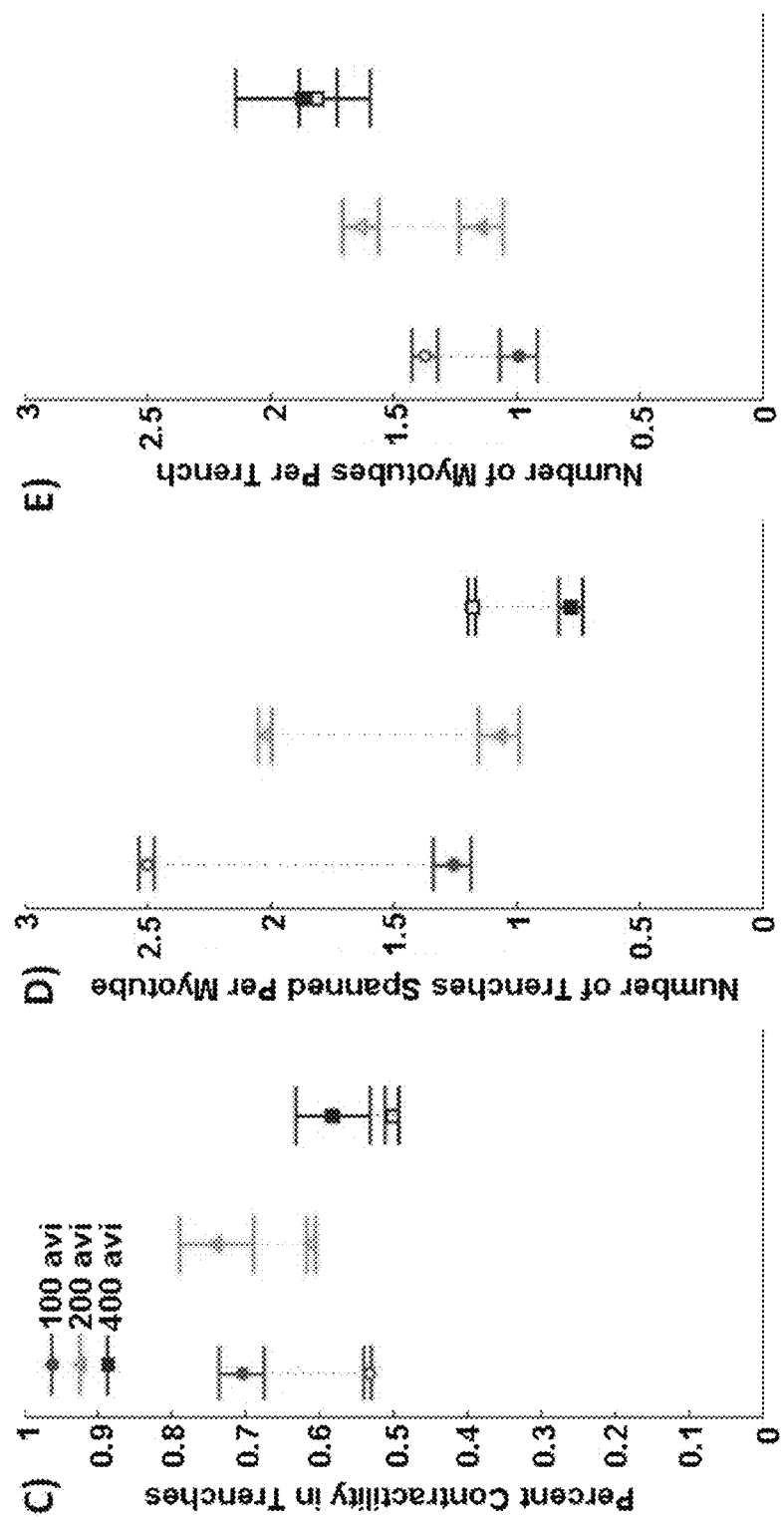
FIGS. 14C-E

FIGS. 15A-F
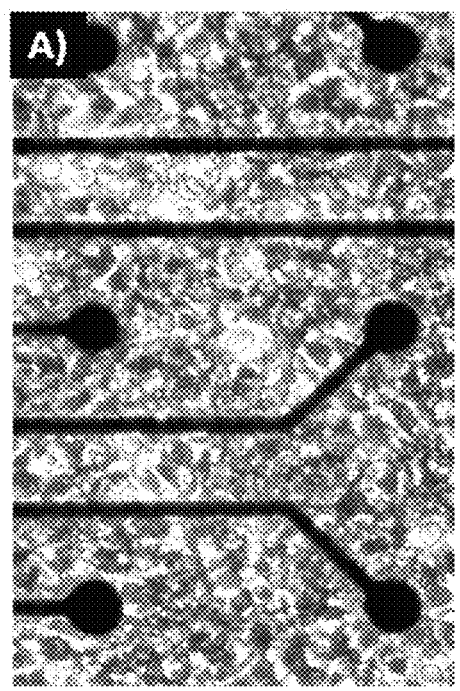
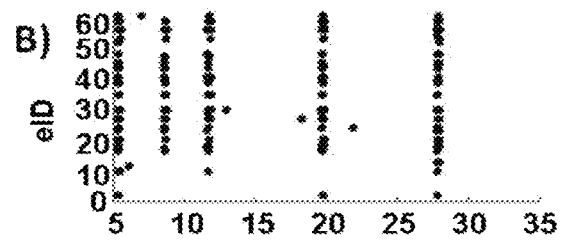
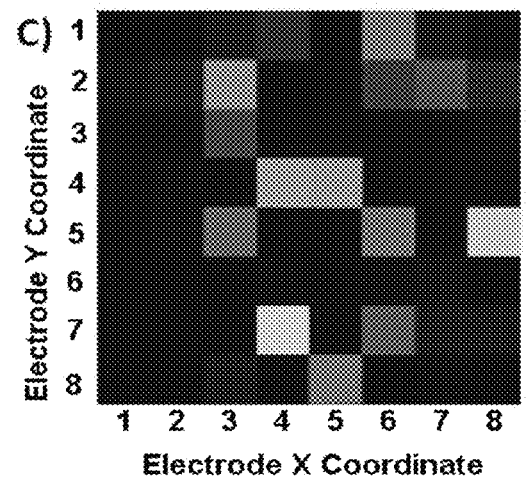
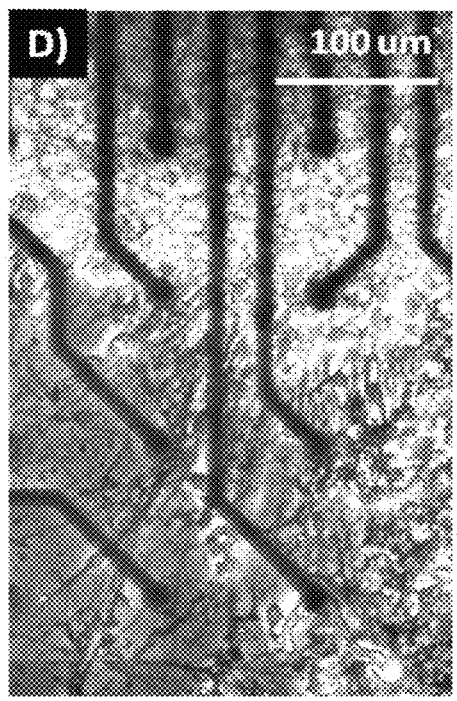
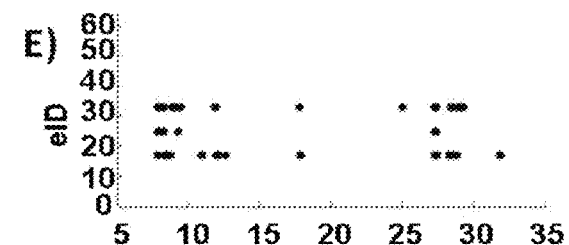
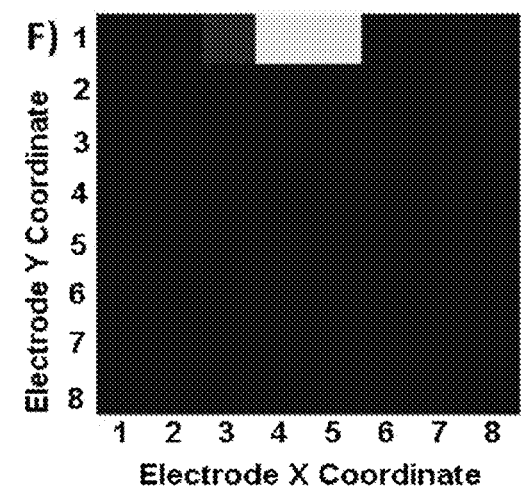

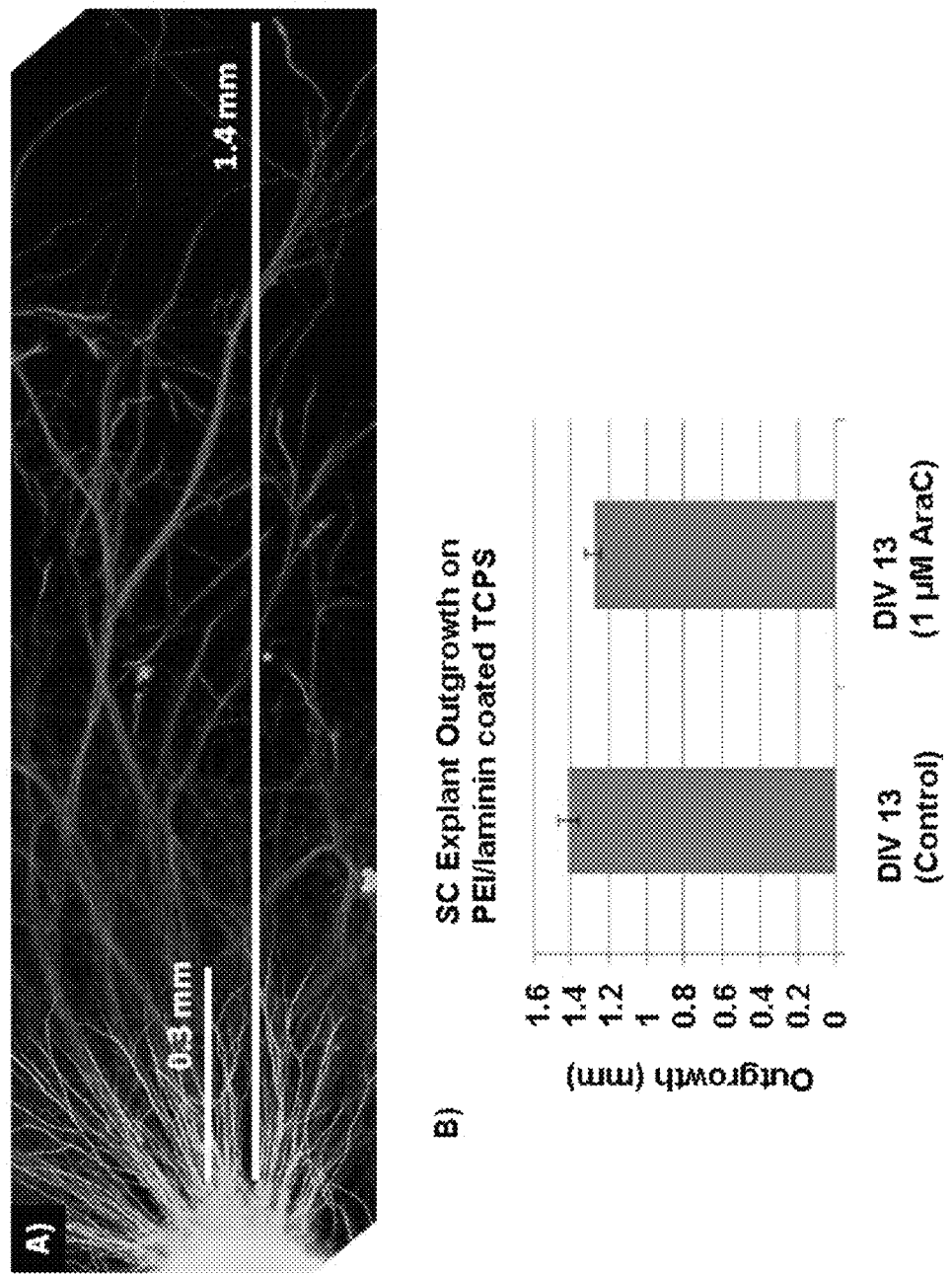
FIGS. 16A-B

FIGS 18A-B
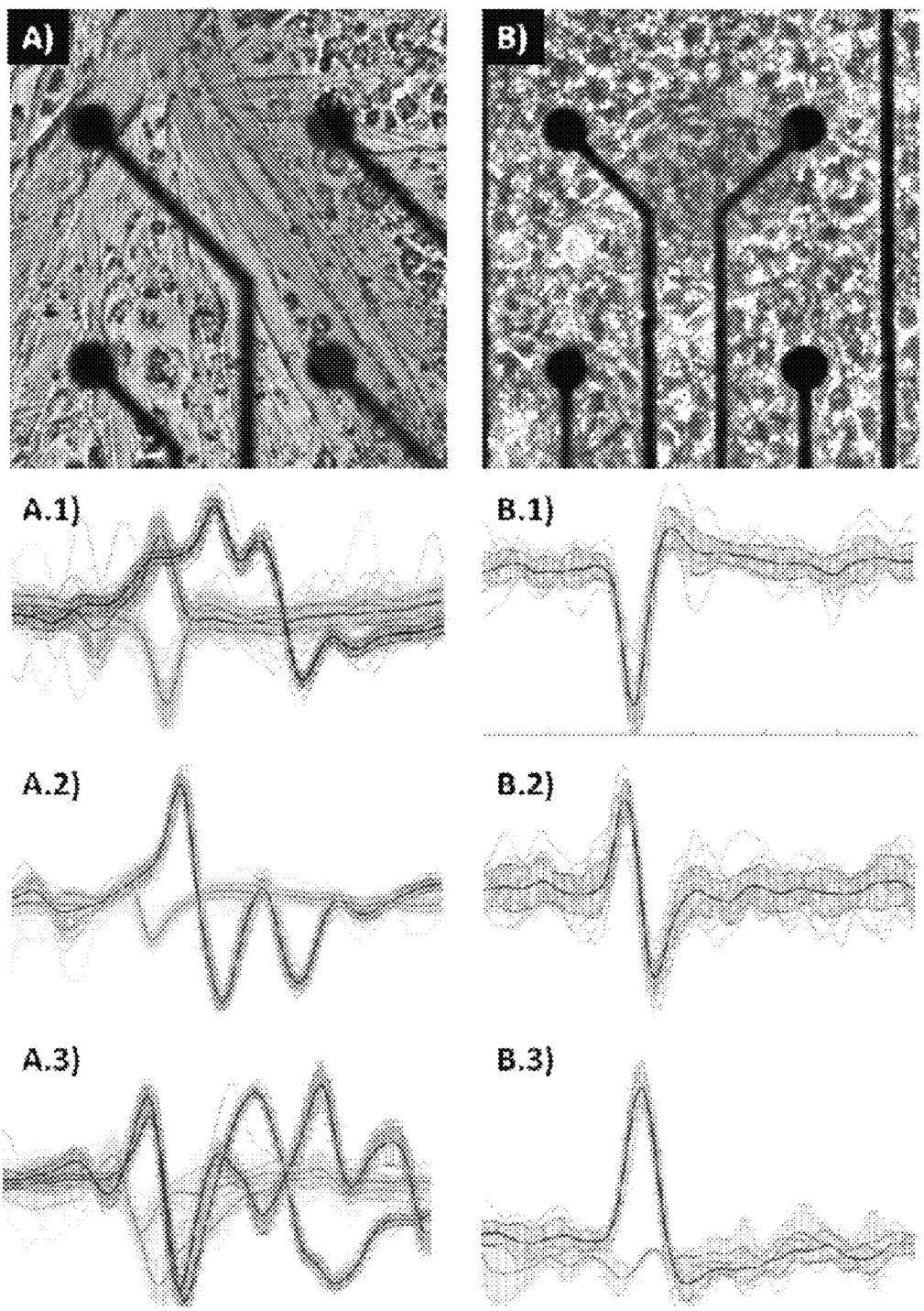

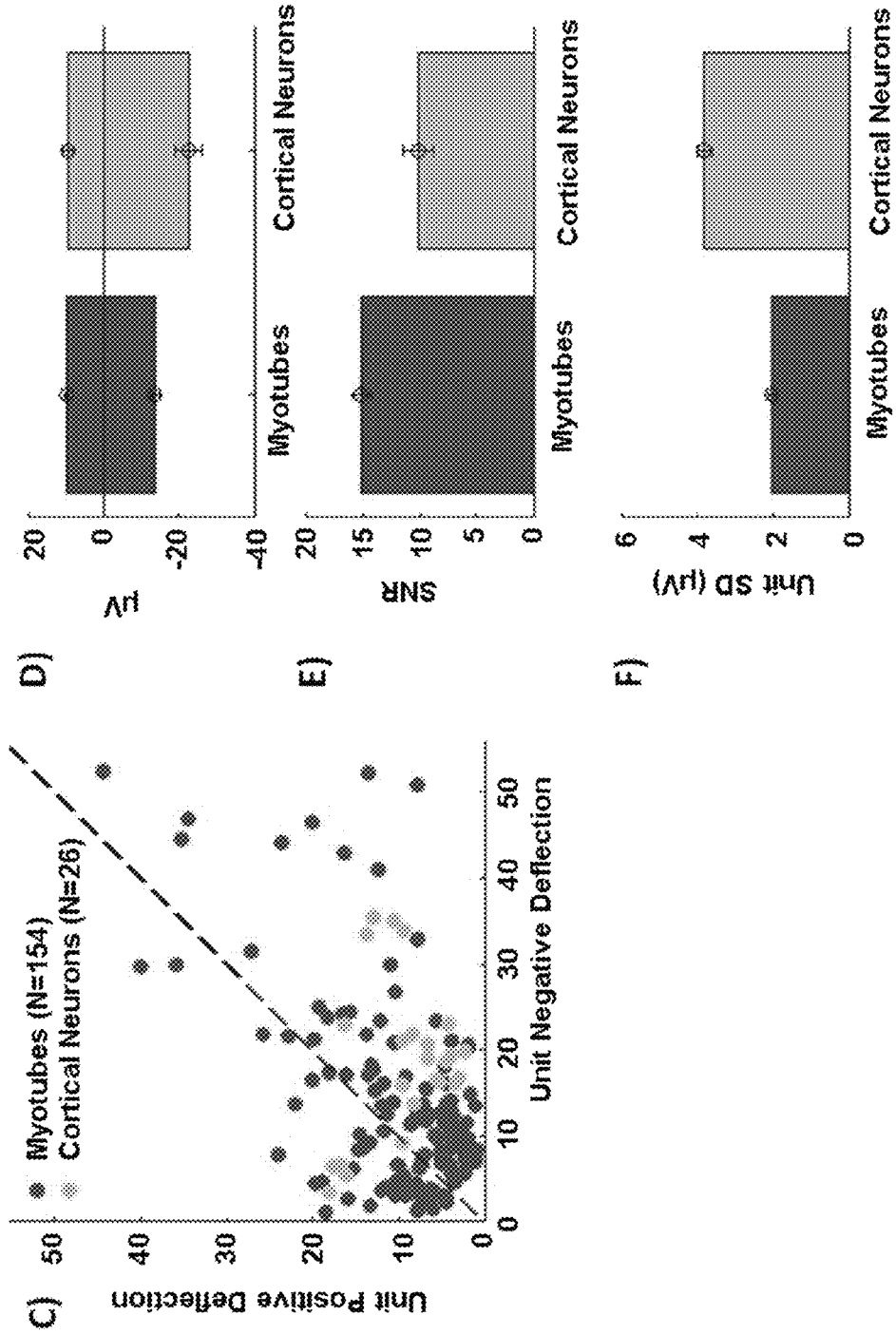
FIGS. 18C-F

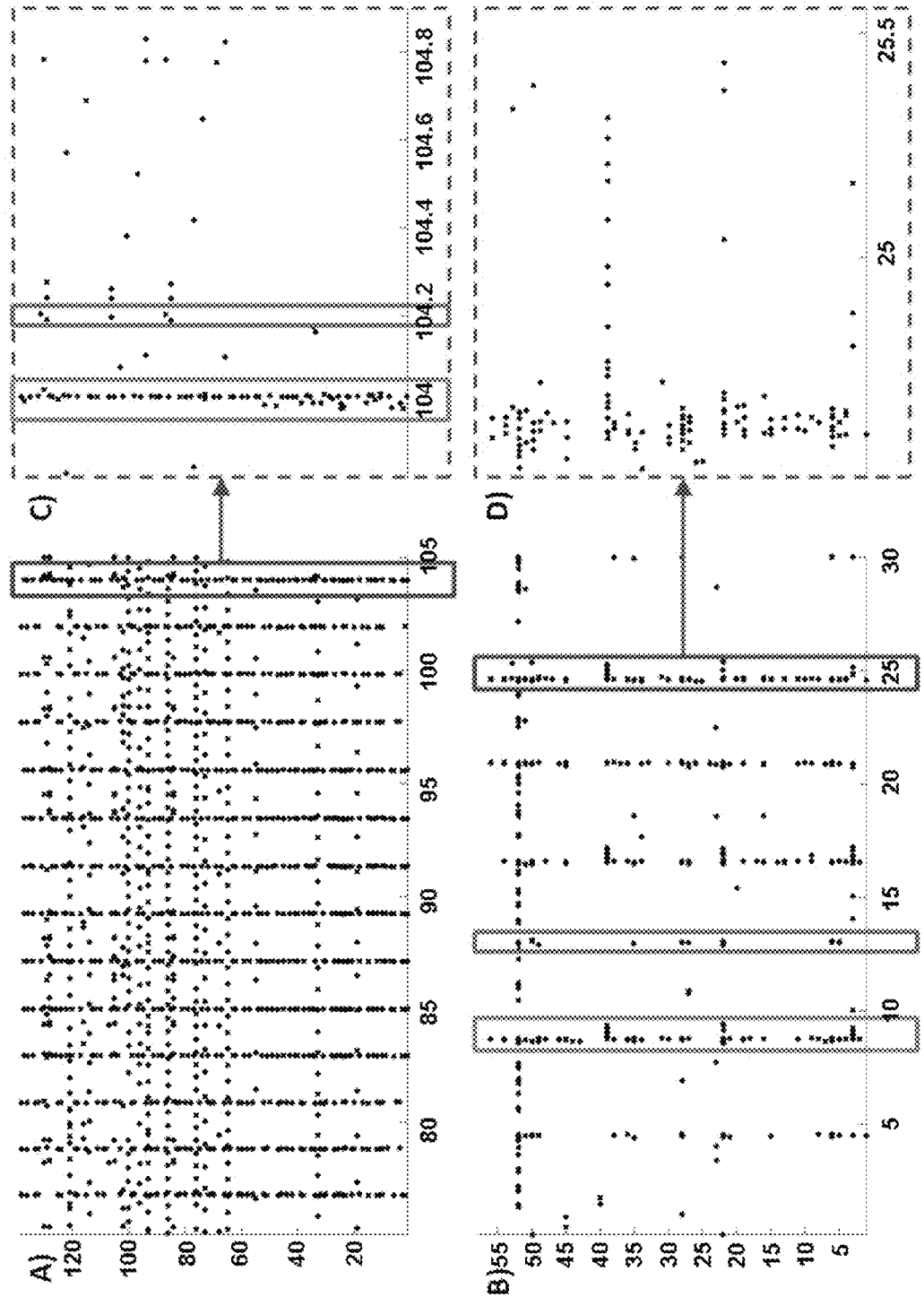
FIGS. 19A-D

FIGS. 20B-E
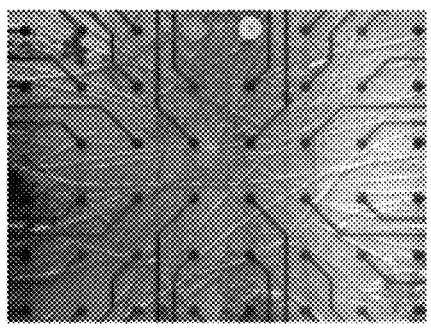
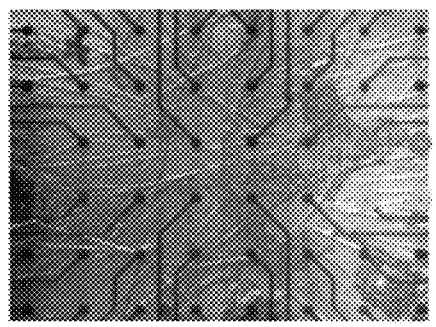
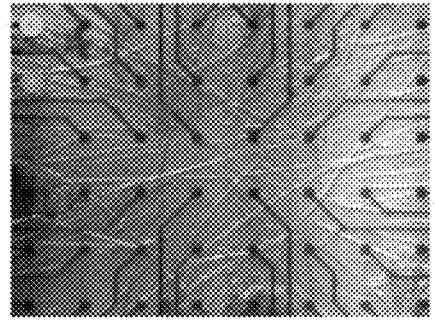
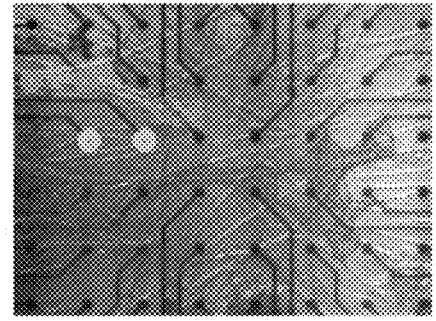

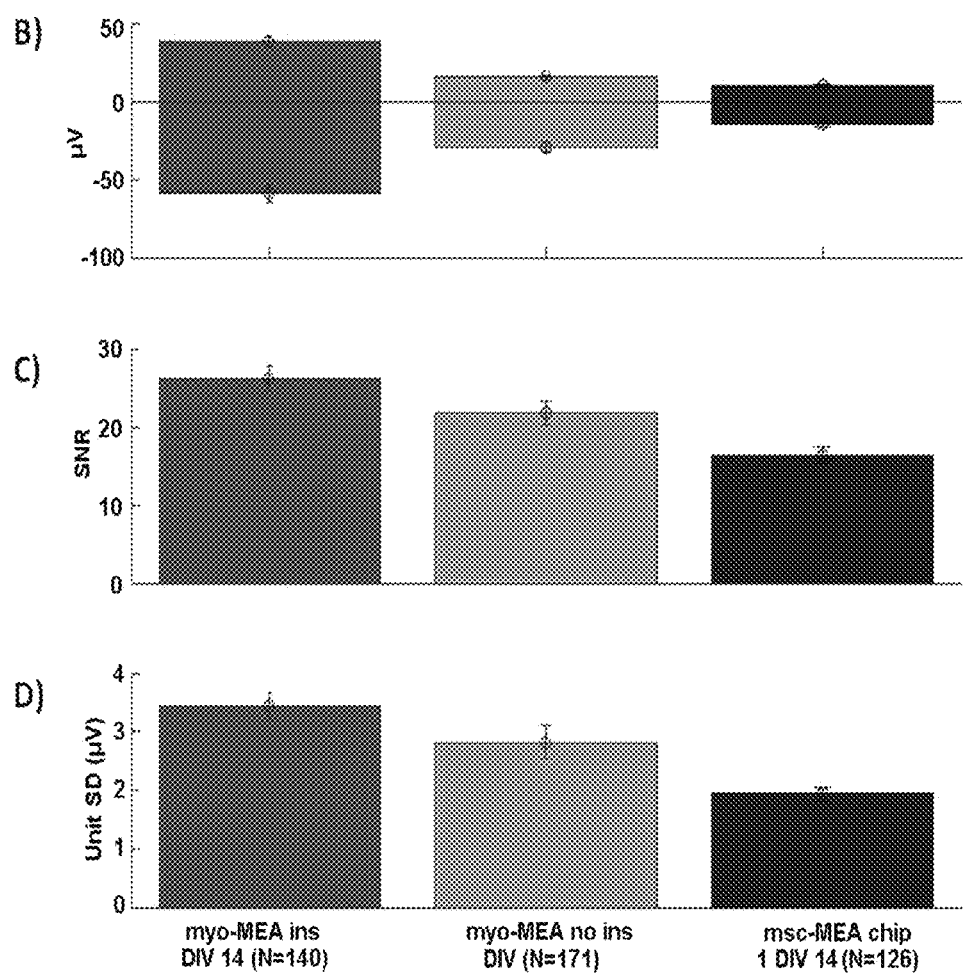
FIGS. 24B-D

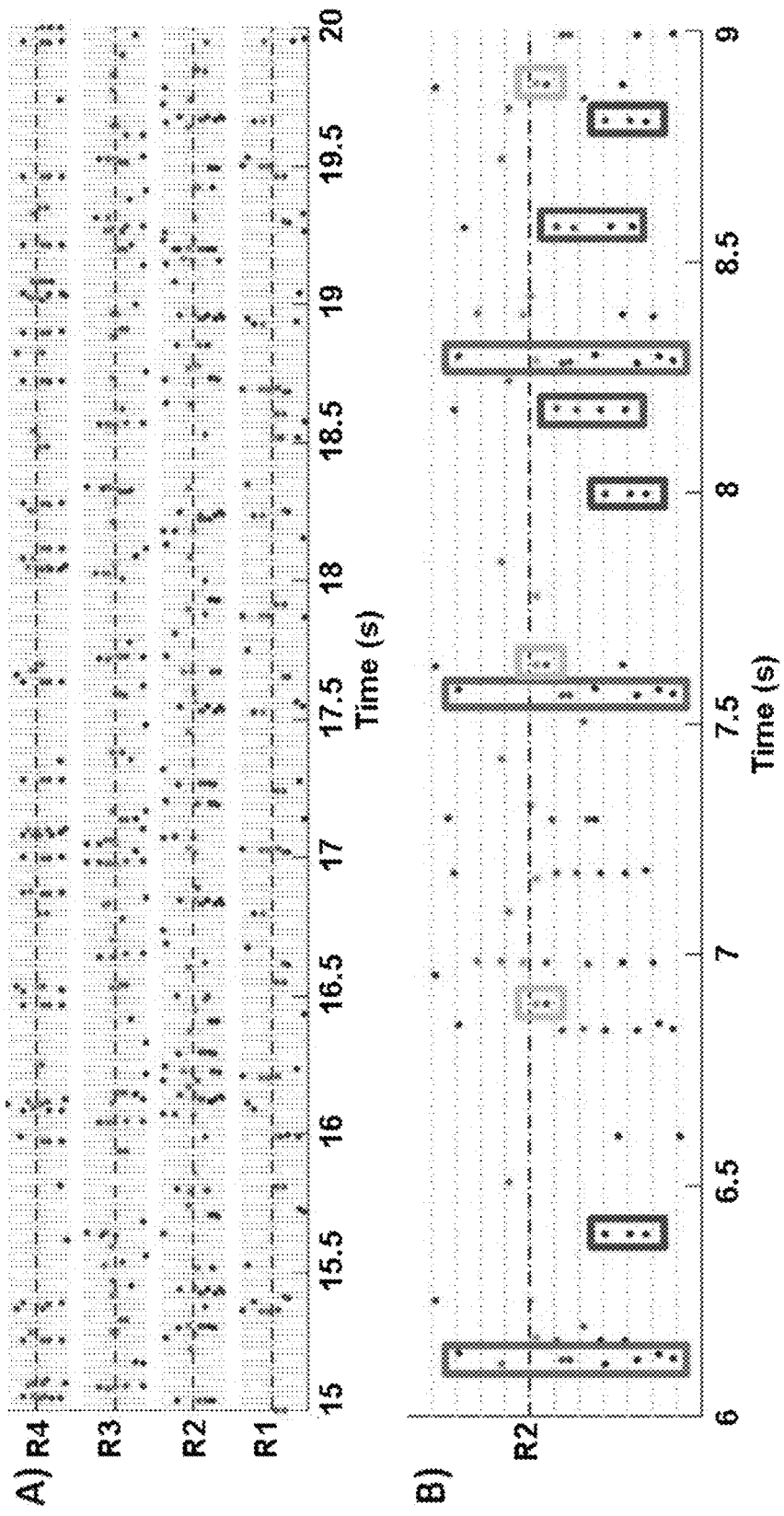
FIGS. 25A-B

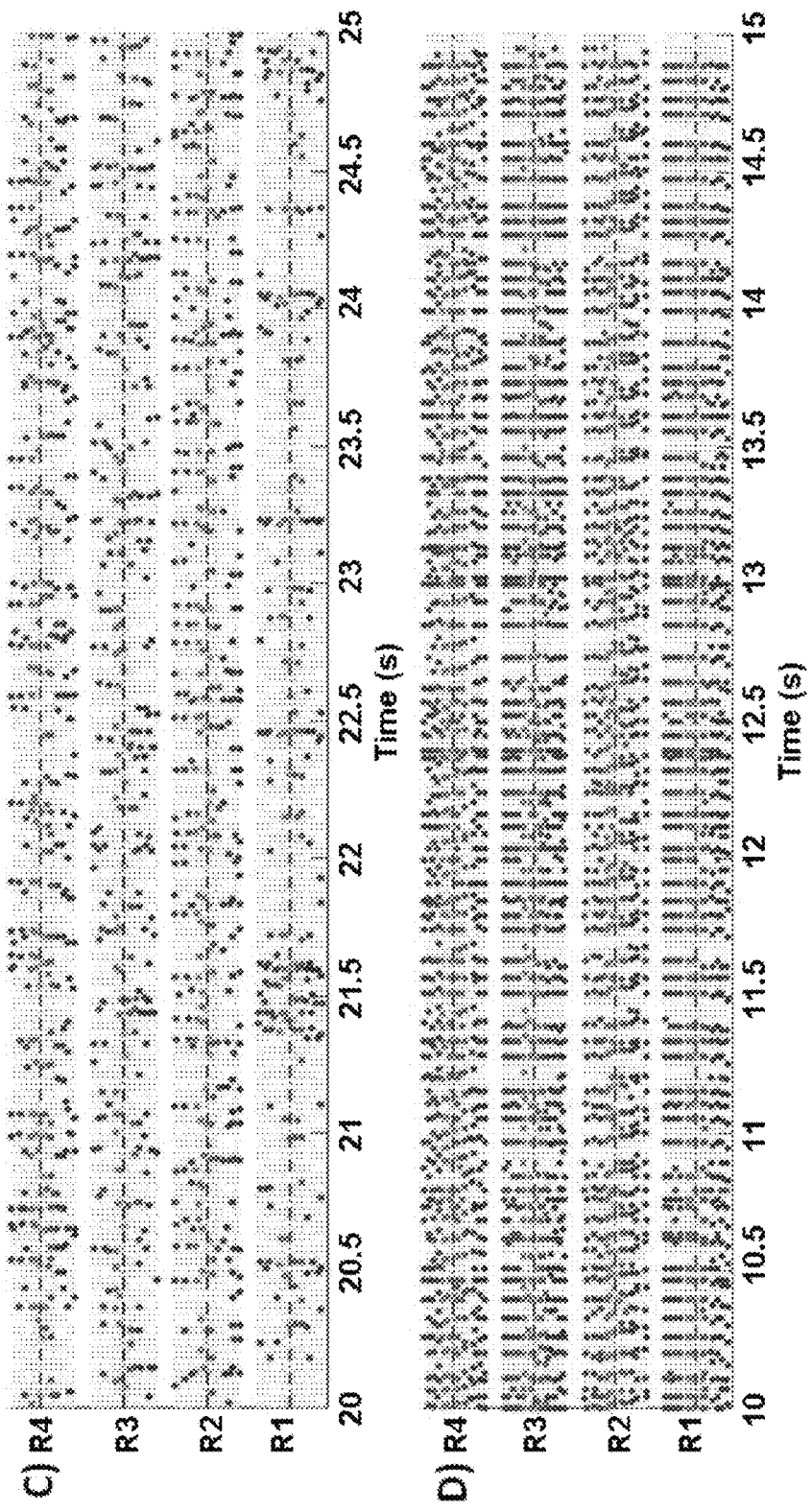
FIGS. 25C-D

FIG. 26 B
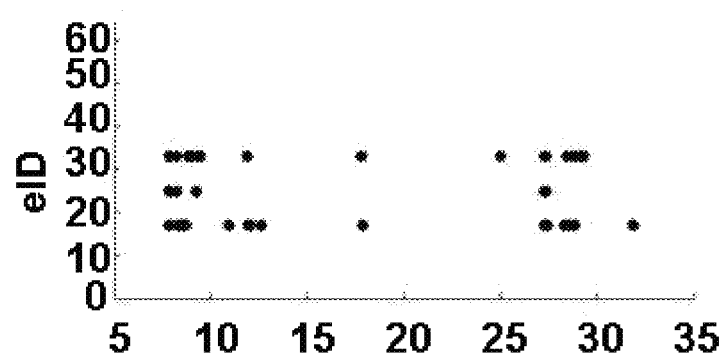
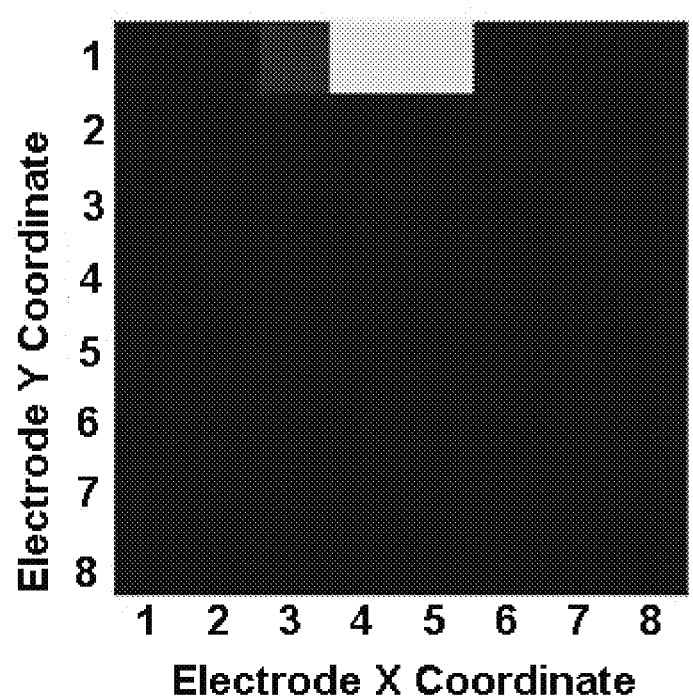

FIGS. 27A-B
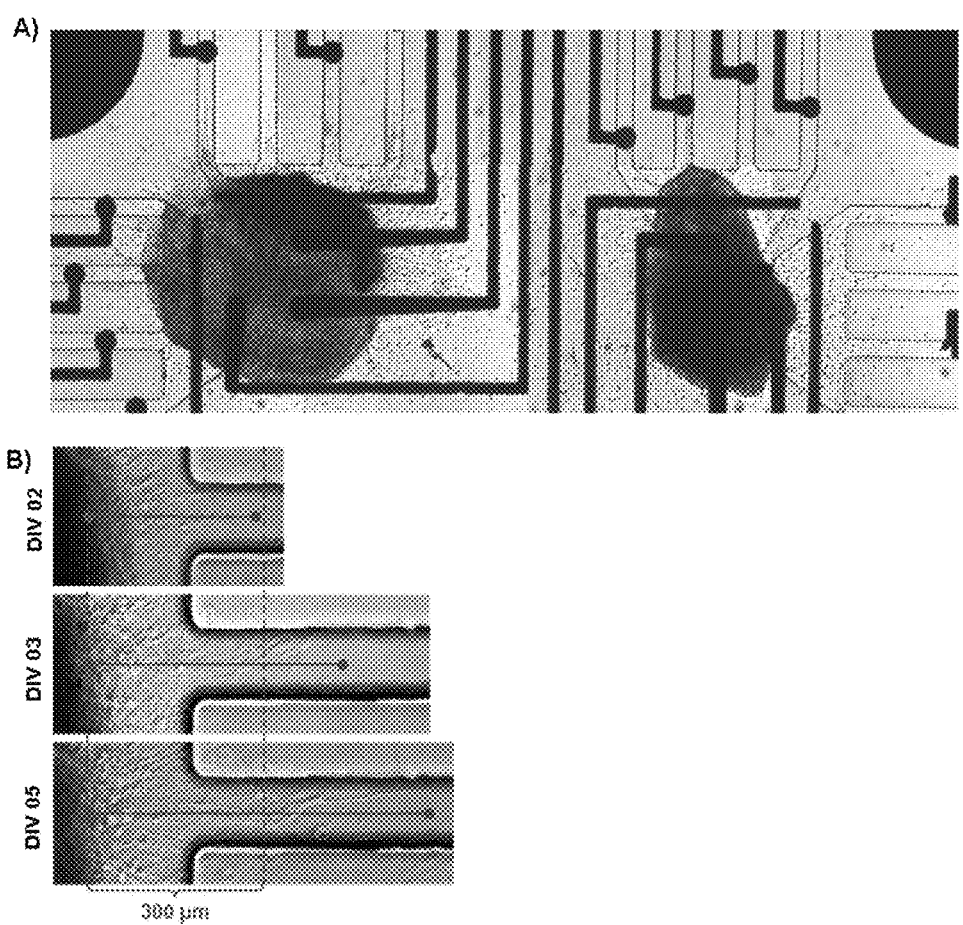

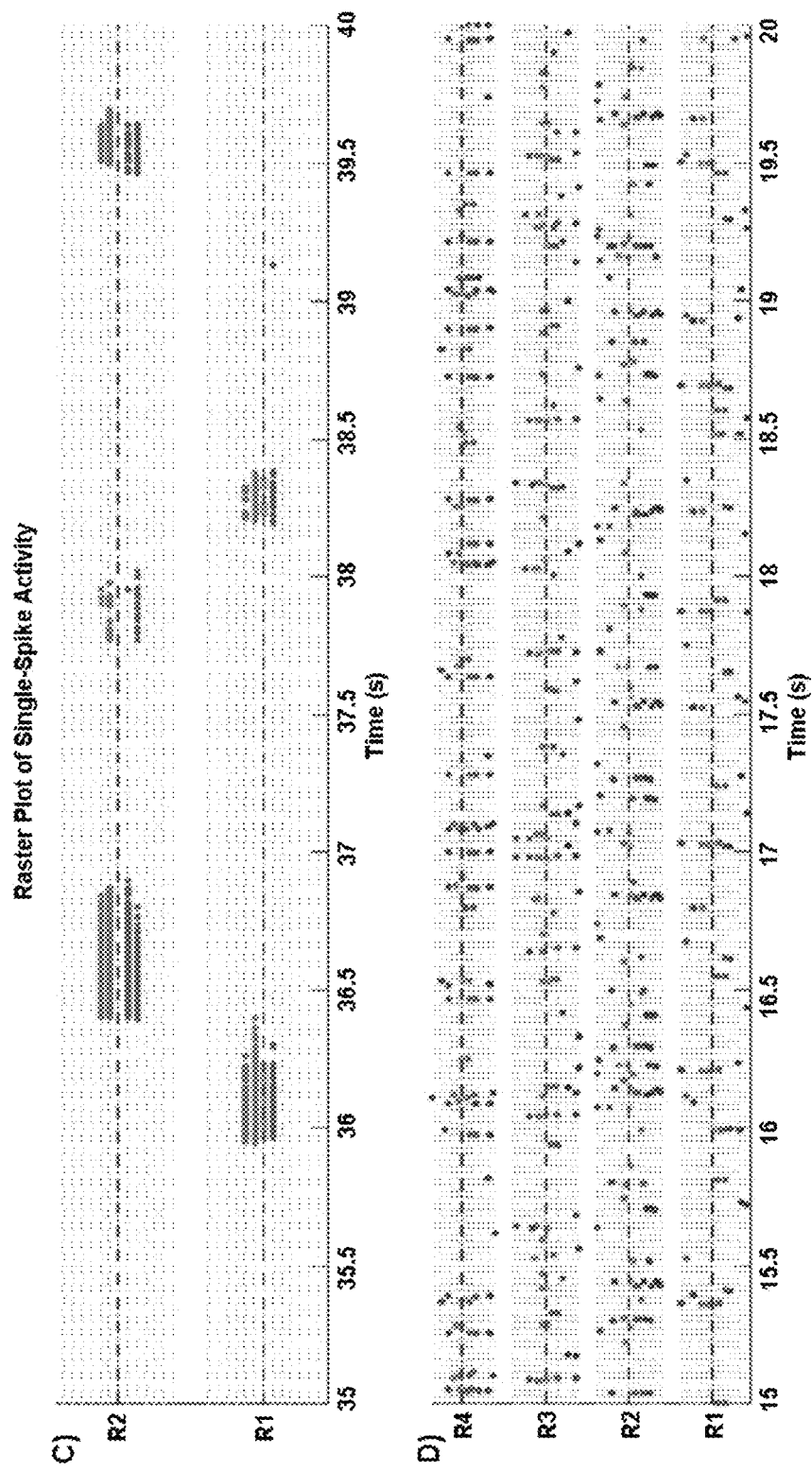
FIGS. 27C-D

FIGS. 29A-B
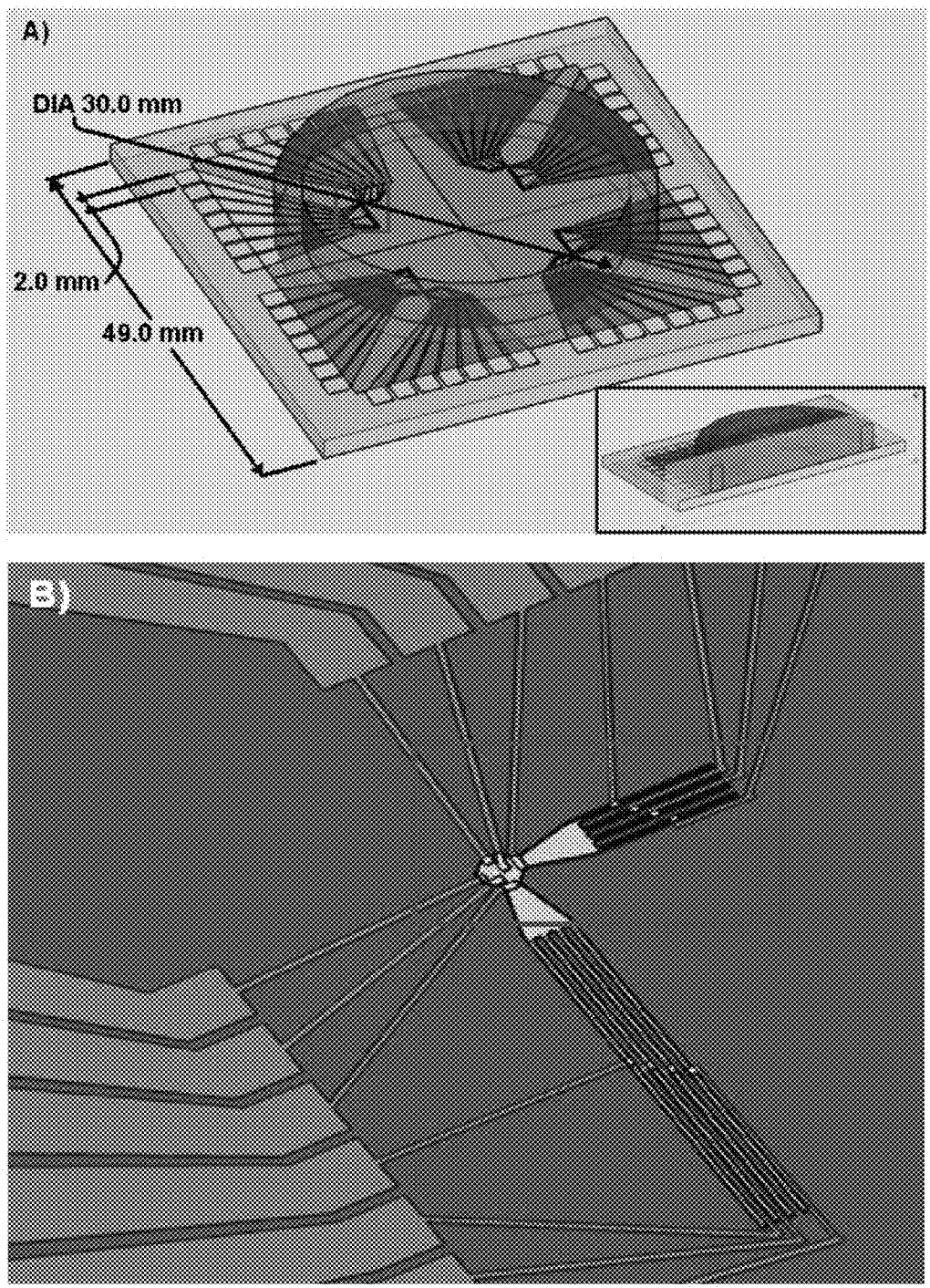

FIGS. 29C-E
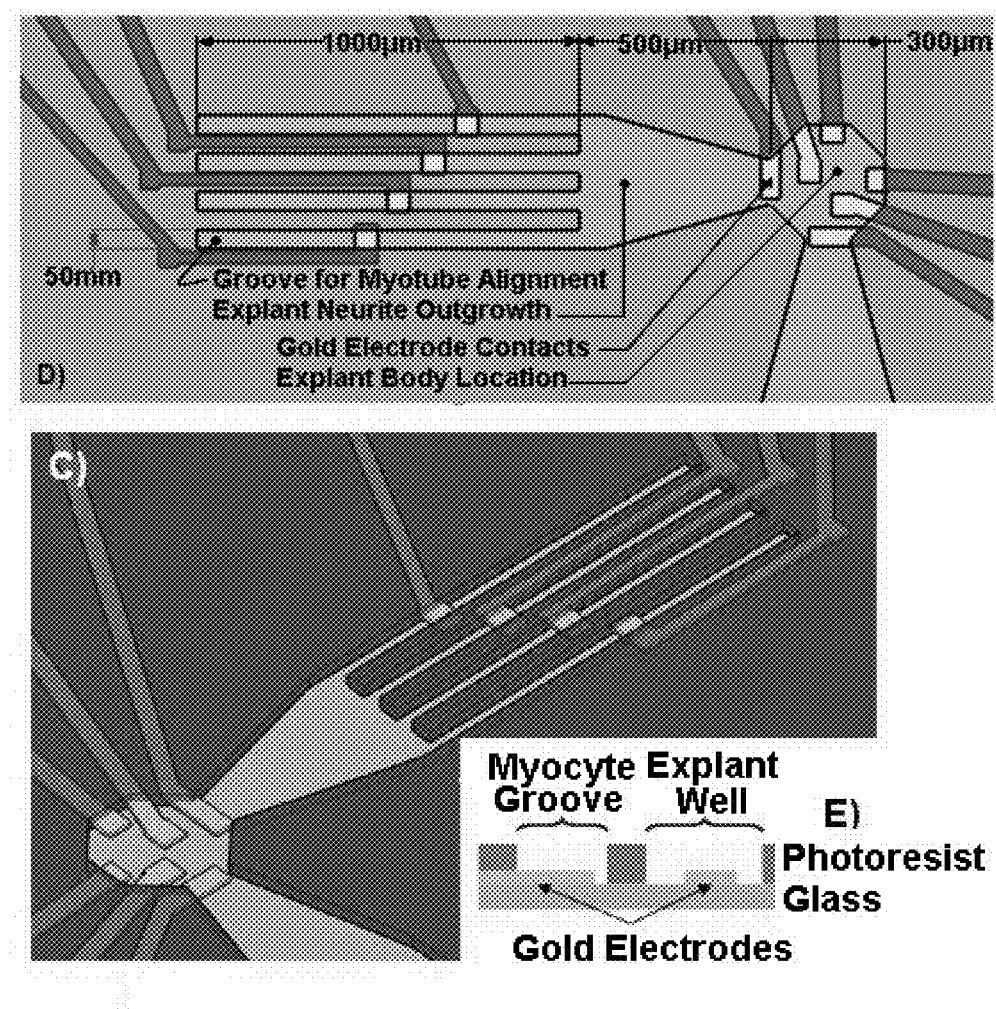

MICROELECTORODE ARRAY, METHODS FOR PREPARING THE SAME AND USES THEREOF

CROSS-REFERENCE TO RELATED APPLICATIONS

This application claims the benefit under 35 U.S.C. §119 (e) of U.S. Provisional Application 61/313,828 filed on Mar. 15, 2010, the teachings of which are incorporated herein by reference.

FIELD OF THE INVENTION

The present invention relates generally to neural interfaces. More particularly, the present invention discloses systems and related methods that employ microelectrode arrays cultured with myotubes to provide a neural interface.

BACKGROUND OF THE INVENTION

Neural interface designs are diverse, including multiple cortical, deep brain, spinal, non-invasive, and peripheral nervous system (PNS)-based approaches to stimulation and recording. There are an estimated 1.7 million Americans living with limb loss, and many more suffering from injury without expected motor recovery, who may benefit from a neural interface that can help place a prosthetic actuator directly under neural control. Technologies exist capable of recording neural activity from both the PNS and central nervous system (CNS), but they face problems acquiring large enough numbers of independent and appropriately tuned neural signals to provide reliable dexterous control.

The ideal neural interface is a bidirectional transducer that establishes contact between a technical device and neural structures within the body. The objective of such devices is to record bioelectrical signals from the nervous system or to implant such signals in order to restore motor and sensory function in disabled patient. Research in the fields of neural interfaces and neural prostheses focuses on restoring motor and sensory function in patients with limb amputations, spinal cord injury (SCl), stroke and degenerative diseases. However, advances in these fields have thus far translated into only modest clinical improvements despite the technologies' tremendous potential.

Neural prosthetics are artificial extensions to the body that restore or supplement functions of the nervous system lost during disease or injury. Typically, a neuroprosthetics device includes some sensor or actuator that interacts with the environment and a neural interface responsible for communicating with the nervous system. The neural interface is the point at which the machine exchanges information with the nervous system. In the case of sensory prostheses, such as a cochlear implant, the neural interface is designed to insert signals into the nervous system by stimulating the nervous tissue, while in the case of motor prosthetics, such as those currently under development in many laboratories, the purpose is to extract signals from the nervous system by recording the activity of the nervous tissue.

Long-term efforts are aimed at creating hybrid systems capable of two-way communication with the nervous system for restoring full function to amputees as well as to other patient groups. The major hurdle to progress in the clinical advancement of neuroprosthetics devices is the development of neural interfaces capable of efficient communication with the nervous system.

The mechanical capabilities of currently available prosthetic devices have become sophisticated. However, motor tasks are driven by gross anatomic movements or low bandwidth myoelectric couplings, making them cumbersome. For such prostheses, communication with the user is the weakest link in the chain of components that includes electronics, computing, actuators, mechanisms, and materials, all of which are adequate for the application. Neuroprosthetic devices aim to correct this deficiency by placing the prosthetic actuator directly under neural control. One subtype of neuroprosthetic device, a neuro-muscular prosthesis, captures neural signals involved in motor intention and redirects them for use in controlling an artificial device. Efforts to move such devices into clinical practice have been slowed by the lack of a neural interface capable of recording neural signals effectively enough to restore fine motor control or sensory function.

Current reviews of neural interface design highlight the following functional criteria as bottlenecks in the continued progress of this field: 1) obtaining stable, long-term recordings of large populations of neurons, 2) developing computationally efficient algorithms for translating neuronal activity into command signals capable of controlling a complex artificial actuator, and 3) determining how to use brain plasticity to incorporate prosthetics. While small populations of highly tuned neurons can accurately predict movement parameters, highly tuned neurons are rare in a random sample of cortical cells. Because motor information is represented in this highly distributed way, large samples of recorded cortical neurons are preferred.

It has been estimated that recordings from 500 to 700 cortical neurons would be needed to achieve 95% accuracy in predicting one-dimensional hand movements. The minimum number of recordings required to transform thoughts into a reasonable range of motions most likely exceeds 1000, a number presently exceeding the capabilities of cortical probes. As an analogy, imagine trying to read a computer screen with only a small number of pixels. The more complex the message, the larger the number of pixels required to read it. Hence, it may be desirable to have diverse approaches for both simplifying the message and improving our ability to read it. This may require the development of diverse methods to record and decode motor intention as well as targeting multiple regions of the nervous system.

The intention to perform an action is born in the cortex of the brain, is processed through multiple regions of the brain and spinal cord, comprising the central nervous system (CNS), and is transmitted along the axons of the peripheral nervous system (PNS), finally arriving at the neuromuscular junction (NMJ) where it triggers the depolarization and contraction of the specific muscle cells required to perform the desired action. There is continual debate on where in this chain of transmission is the best location from which to derive a useful motor signal, and therefore, to target with a neural interface.

Historically, many have designed neural interfaces with the intention of communicating directly with cortical tissue. Most of these efforts use penetrating microelectrode arrays (MEAS) to record depolarization of cell bodies. With these designs, electrodes located at the end of micron-scale spikes are inserted directly into central nervous system (CNS) tissue. While there are a number of benefits to this approach (most notably that it is technically simple to record a neural signal from a region where the large neuronal cell bodies may be accessed), progress is confounded by the complicated encoding of information in cortical brain regions and by the highly invasive nature of implanting any foreign device in the CNS.

Complicating issues for these electrodes include poor long-term recording due to fibrous encapsulation, inflammation, death of surrounding neurons and insufficient data transfer and decoding ability to interpret signals recorded at the cortical implantation site. These devices have yet to perform at the level necessary to justify their use in large-scale clinical trials but are in use in a limited number of clinical trials with a small number of patients.

As an alternative to targeting the CNS, other groups have developed means of targeting the PNS. An MEA-based neural interface that targets the PNS improves on current technology by taking advantage of the specific nature of the PNS in managing motor control. Each conscious action originates with upper motor neurons in the motor cortex that trigger a neural network distributed across brainstem nuclei, cerebellum and spinal cord. This neural network synthesizes input from thousands of tactile, positional, and visual sources with motor intention from the primary motor cortex to derive controlled motor output. Recording neural activity in the PNS after it has passed through the many processing steps occurring in the spinal cord, brainstem, and cerebellum may result in increased information content in the resulting signal.

A clinically relevant example of this phenomenon is cochlear implants, which restore hearing by directly stimulating the nerve cells in the cochlea. Attempts to stimulate more central areas of the auditory pathway have been less successful. Experts suspect this failure is secondary to the loss of important signal processing in the periphery. Due to its comparative physical accessibility, the discrete encoding of motor and sensory signals, the regenerative capacity of peripheral axons, and the reasons discussed above, the PNS may represent a more convenient location for accessing neural signals.

Neural interfaces that target the PNS pose a good compromise between the benefits and drawbacks of many types of neural interfaces. However, even in the PNS, interfaces with good specificity (i.e., the ability to record the activity of specific neurons) pay the price of being more invasive. Consequently, there are multiple PNS interface designs.

Extraneural electrodes, such as the cuff or epineural designs (relatively noninvasive and unspecific), attach to the outside of peripheral nerves. The most popular current examples are cuff electrodes, which attach to the outside of nerve bundles and record the activity of the fascicles (large, related axon clusters) with the nerve, but are only capable of recording a small amount of information.

Intraneural electrodes (more invasive but more specific) are inserted directly inside of the peripheral nerve where the recording sites can make nearly direct contact with the axons transmitting information. Notable examples include longitudinal intrafascicular electrodes (LIFEs), but also a number of other penetrating electrode designs have also been deployed in the PNS, though at this point these are primarily used for stimulation rather than recording purposes (such as the Utah staggered electrode array (USER)).

Regenerative electrodes, such as the sieve electrode (highly invasive and highly specific), are placed in the gap of peripheral nerves that have been fully transected and record from axons which regenerate through the electrode. Problems with this type of interface are currently being addressed by the redesigning the recording sites to be tubular rather than planar. These tubular recording sites are frequently fabricated by rolling arrays of parallel microchannels (microgrooves) with incorporated substrate-embedded MEAS into cylindrical constructs for implantation.

The most clinically successful means of establishing a control signal for powered prosthetic devices has been recording the electromyographic (EMG) activity of residual muscles. Traditionally, this has been accomplished using residual muscles that were related to the activity of the prosthesis prior to amputation or by using EMG activity recorded from other unrelated muscles that have been retrained for prosthetic control. More recently a technique titled "targeted muscle reinnervation" (TMR) has been developed, in which the residual peripheral nerves left after an amputation are rerouted to muscles left useless by the loss of the limb.

These nerves regenerate onto the new musculature allowing the amputee to contract them by trying to perform actions with the missing limb, and providing a new EMG source from which more intuitive control over a powered prosthetic may be derived. All currently available myo-electric technologies depend on EMG recordings made at the skin's surface, and while muscle-implantable electrodes have been shown to be stable for long periods of time, such devices are almost exclusively used for functional electrical stimulation (FES) rather than EMG recording (with the notable exception of devices intended for diagnostic purposes).

Accordingly, there is an immediate need for improved neural interfaces and related neural interface methods.

SUMMARY OF THE INVENTION

In one aspect a bio-interface is disclosed that is capable of modulating myotube behavior and guiding myotube formation and contractility to specific locations.

Another aspect discloses integration of an embodiment bio-interface with a substrate-embedded MEA for the purpose of recording myotube activity selectively from independent myotubes, such as within a culture or patient.

Another aspect discloses integrating an embodiment interface with a neuronal system.

Various embodiments disclose a neural interface design that uses myotubes cultured on a topographically modified MEA as a means of extracting large numbers of independent neural signals pertaining to motor control from the PNS.

In one aspect a microelectrode array is disclosed with a substrate having a plurality of grooves and a plurality of electrical contact pads. Each of the grooves has at least one electrode electrically connected to a corresponding electrical contact pad, and also contains at least one myotube that overlays the electrode. In disclosed embodiments the myotubes are independent from one another. The substrate may include a laminin layer to encourage growth of the myotubes. In various embodiments the grooves have widths that are between 30 µm and 150 µm, and some between 30 µm and 70 µm. In certain embodiments the substrate is flexible and rolled into a cylinder such that the myotubes are trapped inside resulting channels. In embodiments at least one of the myotubes is attached to a peripheral nerve. In such embodiments, the plurality of grooves may be connected to a neural explant region on the substrate in which neural tissue is disposed to couple to the myotubes.

In another aspect a neural interface method is disclosed that includes causing neural tissue to couple with skeletal-muscular tissue disposed on a substrate that is in electrical contact with a plurality of electrodes on the substrate. Electrical signal information generated by the electrode from the skeletal-muscular tissue is used to infer corresponding neuronal firing information of the neural tissue. In embodiments the skeletal-muscular tissue includes a plurality of myotubes. In such embodiments topographical formation on the substrate are used to guide the myotubes to corresponding electrodes. In specific embodiments the substrate comprises a plurality of grooves, each groove comprising at least one electrode, and each of the grooves contains at least one myotube that overlays the electrode.

In another aspect a method of integrating skeletal-muscular tissue with a microelectrode array (MEA) is disclosed. Topographical formations are disposed on a substrate that has an MEA design. Skeletal-muscular tissue is seeded onto the substrate to form myotubes that are guided by the topographical formations to predetermined locations on the substrate. In embodiments each of the predetermined locations comprises a respective electrode.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 2 shows representative videomicrographs and accompanying embodiment VTA analysis.

FIG. 3 is a graph of success vector, failure vector, and net success scores.

FIG. 4 illustrates an embodiment program performance.

FIG. 5 illustrates frequency and sources of misclassification errors.

FIG. 8 shows results of an embodiment analysis for hippocampal neurons treated with 25 ng/ml BDNF and untreated control neurons.

FIG. 15 shows EAP spatial distribution in dissociated cortical culture vs. spinal cord explant culture.

FIG. 16 shows SC explant morphology and outgrowth.

FIG. 18 illustrates characteristic myotube-electrode and neuronal-electrode interactions.

FIG. 19 shows synchronous multi-electrode activation in myotube cultures and neuronal cultures.

FIG. 25 shows patterns of myotube activation on topographically patterned vs. uninsulated embodiment myo-MEAS.

FIG. 27 shows explant integration with an embodiment myo-MEA.

FIG. 29 shows yet another embodiment myo-MEA device.

DETAILED DESCRIPTION

Figure 1:
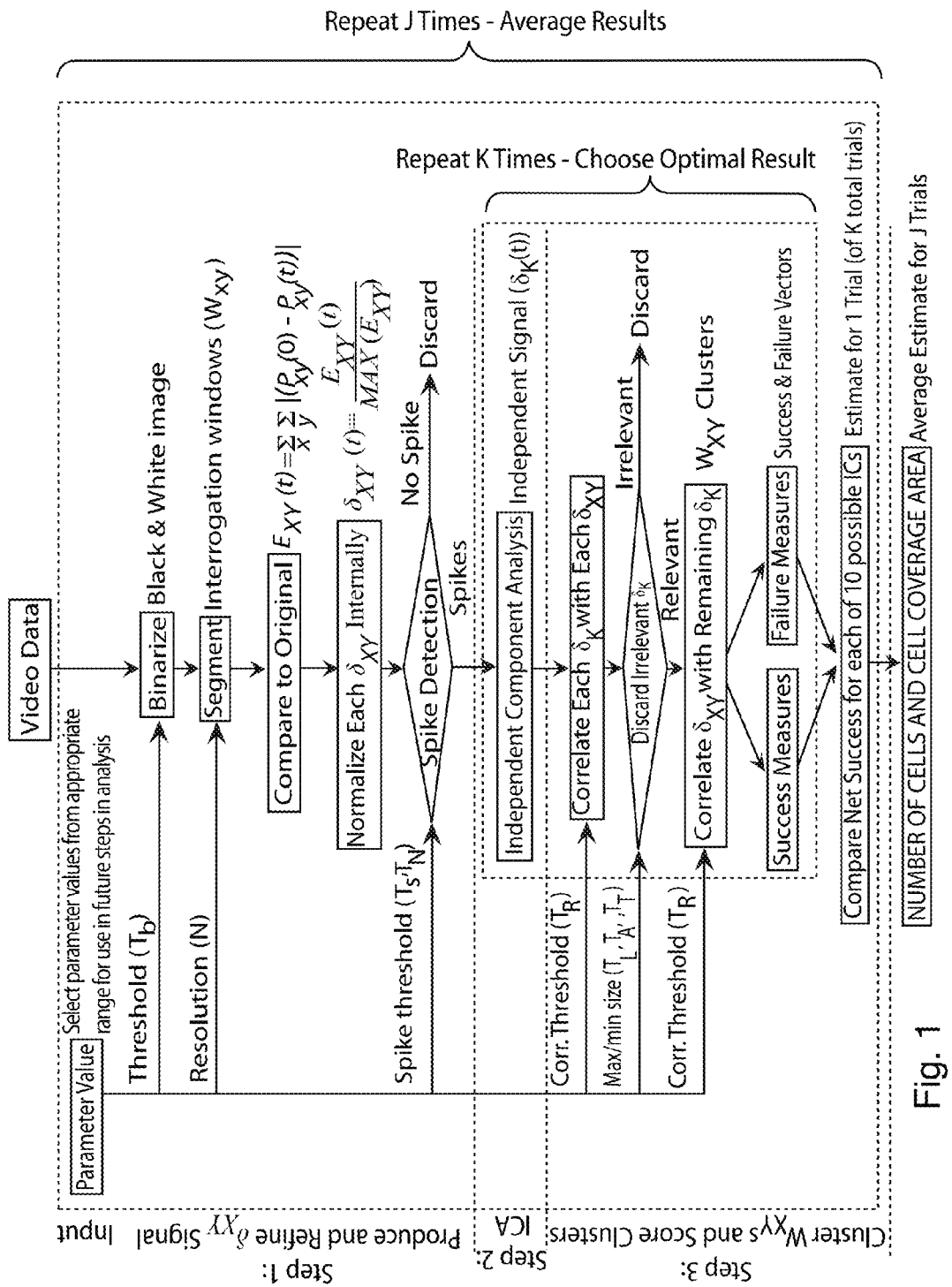
FIG. 1 is an embodiment VTA program processing flow chart.

An embodiment microelectrode array (MEA) can be designed to guide myotube formation to specific sites and can interact with these myotubes (recording or stimulating) in a selective manner. Embodiment MEAS may be used, for example, in a novel type of neural interface or in development of laboratory systems requiring the study of ordered muscle cell cultures or muscle/nerve co-cultures.

To demonstrate the ability of myotubes to transduce APs transmitted along α-motoneuron axons, the following aspects are discussed in the following:

Aspect 1—Providing a bio-interface capable of modulating myotube behavior and guiding myotube formation and contractility to specific locations, while maximizing the number of independently active myotubes.

Aspect 2—Integrating an embodiment bio-interface with a substrate-embedded MEA for the purpose of recording myotube activity selectively from independent myotubes within a culture.

Aspect 3—Integrating an embodiment interface with a neuronal system.

A modification of the known "cultured-probe" design, a neural interface in which neurons cultured directly onto an electrode surface prior to implantation facilitate incorporation into the host nervous system, may significantly improve the recording capabilities of current neural interfaces. By using myotubes rather than neurons as the electrogenic cell type cultured onto the electrode surface and by targeting the peripheral nervous system (PNS) as the implantation site, various embodiments may overcome many of the critical barriers to progress in this field. In various embodiments a modified planar microelectrode array (MEA) is provided that is designed to facilitate integration of muscle cells (myotubes), such as myotubes grown in culture grown in culture.

The embodiment MEA surface can be tailored to improve the sealing between myotubes and electrodes for improvement upon the ability of current devices to distinguish electrical activity of individual cells. Various embodiments may optimize the specificity with which the myotubes are able to interact with the electrodes, including the development of computational algorithms meant to interpret the multi-modal data that an embodiment device may generate. These myotubes may then act as biological signal amplifiers for action potentials received from regenerated motor neuron axons following amputation, creating a gateway for acquiring motor intention from the nervous system.

An embodiment neural interface employs a combination of electromyography, which takes advantage of the larger extracellular voltage changes caused by the depolarizations of muscle cells relative to those of neurons and cultured-probe techniques, which takes advantage of the high degree of specificity available to dissociated cultures grown on MEAS. Such a device may be desirable because recording from individual PNS axons may not be feasible with traditional approaches. Recording from motor axons in vitro is not currently feasible because they are comparatively small and create extracellular voltage changes below the detection limit for traditional MEAS. An embodiment myo-MEA enables the use of myotubes as a biological signal amplifier to record neural signals carried in spinal motoneuron axons. The myotube amplifies the signal traveling down the moto-neuron axon by virtue of coupling through the neuromuscular junction (NMJ) in much the same way a loud speaker amplifies the voice of someone speaking into a microphone.

Based on the relative success of EMG-based and PNS-based neural interfaces, various embodiment myo-MEAS are neural interface designs that combine the benefits of the two approaches. Myotubes can be cultured on an electrode array in a modification of the traditional cultured probe concept, specifically employing microscale grooves to accomplish two goals: 1) direct the formation of myotubes to specific electrode sites, and 2) to preserve myotube independence from one another. This is desirable in terms of increasing the number of independent signals available per unit surface area and maximizing the capability of such a device to record neural signals. Additionally, the topographical modification serves to stabilize the myotube culture, which can be mechanically disrupted by the contractions of the myotubes themselves over extended periods of time.

Various embodiments provide three primary ways of targeting the PNS by using myotubes as signal receiver/amplifiers that improves on current neural interface designs: 1) current understanding of cell-electrode contact suggests that the increased physical size and transmembrane current of myotubes will improve electrode sealing, 2) the bi-directional communication between myotubes and moto-neurons may promote growth of axon collaterals from the native PNS into the cultured probe and 3) current knowledge about neural information processing suggests that targeting the PNS for neural interface implantation will simplify the algorithms involved in decoding motor intention. Various embodiment myo-MEA designs stand to increase $R_{seal}$ between the cell and electrode, specifically targeting neural signals that are highly tuned to motor intention, and further target a portion of the nervous system where motor intention has already undergone cerebellar processing.

Ex vivo cell-based experimental systems used to study muscle cell contraction, and others based on incorporation of cells into sensitive force transducers or electrophysiology equipment, are time-consuming, invasive, and not universally available, slowing the pace of research. Video microscopy provides a noninvasive way to record the contractile behavior of skeletal muscle cells in vitro. In one aspect, a numerical procedure is disclosed, using a computer suitably programmed with image processing and pattern recognition algorithms, that makes it possible to quantify contractile behavior of multiple myotubes simultaneously, based on video data. The ability of one embodiment computer program to identify movement using a simplified graphical model of myotube contraction is dependent on the morphology and movement characteristics of the objects. However, the program performs optimally over the types of motions approximating those observed in culture and identifies contracting myotubes in sample videomicrographs of muscle cells in vitro. This program quantifies contractility on a population level, can be adapted for use in laboratories capable of digital video capture from a microscope, for example, and may be coupled with other experimental techniques to supplement existing research tools.

In one aspect a video-based device is provided to facilitate, for example, population-level studies of developing myotube functionality, termed the Visual Twitch Analysis (VTA) algorithm, which can be easily combined with other existing research tools. This code may be stored in the memory of a suitably configured computer, as known in the art, and executed by a processor in the computer to perform the steps indicated in the program, thereby providing the functionality of the VTA algorithm. The computer may include input/output hardware controllable by the processor, as known in the art, to receive video data from a video source, such as a video microscope of the like.

Video microscopy provides a noninvasive way to record the contractile behavior of skeletal muscle cells in vitro. Visual analysis of such data by hand, however, is confounded by the small and sporadic nature of spontaneous muscle cell contractions in vitro, by the difficulty of assigning some form of graded quantification to these events, and by the unavoidable introduction of bias, either through visual identification of contraction events or through hand selection of specific regions that are then passed to an automated analysis tool. Having a fully automated system to perform video analysis makes it possible to quantify large amounts of data in an unbiased way and with a high degree of reproducibility and flexibility.

Example

Cell Culture

Myoblasts were isolated, cultured, and imaged as previously described in the literature. Briefly, pregnant Sprague Dawley rats were sacrificed by $CO_2$ inhalation at gestational day 21, in accordance with Rutgers University animal care procedures. Pups were removed by Cesarean section, and hind limb muscles were removed to a separate container of Hanks' Balanced Salt Solution (Invitrogen, Carlsbad, Calif.)+1% HEPES Buffer (Mediatech, Inc., Herndon, Va.). Tissue was finely minced and brought to a final volume of 7 ml in PBS containing 1.5 U/ml collagenase (type D, Roche, Mannheim, Germany) and 2.5 U/ml dispase (type II, Roche, Mannheim, Germany). Tissue slurry was then incubated for 20 min at 37° C. and triturated using a pipette to break up remaining tissue clumps. Solid debris were allowed to settle for 15 minutes, and remaining cells were pelleted out of the supernatant by centrifugation.

The cell pellet was resuspended in growth medium comprising Ham's F-10 medium including 20% fetal bovine serum, 1% Penicillin/Streptomycin, (all from Invitrogen, Carlsbad, Calif.) and 2.5 ng/ml human b-FGF (Promega Corporation, Madison, Wis.). Cells were then plated into 75 cm$^2$ flasks and incubated for 24 hrs to allow for attachment of viable cells. Cultures were washed 3× with PBS to remove non-adherent cells and debris. Cells were then re-suspended and plated onto smooth or grooved PDMS surfaces at a density of 150,000 cells/cm$^2$ in differentiation medium comprising Neurobasal medium including 2% B27 Supplement, 1% Penicillin/Streptomycin and 1% GlutaMAX (all from Invitrogen, Carlsbad, Calif.). Prior to seeding, surfaces were coated with laminin (Sigma Aldritch, St. Louis) at 40 µg/ml.

In Vitro Video Capture & Synthetic Data Generation

Videos were acquired at day in vitro (DIV) 7-14, using an inverted microscope (Olympus, Center Valley, Pa.) with a SensiCam digital camera (PCO Imaging, Kelheim, Germany) and Image-Pro Plus image acquisition software (MediaCybernetics, Bethesda, Md.). Thirty second videos of myotube behavior were acquired over 200 frames using a 10× objective and 512×640 pixel resolution, recording an area of 0.55 mm$^2$. To create the standardized set of videos used for subsequent program validation, example videos were hand sorted into groups containing 0, 1, 2, 3, 4, or 5 contractile cells. The number of videos in each group are as follows; $N_{0-3}=5$, $N_4=3$, $N_5=2$.

Synthetic data were generated to correlate with the in vitro video data above. Bars were created by randomly generating the coordinates for two points in a viewing field of 512×640 pixels. These points were connected with a black line of varying width. The amplitude of bar movement was determined by randomly generating a horizontal and vertical deviation for each of the bar endpoints from a predetermined range. The frequency of oscillations was selected from a range of 0.0 to 13.3 Hz (or 0 to 400 times over the course of the movie). Movies were simulated for 200 frames, with a timing of 0.15 sec/frame, which was the maximum acquisition rate for an embodiment software/camera combination. Bar width and endpoint deviation were drawn from a distribution yielding the final behaviors indicated in Table 1.

Automated Data Analysis

An embodiment VTA program involves an automated three part process, shown in FIG. 1: 1) image processing and data extraction, 2) generating sets of possible myotube conformations that explain the data, and 3) selecting the best set of myotube conformations. Blocks in FIG. 4 indicate individual processing steps (rectangles) or decision points at which irrelevant data can be discarded (diamonds). Arrows indicate the inputs of experiment-derived data (black arrows) or external parameters (gray arrows) to each processing sub-step to the next. The algorithm is conceptually broken into three fundamental steps (black dashed lines) discussed in the following. Portions are run iteratively (gray dashed boxes) to improve accuracy.

In the first step, the VTA program breaks each frame of the video into multiple regions and compares it to the initial frame. This generates a measure of how local pixel intensity changes as a function of time. These changes can be caused by myotube contractions or by culture artifacts, such as changes in lighting and floating debris. In the second step, these time-variant functions are used to identify contractile regions of the video. In the third step, these regions are judged for "fitness" in explaining the data. Because the process may be partially dependent on several parameters used in the image processing and fitness testing steps, this process can be repeated several times and averaged to yield the final estimate of the number and location of cells (see Discussion section for description of how parameter values affect program performance).

In FIG. 2, (A) shows a full image of the viewing field; in this case containing multiple independently active myotubes, at t=0 s (red stars). Selected areas (red boxes) are magnified and shown at separate time points in B and C, respectively. (B) and (C) show magnified image of the area boxed and labeled in A. B.1 and C.1 show these regions at t=0 s; noteworthy features (white arrowheads) are noted for comparison with later time points. Myotube movement is apparent from the displacement of these features in B.2 and C.2 from their initial positions (again indicated by white arrowheads) to their position at maximum deflection some time later (red arrowheads). (D) shows example output from the embodiment VTA program, demarcating the areas covered by the 3 active cells. (E) shows the δK(t) function for each of the 3 cells plotted over time. Individual contractile events are visualized as the peaks occurring semi-rythmically throughout. (F) shows the correlation of each δXY(t) function with the δK(t) functions shown in E. Activity is clearly correlated in regions associated with particular cells.

In the first part, a series of image processing steps transform the video into a collection of time-variant functions representing the extent to which a given region in the image has deviated from its initial position over the course of the movie. The first step is to threshold each frame of the video to turn it into a black and white image. Pixels with a value above the binarization threshold ($T_B$) are assigned a value of 1 while all others are 0. Next, each image is divided into an N×N grid. Each block of the grid is treated as its own interrogation window ($W_{XY}$), where the capital subscripts X and Y refer to the block's location in the N×N grid. For each $W_{XY}$, the quantity of binarized pixels ($P_{xy}$), which switch values (i.e., from 1→0 or from 0→1) as compared to first frame in the video (t=0), are summed over x and y, where the subscripts lower-case x and y indicate the position of each pixel within its interrogation window ($W_{XY}$) (FIG. 2(B-C)). This is repeated for each subsequent frame (t=1, 2, ... n), generating a time-variant indicator of deviation from the starting point for each $W_{XY}$ (referred to as $E_{XY}(t)$). This is repeated for all $W_{XY}$, according to Eq. 1:

$$E_{XY}(t) = \Sigma_x \Sigma_y |(P_{xy}(0) - P_{xy}(t))| \quad (1)$$

Significant change from the initial position in a particular $E_{XY}$ may indicate contractile activity in the corresponding window. $W_{XY}$ windows that contain $E_{XY}(t)$ peak values above the product of the "spike threshold" value ($T_S$) and the standard deviation of the $E_{XY}(t)$ function are assumed to include contractile information, while those without peaks over this level are excluded from further analyses. Inclusion criteria for further analysis are expressed in Eq. 2:

$$\text{MAX}(E_{XY}) \geq T_S \times \text{STD}(E_{XY}) \quad (2)$$

Videos containing fewer than a threshold number ($T_N$) of windows demonstrating contractility are classified as containing no contractile cells. Finally, the remaining $E_{XY}(t)$ functions are each normalized to themselves, to yield the "delta function" ($\delta_{XY}(t)$). The $\delta_{XY}(t)$ functions are therefore essentially a unit-less measure of displacement as a function of time, which allows the rest of the algorithm to identify portions of the images that move synchronously. $\delta_{XY}(t)$ is calculated according to Eq. 3:

$$\delta_{XY}(t) = \frac{E_{XY}(t)}{\text{MAX}(E_{XY})} \quad (3)$$

In the second stage, the Jade algorithm [90] is used to perform independent component analysis (ICA) on the $\delta_{XY}(t)$ functions. ICA is a computational technique used to recover original independent data streams when the data are sampled on multiple recording devices, each of which records a different linear mixture of the original data. An example is recording two people speaking at a cocktail party from microphones placed at four arbitrary locations around the room (the "cocktail party problem"). ICA is ideally suited to regenerate the original sound information of each speaker based on the recordings from the four microphones, each of which records a different mixture of both speakers based on its location relative to the two signal sources. In its most basic form, the ICA algorithm can be instructed of the number of original signal sources it is meant to identify. Further explanation of the algorithms used to perform ICA has been discussed extensively by other groups.

Performing ICA on the $\delta_{XY}(t)$ functions returns new time-variant functions in the form of K separated data streams (termed $\delta_K(t)$), where K is the number of signals the ICA algorithm was instructed to extract. These $\delta_K(t)$ functions represent the presumed activity of the contractile myotubes, which have been recorded in a mixed fashion in the $\delta_{XY}(t)$ functions (FIG. 2(D)). The $\delta_{XY}(t)$ functions act like an array of $N^2$ microphones, recording contractile activity from K independent myotubes, which are like the cocktail party guests in the example above. This is performed iteratively for K=1, 2, ... K, generating K possible prospective myotube sets. After each iteration, the results are analyzed in the third stage of our algorithm, and judged for overall fitness.

The third stage is concerned with determining which of the myotube sets generated in the second stage most closely resemble the natural behavior of myotubes while explaining the observed data. The first step in this process is to exclude $\delta_K(t)$ functions that are obviously not generated by myotubes. This is accomplished by grouping $W_{XY}$ windows into clusters based on the correlation coefficient of their respective $\delta_{XY}(t)$ functions with each $\delta_K(t)$ function (FIG. 2(E1-3)). Any window ($W_{XY}$) is included in cluster K according to the inclusion criteria in Eq. 4:

$$\text{corrcoef}(\delta_K(t), \delta_{XY}(t)) \geq T_R \quad (4)$$

where $T_R$ is the correlation threshold. At this point, the center of $W_{XY}$ becomes a "node" for the purposes of identifying myotube location. All nodes within a cluster are then joined according to the Delaunay triangulation. Edges over a certain length ($T_L$) are then eliminated, leaving an arbitrarily shaped graph denoting the location of a likely contractile body (FIG. 2(F)). The area of the resulting compound polygon is taken to be the estimated area of that prospective myotube ($A_J$). This process allows generation of a two-dimensional map of each prospective myotube in a set based on correlation of each $\delta_{XY}(t)$ function with the set of $\delta_K(t)$ functions.

Clusters are then screened for validity based on morphological characteristics, and clusters that are unlikely to be real myotubes are eliminated. For example, clusters covering more than a threshold percentage ($T_A$) of the viewing area are more likely to be lighting artifacts than they are to be myotube contractions. Similarly, clusters composed of a smaller number of triangular sections than a threshold number ($T_T$) are more likely to be floating debris than contracting myotubes. If a cluster does not pass both of these criteria, the corresponding $\delta_K(t)$ function is excluded from further analyses. While excluded $\delta_K(t)$ functions are not counted in further analysis, their initial inclusion is desirable because it provides the program with the opportunity to identify artifacts in the video and isolate their effect from the relevant data.

The remaining $W_{XY}$ clusters are then used to measure the overall fitness for a given set of $\delta_K(t)$ functions. These measurements take the form of "success" and "failure" metrics, calculated from the geometry of the nodes in each cluster and the behavior of the $\delta_{XY}(t)$ functions, meant to identify how well the $W_{XY}$ cluster explains the video data all within the context of looking for contractile myotubes. There are three success metrics, "Success Spread" ($S_1$), "Area Coverage" ($S_2$), and "Cell Number" ($S_3$), as well as three failure metrics, "Correlation Difference" ($F_1$), "Scatter" ($F_2$), and "Missed Twitch" ($F_3$) (see the appendix below for an expanded explanation of how success and failure metrics are calculated).

Each of these success and failure metrics is normalized to itself, creating a range of values between 1 and 0 for each of the cluster sets. They are then used to create a vector within the unit cube representing the total success and total failure of the cluster set (FIG. 3(A-B)). The magnitude of the failure vector is then subtracted from the magnitude of the success vector to assign a final score to the cluster set called the "Net Success" score ($S_N$), according to Eq. 5 (FIG. 3(C)):

$$S_N = (S_1^2 + S_2^2 + S_3^2)^{1/2} - (F_1^2 + F_2^2 + F_3^2)^{1/2} \quad (5)$$

The set with the greatest net success score is considered the winner, and the number and location of the $W_{XY}$ clusters is taken to be the number and location of contractile cells in the video (FIG. 3(C), blue bar).

As indicated, FIG. 3 provides illustrative data from the video pictured in FIG. 2 (K=10). (A-B) indicate the total success vector and failure vector, respectively, represented in their own unit cubes. Each cluster set receives a score on all three success metrics and all three failure metrics, defining a spot in "success space" and "failure space" (gray circles sequentially labeled 1-10). The distance from this point to the origin is the magnitude of the success and failure vectors (black lines). The highest success score and lowest failure score are indicated in the figure (red lines). The "shadow" of each point is projected on the 3 planes created by the 3 axes.

FIG. 3(C) shows the net success score shown for each cluster set examined. The height of the bar above the x-axis represents the length of the success vector. From this amount, the length of the failure vector is subtracted (red bars), leaving either residual positive net successes (gray bars), or a negative net success score. The cluster set with the highest residual net success score is considered the "winner" (blue bars). Values for the parameters used in this analysis are indicated to the right.

Because several of the steps indicated involve external parameters, specifically all of the thresholding steps, the result of an embodiment VTA analysis is sensitive to the values selected for these parameters (FIG. 1, gray arrows). For this reason, an embodiment analysis is performed several times for each video, and the parameters are drawn randomly from an appropriate range at the beginning of each trial (FIG. 1, gray dashed boxes). For additional information on the VTA algorithm (including MATLAB code and parameter values), see the appendix below.

The VTA program was used to identify the number of contractile myotubes in the standardized in vitro video data set 1 in Table 1. The algorithm generated three cell number guesses for each video of each group. All the guesses generated for a given group were then averaged together to provide the VTA estimate of that group's average number of cells per video. This estimate can be easily compared against the number of cells actually present in each video for that group as a means of gauging program performance.

TABLE 1

Description of synthetic and in vitro data sets

| Set: | # of Bars: | Task: | Behavioral Range: |
|---|---|---|---|
| 1 | 0-5 (Cells) | Identify the average number of contractile myotubes in groups of videos hand-selected to contain 0, 1, 2, 3, 4, or 5 myotubes. | As observed in vitro |
| 2 | 1 (200 videos) | Identify a single moving bar over a range of behaviors exceeding the program's detection ability. | Frequency = 0.0-13.3 Hz Footprint = 0.0-0.30 mm² Oscillation Area = 0.0-0.23 mm² |
| 3 | 1 (200 videos) | Identify a single moving bar over a range of behaviors simulating biological data. | Frequency = 0.0-1.0 Hz Footprint = 0.0-0.06 mm² Oscillation Area = 0.0-0.03 mm² |
| 4 | 0-10 (200 | Identify multiple randomly placed, | Frequency = 0.0-1.0 Hz Footprint= 0.0-0.06 mm² |

TABLE 1-continued

Description of synthetic and in vitro data sets

| Set: | # of Bars: | Task: | Behavioral Range: |
|---|---|---|---|
| | videos) | and potentially overlapping bars. | Oscillation Area = 0.0-0.03 mm$^2$ |
| 5 | 0-10 (200 videos) | Identify multiple randomly placed, and non-overlapping bars. | Frequency = 0.0-1.0 Hz Footprint = 0.0-0.06 mm$^2$ Oscillation Area = 0.0-0.03 mm$^2$ |

In order to examine the performance envelope of the VTA program in situations atypical of those observed in an embodiment culture system, analysis of computer-generated data sets (synthetic data) was performed. Videos included of an oscillating black bar against a white field, meant to simulate the most basic movement of myocytes seen in video micrograph recordings. Bars of varying dimensions, orientations, and activity levels (frequency and amplitude) were simulated. Parameters determining the behaviors of the synthetic myotubes were randomly selected for each video from a pre-defined range. Five sets of videos were analyzed, as described in Table 1.

Two metrics are used to measure VTA program performance: 1) number estimate error ($N_E$), and 2) area estimate error ($A_E$). The number estimate error is calculated as the difference between the number of bars identified by the program ($N_I$) and the true number of bars in the video ($N_T$), as in Eq. 6. Area estimate error is calculated as the difference between the contractile area identified by the VTA program ($A_I$) and the true area over which a bar moves during its oscillation ($A_T$), as in Eq. 7:

$$N_E = N_I - N_T \quad (6)$$

$$A_E = A_I - A_T \quad (7)$$

These error metrics are measured against features of the videos in the synthetic data sets, such as oscillation frequency, bar footprint, oscillation area, and number of bars present. The bar footprint is defined as the area covered by the stationary bar. Oscillation area is defined as the area through which the bar oscillates minus the bar footprint, allowing for the quantification of completely arbitrary bar movements. All synthetic data were generated and analyzed in MATLAB (The MathWorks, Natick, Mass.).

Analysis of In Vitro Video Data

Rather than creating additional synthetic data, which included artificially generated noise artifact as a means of testing the algorithm's robustness to biological and culture noise, the VTA algorithm was instead used to analyze a standardized set of videos, data set 1 in Table 1. FIG. 4(A) shows the average number of contractile cells per video identified for 6 groups of videos, containing 0, 1, 2, 3, 4 and 5 contractile cells, respectively. The embodiment VTA algorithm is sensitive enough that it identifies an average of 1.58 cells per video in the group where no contractile cells are present. In these cases, the algorithm incorrectly identifies lighting artifact and vibrational noise as contractile motion. This same inclusion error is repeated in each group, resulting in identified cell numbers of 2.60, 3.80, 4.27, 5.11, 5.83 for the other 5 groups (an average overestimation of 1.37 cells in each case). However, at this level of sensitivity, the algorithm is clearly able to provide an indication of the different activity levels in each group relative to other groups, differing by even a single contractile myotube.

Single Object Identification

The embodiment program's ability to identify a single bar was examined over two ranges of parameter values as described in Table 1 (data sets 2 and 3). Over the range of bar footprints, a noticeable decline in the area estimate error begins after 0.065 mm$^2$, after which each step results in a noticeable worsening of the area estimate error (FIG. 4(B)). Prior to this crossing point, the program overestimated the area by 0.01 mm$^2$, while after the crossing point, it underestimates the area of coverage by an average of 0.08 mm$^2$. Also noticeable is the program's failure to detect bars with a footprint below 0.0004 mm$^2$, consistent with the VTA algorithm excluding signal sources below a minimum size.

FIG. 4(A) shows embodiment VTA performance on standardized in vitro data. Program performance at single bar identification vs. bar footprint is shown in 7(B), and oscillation area in 4(C), respectively, examined over the range of behavioral characteristics described in Table 1. The Number Estimate Error is displayed (blue lines and left y-axis), as well as the Area Estimate Error (red lines and right y-axis). For comparison, these graphs also show the range of behaviors observed in cell culture (shaded area). (D) The Number Estimate Error as a function of bar number. (E) The Area Estimate Error as a function of bar number. Results at multiple object identification are shown for overlapping bar (solid line) and non-overlapping bar (dashed line) data sets as described in Table 1. Error bars represent the standard error of the mean.

Both the number estimate error and the area estimate error are sensitive to the oscillation area (FIG. 4(C)). Similar to the trend observed with the increasing footprint size, there is a marked falling off in the accuracy of the area prediction past 0.07 mm$^2$. Prior to 0.07 mm$^2$, the program performs well, underestimating the area by only 0.004 mm$^2$, while after that point, this number increases to 0.05 mm$^2$. The number error is even more sensitive to the oscillation area, beginning a steep increase in the number estimate error at 0.01 mm$^2$. Between 0.01 mm$^2$ and 0.08 mm$^2$, there is a marked increase in the number estimate error with each step before this error metric plateaus.

Despite sensitivity of some performance measures to the extreme value of footprint and oscillation area, the program performs consistently at the single bar identification task over the range of behaviors meant to mimic culture behaviors in vitro, discussed in data set 3 in Table 1 (FIG. 4(A-C, gray shading)). In analysis of synthetic data set 3 (data not shown), the embodiment VTA program overestimated the number of bars present by only 0.62. Over this same range of parameter values, the program performs similarly well at the area-identification task, overestimating the area by an average of 0.007 mm$^2$.

Multiple Object Identification

Analysis was run on synthetic data sets 4 and 5, as described in Table 1. In both cases, the cell count estimate error stays low until some threshold is reached. When the overlapping bar data set is analyzed, the program can successfully classify videos containing up to 6 bars without overestimating or underestimating the number of bars by more than 1. When the non-overlapping data set is analyzed, by comparison, the program maintains a similar level of accuracy (overestimating or underestimating by less than 1) until more than 8 bars are present. However, program performance on both the overlapping and non-overlapping data sets drops off steeply past 6 and 8 bars, respectively, decreasing almost linearly with the number of bars past that point (FIG. 7(D)). In comparison, the area estimate error does not change past 6 bars with the exception that it starts to underestimate the contractile area. The magnitude of the area estimate error remains consistently low, however, even though the sign is reversed (FIG. 4(E)).

Analysis of Example Video Micrographs

To expose the program to a wide range of behaviors, analysis was performed on several example videos taken under multiple culture conditions. Conditions included growth on a smooth substrate to encourage the formation of syncitial networks (FIG. 5(A)) and on a grooved substrate to encourage the formation of independent and aligned myotubes (FIG. 1(B)).

FIG. 5(A) shows syncitial network of contractile myotubes grown on a smooth surface (single red star). FIG. 5(B) shows contractile myotubes (red stars) grown on surfaces modified with 100 μm grooves (red bars). FIG. 5(C-D) shows locations of contractile cells identified by the embodiment VTA program from the videomicrographs shown in 5(A) and 5(B), respectively. FIG. 5(E-F) are histograms of the embodiment VTA estimated number of cells in each video (blue bars), relative to the actual number of cells (vertical red line). The mean, median, and mode of the estimates are also shown in each case. FIG. 5(G) shows single bar misclassification by identifying one or both of the edges as multiple bars. FIG. 5(H) shows two mostly overlapping bars identified as the same object (yellow hatch work). FIG. 5(I) shows the omission of the center area of the bar resulting in underestimation of area coverage.

Inspection revealed the network shown in FIG. 5(A) was electrically coupled and contracted as a single network. The program was able to identify the network as a single contractile entity in 10 out of 10 trials (FIG. 5(E)). FIG. 5(B) shows myotubes cultured in 100 μm wide grooves which are 35 μm deep. Culturing the cells on the grooves resulted in the alignment of the myotubes and prevented myotubes in neighboring grooves from touching one another and forming networks. As a result, the myotubes contract independently of one another. Visual inspection revealed that this video contained four independent myotubes, one in each of two trenches and two located in the same trench (FIG. 5(B), red stars). These myotubes are successfully identified and localized by the embodiment VTA program, which identified four cells in nine out of ten trials, with an average estimate of 3.9 cells (FIG. 5(F)).

Conclusion:

The result is a novel technique for quantifying functional population-level behaviors of myotubes and a generalizable blueprint for algorithm development in a wide range of other potential applications. The technique described herein expands on the utility of preexisting methods by fully automating the process of data extraction and increasing applicability in a wider variety of experimental situations.

Ultimately, the optimal values for many of the parameters used in the VTA algorithm are related to the apparatus used to acquire the video data. Tuning of the parameters is within the skill of an ordinary practitioner or user. Different set-ups may have very different optical qualities, including different levels of contrast, magnifications, frame acquisition rate and pixel spatial resolution, which would change the appearance of myotubes within the video. All of these changes would therefore change the optimal thresholding values. The parameter values used in this study were tuned experimentally, using a procedure where the embodiment VTA program output was compared to by-hand analysis for a small sub-set of randomly selected videos, and parameters were tuned to minimize the difference. Parameter values selected using this process were then applied in the analysis of all videos. Hence, use of an embodiment VTA algorithm on other sets of data may require application-specific fine-tuning. Furthermore, while units are used on the scale of single $mm^2$ and Hz because they are relevant to the size and activity levels of our subject in this study, skeletal myotubes, these units may be altered depending on the capabilities of individual recording equipment and subject.

Other Embodiments

Embodiment programs fill a gap in researchers' ability to monitor muscle cell function. The image processing steps successfully generate trackable features from video data, and the success and failure metrics are flexible enough to exclude extraneous information, such as changing lighting conditions or floating debris, while capturing a wide range of myotube morphologies and activities. It provides a way of looking at contractility on a population level, rather than in individual cells, and may be performed in most laboratories. Additionally, it is non-invasive and can be performed at multiple time points on the same culture or even on the same group of cells within a culture. The flexibility of this new analytical tool allows its use in a way that supplements the other biochemical, morphological, and kinetic techniques currently employed.

Additional gains may be made by incorporating a controlled lab-on-a-chip device into the design. The integration of substrate-based, microfabricated sensor arrays with the described optical technique provides new and sensitive dual-modality sensing arrays. For example the application of the VTA algorithm to myotubes grown on an arrays of micropillars meant to accommodate and quantify cell contractility would generate a sensitive mechanism to detect force generation in populations of myotubes. Another useful combination is the application of the VTA algorithm to cells grown on, or immobilized on, micro-electrode arrays (MEAS), which provides a sensitive way to quantify the correlation between excitation and contraction in populations of single cells. Additionally the use of the VTA algorithm in conjunction with MEA technology enables the incorporation of a contraction triggering mechanism, eliminating the dependence of many procedures on spontaneous activity.

Automated Sholl Analysis of Digitized Neuronal Morphology at Multiple Scales

Neuronal morphology is important for determining how action potentials propagate, how information is processed and neuronal function. Neurite branching affects how single neurons integrate synaptic inputs and how they communicate as networks. Alterations in neuronal morphology and branching patterns have been observed in a wide range of developmental or acquired disorders in which it is thought that altered arbor structure plays a role in the pathogenesis of the disorder. Understanding the factors affecting neuronal morphology is, therefore, integral to understanding nervous system health and disease.

Neuronal morphology is a complex phenomenon to study due to the wide range of metrics which may be quantified. The present invention provides a unique tool that incorporates two existing morphological analysis platforms, along with custom analytical components, to provide detailed neurite-level morphological data. The program incorporates NeuronJ to acquire spatial information about the position of neuritic segments in space relative to the rest of the cell (FIG. 6(B)). It then exports this information to NeuronStudio to allow the user to define structural information about the connectivity between neurites (FIG. 6(C)). The program then assigns "identities" to each neuritic segment according to its location within an arbor. Assigning an identity to each segment allows the program to perform a series of analyses relating morphological metrics to segmental identity (FIG. 7). The workflow created is intended to streamline data digitization and storage processes while preserving the reliability of user control.

An embodiment program's ability to detect changes in arbor morphology is validated by applying this analysis to neurons incubated with BDNF, a well-studied extracellular factor that regulates neurite morphology.

Example

Cell Culture & Imaging

Hippocampal neurons were isolated from E18 rat embryos and cultured. Briefly, embryos were removed by Cesarian section at 18 days gestation and decapitated. The hippocampi were manually dissected under a microscope, and cells were triturated with a fire polished glass pipette tip, counted on a hemocytometer, and plated at a density of ~1800 cells per $mm^2$ on 35 mm petri plates (Corning) coated with 1 mg/ml poly-D-lysine (Sigma-Aldrich). Cultures were maintained in Neurobasal medium containing penicillin, streptomycin, glutamine, and B27 supplement (NB; all purchased from Invitrogen).

At 5 days in vitro (DIV5), cells were transfected with cDNA encoding GFP using Effectene (Qiagen). The low efficiency of this transfection technique in this cell system allows the easy identification of the processes associated with single neurons. In the BDNF treatment groups, treatment occurred from DIV7-10, during which regular NB was replaced with NB containing 25 ng/ml BDNF. This BDNF concentration does not stimulate p75 or other Trk (A and C) receptors. Cultures were fixed in 4% paraformaldehyde on DIV10 and immunostained with rat anti-GFP (a gift from Dr. Shu-Chan Hsu, Rutgers University) and MAP-2 (Sigma-Aldrich). Neurons were imaged in the GFP channel at 200× using an Olympus Optical IX50 microscope with a Cooke Sensicam CCD cooled camera, fluorescence imaging system, and ImagePro software (MediaCybernetics). Images were acquired in 8-bit TIFF format, measuring 512×640 pixels.

Program Mechanics & Usage

Figure 6:
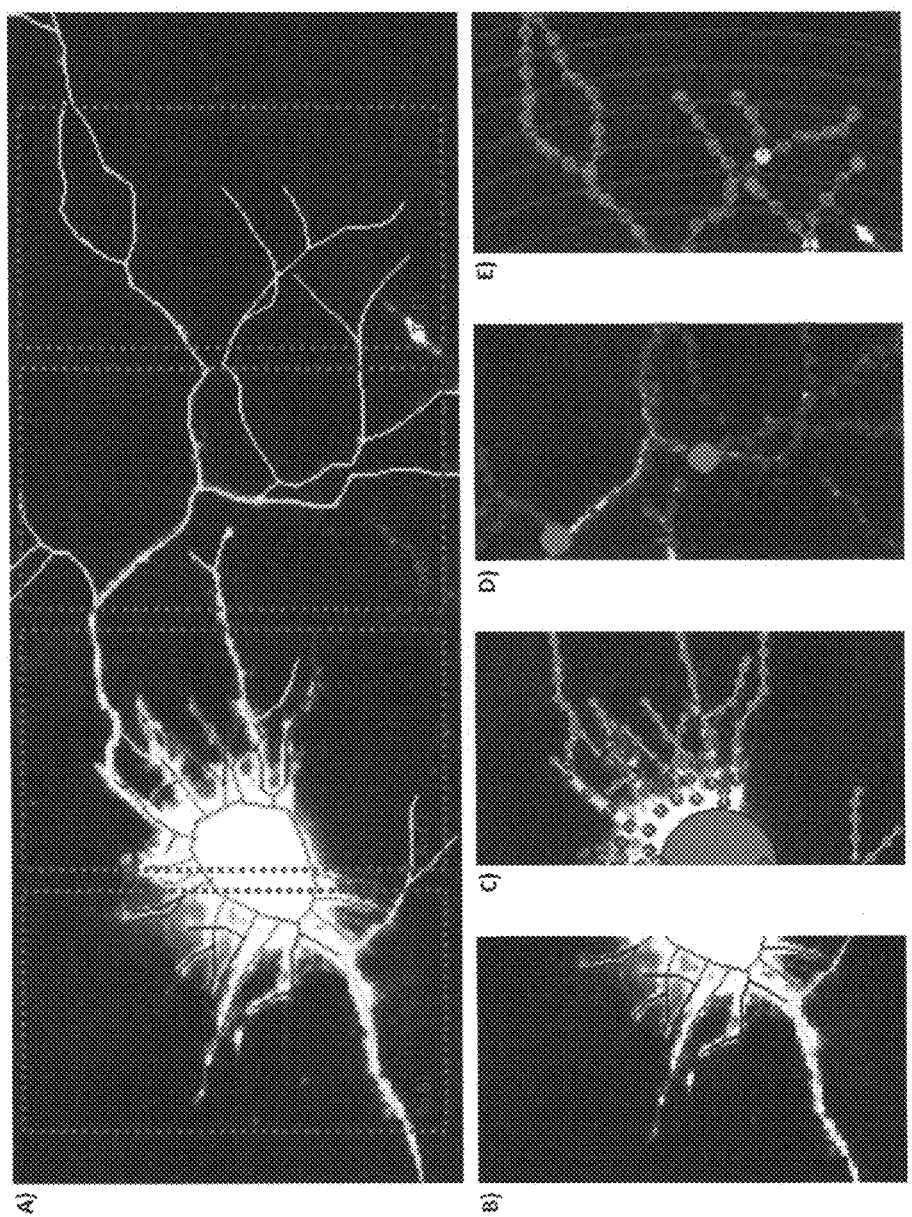
FIG. 6 is a schematic of digitization and analysis process available through an embodiment program.
Figure 7:
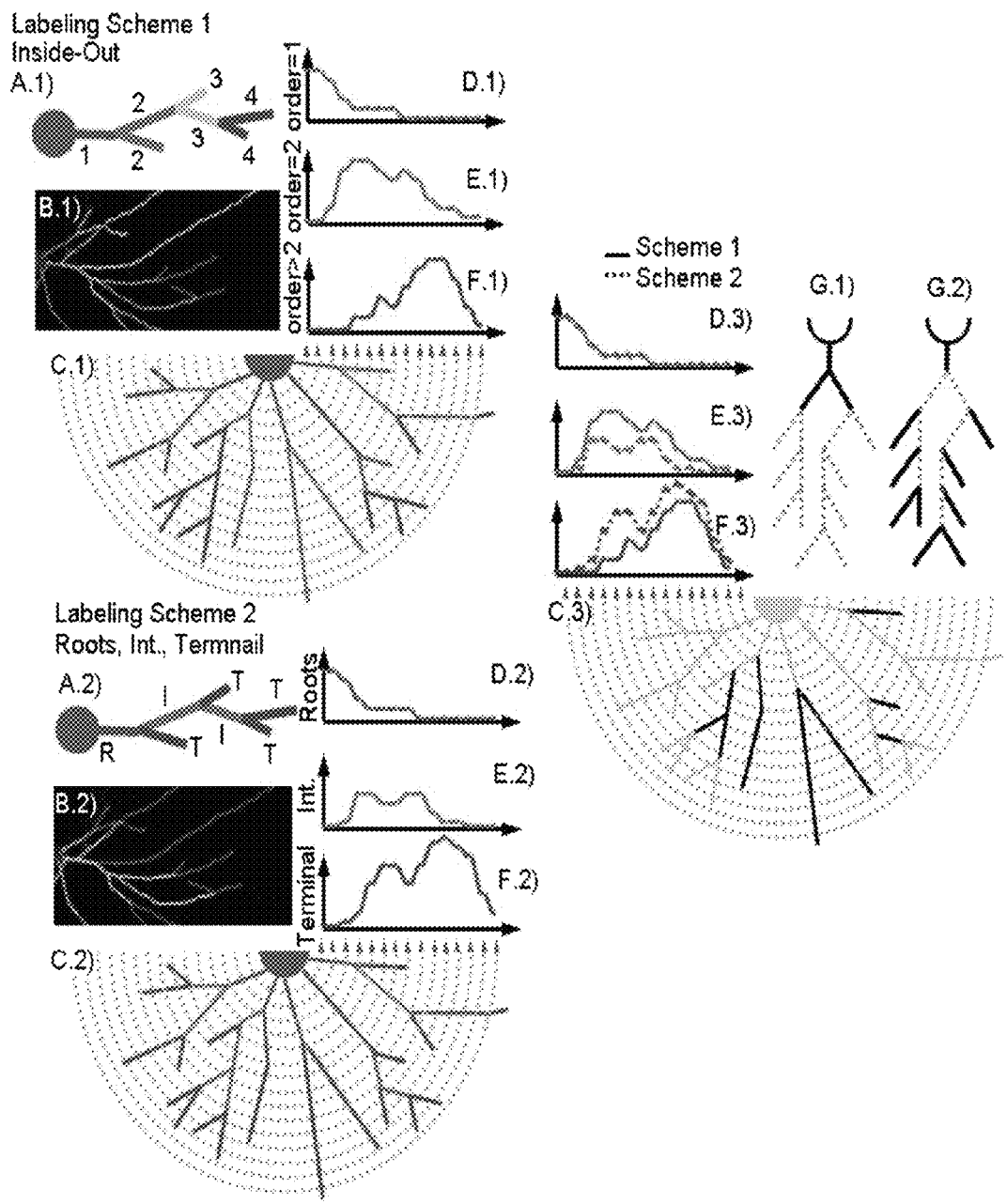
FIG. 7 shows two structure-dependent labeling schemes that assign an identity to neurite segments based on their location within their arbors.

FIG. 6(A) shows a neuron that has been "skeletonized" as a first step in digitizing its structure. FIG. 6(B-E) shows example graphical output of each step of the Bonfire procedure, as applied to segments of the image shown in FIG. 6(A). Example non-linkage errors FIG. 6(D), red spots, have been left in the figure intentionally to demonstrate embodiment Bonfire program error identification. Each step is performed on the entire neuron, but are shown in panels to emphasize the sequence in which they occur.

An embodiment Bonfire program is a series of custom scripts written in, for example, MATLAB (MathWorks), although it will be appreciated that any suitable programming language may be employed. Neuronal morphology was digitized in three stages based on the initial images. In the first stage, the semi-automated tools available through the NeuronJ plugin to ImageJ (NIH, Bethesda Md.) were used to define all neurite positions (FIG. 6(A-B)). The data for each neurite are exported using NeuronJ in the form of a series of nodes with defined positions in the X-Y plane, where nodes belonging to an individual neurite segment are linked by association. These tools allow the user to guide the tracing of each neuritic segment with course resolution by hand but reduce tracing time by using a curve-fitting algorithm to fine-tune the exact location of the nodes defining the neurite position.

In the second stage, portions of the embodiment Bonfire program were used to convert the strings of nodes provided by NeuronJ into SWC format for further manipulation. NeuronStudio is then used to define the pattern of connectivity between neurite segments (FIG. 6(C)). The transformation of the data into SWC format allows for the linkage of the simple strings of nodes defined previously into more complex branching structures. After linking is complete, another component of the embodiment Bonfire program checks the resulting structure for errors and non-linkages (FIG. 6(D)), based on the assumption that each neuritic segment may only give rise to two or less daughter segments. This assumption is made to facilitate future integration with theoretical growth models and does not result in significant loss of data. These two steps fully determine the structure of each cell's neuritic arbor in 2-dimensional space and encode it in a digital format.

Using these digitized neuritic arbors, a second component of the embodiment Bonfire program was then used to perform process identification and extract the following metrics: number of primary neurites, number of secondary neurites, number of branch points per cell, number of terminal neurite tips per cell, and Sholl analysis performed with a 3.0 µm ring interval (FIG. 6(E)). Sholl analysis is performed conceptually by drawing concentric circles around a cell body at incrementally increasing radii and counting the number of times each circle crosses a neuritic segment. The number of intersections is graphed as a function of radial distance from the cell body to give a quantitative representation of how neurite density varies spatially.

Because the location and linkage pattern of neurites is user-defined using external tools, the algorithms associated with data extraction are geometric in nature and do not depend on conceptually complex image analysis. For example, the algorithm for Sholl analysis is based on the assumption that if a neuritic segment starting at one node (node $N_n$ with Cartesian coordinates $X_n, Y_n$) lies inside of a somacentric circle with radius r ($C_r$), and its daughter node (node $N_{n+1}$ with Cartesian coordinates with coordinates $X_{n+1}$, $Y_{n+1}$) lies outside of radius r, then that neurite must cross the circle with radius r. $C_r$ is also intersected by this neuritic segment if the reverse is true. Therefore, $C_r$ is intersected by a neuritic segment when the criteria outlined in Equation 1 are met, as follows:

$$[(\sqrt{X_n^2+Y_n^2}<r) \cup (\sqrt{X_{n+1}^2+Y_{n+1}^2}\geq r)] \cap [(\sqrt{X_n^2+Y_n^2}\geq r) \cup (\sqrt{X_{n+1}^2+Y_{n+1}^2}<r)] \quad \text{Eq. 1}$$

The above holds true regardless of the spacing between nodes defining a neurite path, and so can be used for all mother-daughter node pairs. To return the cumulative Sholl curve, this same check is performed between every mother-daughter node pair and every circle, and the results are summed by circle. Because every node is checked for the existence of a mother node, this reliably returns the Sholl information for the entire arbor. Furthermore, because every node-pair can be tagged with a structure-based identity, it is possible to later tabulate which identity-classes intersect with specific circles. Additional descriptions of the algorithms involved in data management can be found as comments in the MATLAB code disclosed below. Afterward, data were transferred to Excel to facilitate statistical analysis. The experimenter was blinded to experimental conditions during all data analysis.

Branch Identity-specific Data Analysis

FIG. 7(A) shows randomly generated arbor, labeled according to the "Inside-out" scheme (I/O-A.1) or the "Roots, Intermediate, Terminal" scheme (RIT-A.2) and color-coded according to order. FIG. 7(B) shows an example neuritic arbor, which has been digitized and color-coded according to branch order using I/O labeling (B.1) and RIT labeling (B.2), respectively. FIG. 7(C) is a schematized example neuritic arbor, color-coded according to I/O labeling (C.1) and RIT labeling (C.2), respectively, with superimposed Sholl rings. FIGS. 7(D-F) shows the order-specific Sholl curves resulting from the arbors shown in FIG. 6(C). FIG. 7(C.3) is an example arbor in gray, showing neuritic segments that change groupings between the two labeling schemes (black), accompanied by a schematic showing the relative areas of emphasis for the I/O FIG. 7 (G.1) and RIT FIG. 7(G.2) labeling schemes.

Two labeling schemes were used to assign structure-based identity to segments, to allow analysis of subregions of the arbor with varying degrees of specificity. Neuritic segments, or branches, are the uninterrupted stretches of neurite starting at one branch point, or starting at the cell body in the case of root segments, and ending when the neurite terminates or at the next branch point. These segments can be grouped together in different ways. In the most frequently used convention, these processes are assigned a number, or branch order. In this convention, termed "inside-out" labeling (I/O) here, branch order starts at 1 with any branch initiating at the soma and increases by 1 with each branch point reached, moving from the soma to the branch tips (FIG. 7(A.1-F.1)). The second convention is the "roots, intermediate, terminal" (RIT) convention (FIG. 11(A.2-F.2)), in which any neurite originating in the soma is a root segment, any neurite with no daughter neurites is a terminal segment, and any neurite not a root or a terminal is an intermediate segment.

Having neurites assigned segmental identities in I/O and RIT labeling allows the performance of more traditional forms of analysis on specific subregions of the arbor. For example, FIG. 7(A.1-F.1) shows Sholl analysis performed on neurite segments that have been consolidated into three separate groups based on their structural identity, resulting in three separate Sholl curves for the same cell. This technique is performed the same way as standard Sholl analysis but uses three possible groupings of segments. In the example shown in FIG. 7, the first grouping contains only primary segments, and therefore, only the intersections of primary segments with the Sholl rings are tallied in the generation of the Sholl curve for that group (FIG. 7 (D.1)). In the second group, only secondary processes are counted, and in the third group, all segments with order ≥3 are counted, generating the Sholl curves shown in FIG. 7(E.1-F.1), respectively. A similar analysis can be performed using the RIT labeling scheme in which only the Sholl intersections with root segments (FIG. 7(D.2)), intermediate segments (FIG. 7(E.2)), or terminal segments (FIG. 7 (F.2)) are counted. Note that the sum of all the component Sholl curves adds up to the total Sholl curve for the cell, and therefore, is the same in both of these cases.

Results:

FIG. 8(A) shows the total Sholl curves with example inverted GFP images (inset). FIG. 8(B) shows the average number of primary and secondary processes per cell. FIG. 8(C) shows the average number of branch points and terminal points per cell. FIGS. 8(D-F) show segment identity-specific Sholl analysis according to the I/O labeling scheme, where segments have been grouped as either primary (D), secondary (E), or tertiary and greater (F). FIGS. 8(G-I) shows segment identity-specific Sholl analysis according to the RIT labeling scheme, where segments have been grouped as either root segments (G), intermediate segments (H), or terminal segments (I). All error bars represent the standard error of the mean (SEM). Statistical analysis of dendrite number was performed on the total number of Sholl intersections in the bracketed regions using two-tailed unpaired t test with Welch correction (n=18 for 0 ng/ml BDNF condition, n=24 for 25 ng/ml condition).

Global Analysis:

Global exposure to BDNF in vitro increases proximal neurites within the first 35 μm of the soma but has no effect on distal neurites (FIG. 8(A)). Quantification of the number of primary and secondary neurites shows that BNDF treatment causes a statistically significant increase in the number of primary extensions, and while there is a trend of an increasing number of secondary neurites it does not reach statistical significance (FIG. 8(B)). In addition, the effect of global BDNF administration on the average number of branch points and number of terminal branches per cell (FIG. 8(C)) was analyzed, which showed no change between conditions. Similarly, global BDNF exposure causes no significant change in average process length or total arbor length (data not shown). While the specifics of BDNF treatment vary based on the type of neuron and system (in vitro vs. in vivo), these results are broadly consistent with the general scientific consensus that BDNF treatment increases arbor "complexity."

Local Analysis:

A more detailed picture of BDNF-induced morphological changes is created by the local-level Sholl analysis. RIT-based Sholl analysis identifies that the increased number of proximal Sholl intersections is due to two effects: 1) there is an increase in the number of primary neurites (FIG. 8(B)), which causes an increase in the number of Sholl intersections with primary neurites (FIG. 8(D) and G)), and 2) there is an increase in the number of Sholl intersections with terminal neurites (FIG. 8(I)). However, when the I/O labeling scheme is used (FIG. 8(D-F)), only primary neurites appear to change significantly between conditions. This is because the neurite sub-type responsible for much of the change (terminal neurites) is split between the second two classifications using the I/O labeling scheme, making a statistically significant change impossible to detect. Taken together, these two schemes indicate that the increase in proximal Sholl intersections is caused by increased primary sprouting as well as increased presence of low-order branches that terminate rather than branch into daughter segments.

Discussion and Conclusions:

The embodiment Bonfire program integrates with two existing tools used in neuronal digitization (NeuronJ and NeuronStudio) and provides a means of extracting Sholl profiles from digitized neurons stored in standard SWC format. Furthermore, the linkage of an automated, structure-based labeling system with an automated Sholl analysis algorithm creates a powerful new method for quantifying highly specific changes occurring in dendrites and axons following genetic or pharmacologic manipulations. The reason for having multiple methods of segmenting the data is that each method only focuses on a small region of the neuritic arbor, making it better suited to identify effects in that region.

The I/O scheme focuses on primary and secondary neurites at the expense of higher order neurites (FIG. 7(G.1, D.3-F.3)). Such a scheme may uncover morphological effects caused by factors acting at the cell body but may miss changes preferentially affecting only the more terminal regions of the arbor. Conversely, the RIT scheme captures effects of factors at terminal segments but causes a loss of resolution in the intermediate segments since they are grouped together (FIG. 7(G.2, D.3-F.3)). The RIT scheme is best for identifying factors that affect the stability or creation of terminal segments, but this scheme misses effects that occur close to the cell body. The difference in regions of focus between the two schemes is generated by their accounting for the same set of processes differently (FIG. 7(C.3)). This identity-specific information reveals trends in neurite patterning, which were previously obscured by global-level analyses.

Biological Findings:

Primary segment numbers confirm that BDNF exposure increases primary neurite number. However, the absence of a significant change in the number of branch points or terminal points and the lack of a change in the average segment length implies that the effect of BDNF is not due to overall increased neurite branching. Taken together with the absence of a change in the total arbor length, these findings, which represent an entirely new function for BDNF, suggest that global exposure of hippocampal neurons to BDNF in vitro results in a reorganization of neuritic segments within their arbors but not necessarily a change in overall neurite number or length.

Data extracted using an embodiment Bonfire program analysis provide a more detailed view of morphological changes, and for the first time tie the effects of BDNF to specific regions of the arbor. The importance of having the multiple methods of data segmentation provided by the two labeling schemes is clarified by the fact that the analysis identified not only a global effect of bath application of BDNF but also that this global effect is predominantly driven by a change in two specific arbor subregions. These details about the local nature of morphologyical changes have not been identified by conventional methods.

Other Embodiments

One of the most exciting opportunities opened by the generation of morphological data containing local-level detail on arbor structure is the ability to fuel mathematical exploration of the molecular processes locally guiding arborization. Much work has been done deriving generative models of neuronal morphologies. These models are based on observation, but their mechanics are meant to represent biological processes driving cellular morphology. Providing these models with a more detailed source of experimental data would improve mathematicians' ability to generate and test specific hypotheses about biochemical regulatory networks. As mentioned previously, final arbor structure is a result of balanced cytoskeletal assembly and disassembly processes which are regulated by local and global factors. Detailed morphological analysis of specific regions of the dendritic and axonal arbors may provide a convenient window into the regulation of neuronal structure by locally active factors. The result would be a closer integration of mathematical modeling with experimental science.

For example, the mathematical interpretation of Sholl data can be performed using multiple methods. Selection of the most informative one may be dependent on cell type, or even the process type within one cell, implying that the biological drivers of neurite branching and growth may change based on context. However, even using multiple mathematical approaches, interpretation of standard Sholl analysis is not straightforward. An observed increase in Sholl intersections may be due to a variety of changes in branching behavior, including increased sprouting from the soma, more rapid neurite bifurcation, delayed termination, or even neurite extension from the periphery back toward the soma. It is therefore necessary to determine the contribution of each process type to the overall Sholl curve if such information is to be instructive of the underlying biological processes.

Semi-automated Spike Sorting for Increased Information Retrieval from Microelectrode Array Recordings Extracellular Voltage Traces (EVTs)

Figure 9:
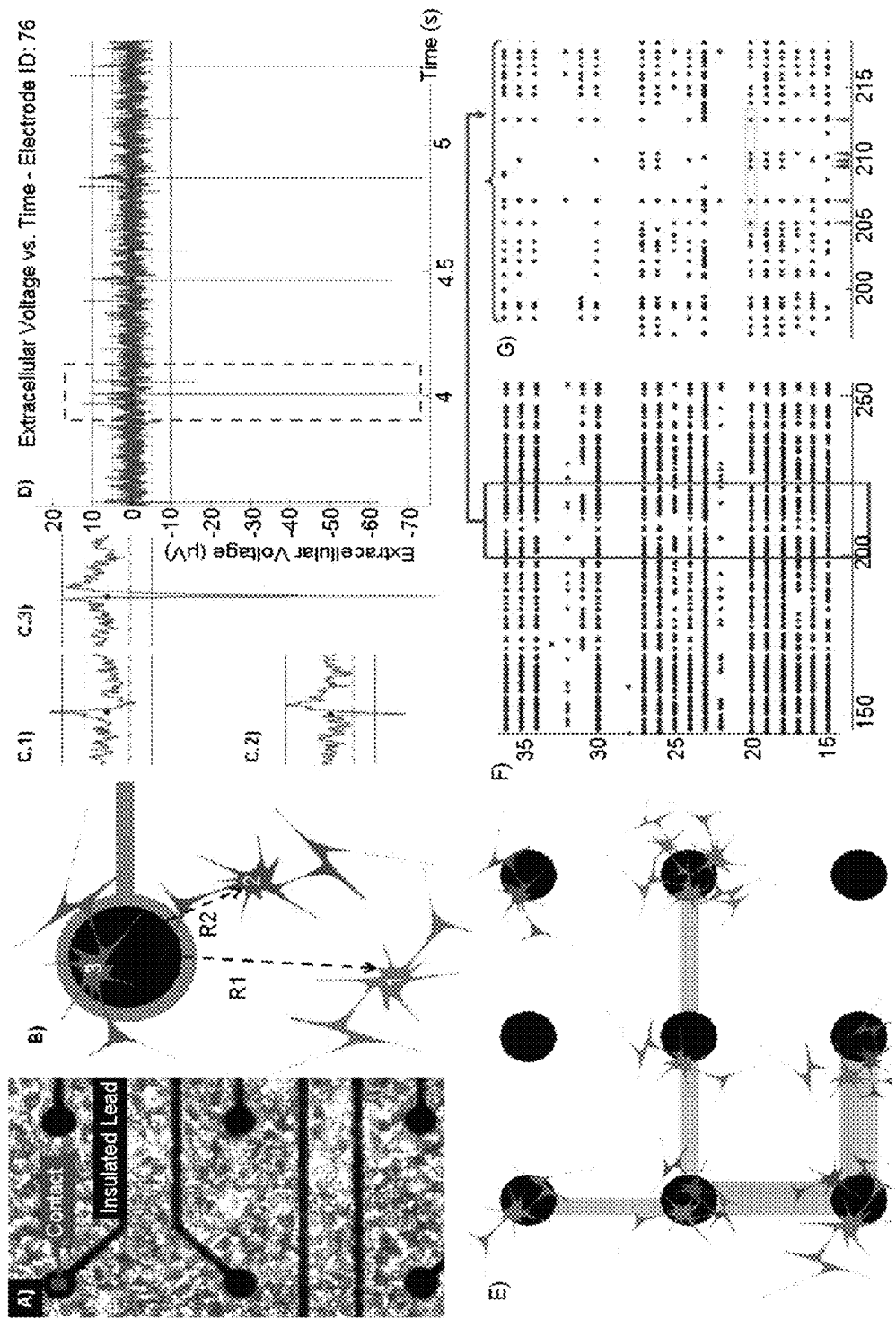
FIG. 9 shows recording and interpretation of EVTs using an embodiment MEA.

Drawing reference to FIG. 9, FIG. 9(A) shows phase microscopy of muscle-cell culture on a commercially available MEA. FIG. 9(B) shows a schematic representation of potential neuron locations relative to a contact pad on the MEA. FIG. 9(C) shows example segments of EVT recorded from a single electrode, showing three distinct spike morphologies (small-positive, small-negative, and large-negative), indicating the likely presence of three nearby neurons. Threshold levels used for spike detection indicated by black dashes. FIG. 9(D) shows seconds of example EVT data recorded demonstrating temporal relationship of spike events. FIG. 9(E) shows a schematic representation of neuronal culture on MEA, showing multiple active units with multiple patterns of connectivity. FIG. 9(F) shows example spike trains from unsorted EVTs (Time is on the X axis, electrode ID is on the Y axis). Each row corresponds to an electrode, and each blue dot indicates a spike occurrence at that time. FIG. 9(G) shows a close-up of 20 s of data. The vertical alignment of events quailtatively shows there is network activity (green and red arrows on the bottom axis), but because the units are not sorted by biological source (only by electrode location), it is impossible to quantitate the linkage between cells.

Recording neuronal EVTs is performed by placing a conductor, which is connected to a recording device, in the vicinity of a neuron's soma where neuronal action potentials create their largest transmembrane current. This rapidly changing current creates voltage transients that can be transmitted along the conductor and subsequently recorded. A conductor will transmit all such activity along its length, so regional specificity is achieved by insulating all of the conductor except the points from which you want to record activity. In vivo MEAS, for example, usually include arrays of conducting wire, insulated along their length except for the tip. In vitro MEAS include conducting layers deposited on top of a glass slide and insulated everywhere except at the contact pads (FIG. 9(A)).

Extracellular voltage at any point is the sum of a number of factors, including the activity of any neurons close enough that their APs can be detected (FIG. 9(B)), as well as noise. Because neurons are frequently packed closely together (in vitro and especially in vivo), this means that any EVT may contain information from any number of neurons. The interpretation of data from multiple neurons recorded on a single channel is a complex problem that has been likened to trying to understand the function of an orchestra without any knowledge that the final sound is generated by different instruments playing simultaneously. Similarly, the most meaningful interpretations of neuronal activity depend on knowing the activity of single cells, due to the nature of information exchange through action potentials (APs). FIG. 9(E) shows a schematic of one possible arrangement of neurons on an MEA. Neurons are networked selectively (and color-coded by network), and contact pads are shown in black. Synchronous depolarization of a network would result in nearly simultaneous event detection on each of the pads contacted by that network.

The blue network and green network would be easily differentiated based on the pattern of activated electrodes because they do not spatially overlap. However, the green network completely overlaps the red network, making differentiation between the two far more difficult. FIGS. 9 (F-G) show unsorted sample data recorded from 22 electrodes in a culture where the situation of overlapping networks likely exists. The vertical banding apparent in FIG. 9, F indicates that networks are present, and are causing synchronous activity. The expanded view (FIG. 9(G)) further shows that this activity is likely a combination of a large network causing activation of a majority of electrodes (indicated on the bottom of FIG. 9(G) with green arrows), and a smaller network on a subset of these electrodes (bottom of FIG. 9(G) with red arrows). Teasing out the behavior of these networks, and therefore making full use of the EVT information, requires determining the firing patterns of each neuron whose activity is recorded by any one electrode.

Neurons are believed to communicate through discrete events (APs), which occur at specific points in time. Such phenomena are modeled using "point processes" in probability theory. The EVTs recorded from an MEA, however, are continuous measures of extracellular voltage over time (an example segment of an EVT is shown in FIG. 9, D). The computational techniques used to translate continuous EVTs to point processes representing the single cell activity of an unknown number of neurons are therefore a highly desirable first step in analysis of this type of data. Though this task is a formidable one, it is made possible by the fact that every neuron fires action potentials resulting in EVTs with a signature shape specific to only that neuron. FIG. 9(C) shows three differently shaped events recorded in an EVT from a single electrode. This is because each individual neuron has a unique location and orientation relative to the electrode contact, and the quality of extracellular environment separating the two is unique. The process by which each depolarization event recorded in an single-electrode EVT is assigned to a particular neuron is known as "spike sorting."

Spike Sorting Process

The process of spike sorting can be roughly broken into a three step process: 1) likely spike events are identified in the continuous EVT, 2) features that may be used to identify the origins of these events are defined, and 3) the events are classified into multiple groups based on the clustering of these features. While there are additional methods of interpretation that do not rely on spike sorting, these will not be considered here. There are multiple methods for performing each step of the process mentioned above, and there is no consensus on which performs best. Technique validation is further complicated by the fact that each step is largely modular and may therefore be used with many combinations of the other steps and that there is a large amount of variability associated with hand sorting of the data (considered the gold standard). Consequently, there are essentially limitless permutations of analytical techniques and no real means for comparing their efficacy.

Selecting the best set of algorithms is, therefore, primarily a function of what the data are needed for subsequently. Experimenters looking to answer specific questions may be able to tolerate one type of uncertainty in favor of gaining specificity on another metric. This unique set of constraints determined by the experimental design will dictate the correct assembly of their spike-sorting process.

Because various embodiment work with muscle cells, a number of unique problems are faced. In particular, the APs generated by the muscle cells are likely to produce widely variable spike shapes between units due to the unique shape of each cell. Additionally, even the EVTs produced by a single cell are likely to show wide variability because the cell is capable of movement relative to the electrode over the course of AP generation. Finally, custom electrode designs may be used where each electrode is likely to have differing noise levels because of their different dimensions.

A program to at least semi-automate the process of spike sorting was designed with this in mind and composed in MATLAB (Mathworks, Natick Mass.) to accept data from a Multichannel Systems MEA recording setup. It will be appreciated, however, that any suitable programming language may be used. As discussed earlier, the resultant program may be stored in the memory of a computer and executed by a processor to cause the processor to perform the various method steps. In this program, an attempt is initially made to automatically analyze all data. The program then prompts the user to "proof" the data and guides the user through a revision analysis on data segments where the automated process failed to sort the units correctly. The algorithms involved in the embodiment program, and the rationale for their selection, are discussed below. Sample data sets of neuronal and myotube recordings were analyzed to confirm functionality.

Example

Cell Culture and Sample Data Acquisition

Myoblasts and cortical neurons were isolated and cultured. Briefly, pregnant Sprague Dawley rats were sacrificed by $CO_2$ inhalation at gestational day 21 for myoblasts and 18 for cortical neurons, in accordance with Rutgers University animal care procedures. To isolate cortical cells, pups were removed by Cesarean section and cortex was isolated and the meninges removed, and cortex was triturated to create a single cell suspension. Cortical cells were then seeded onto MEAS in MEM medium plus 1% penicillin/streptomycin, 10% horse serum, and 3% v/v of 20% glucose solution at a surface density of 225,000 cells/cm$^2$. Prior to use, the medium was glutamate depleted by 24 hr exposure to astrocytes culture, and the MEA surface was incubated overnight in 3% PEI dissolved in borate buffer. To isolate myoblasts, pups were removed by Cesarean section and hind limb muscles were removed to a separate container of Hanks' Balanced Salt Solution (Invitrogen, Carlsbad, Calif.) +1% HEPES Buffer (Mediatech, Inc., Herndon, Va.). Tissue was finely minced and brought to a final volume of 7 ml in PBS containing 1.5 U/ml collagenase (type D, Roche, Mannheim, Germany) and 2.5 U/ml dispase (type II, Roche, Mannheim, Germany). Tissue slurry was then incubated for 20 min at 37° C. and triturated using a pipette to break up remaining tissue clumps.

Solid debris was allowed to settle for 15 minutes, and remaining cells were pelleted out of the supernatant by centrifugation. The cell pellet was resuspended in growth medium consisting of Ham's F-10 medium including 20% fetal bovine serum, 1% Penicillin/Streptomycin, (all from Invitrogen, Carlsbad, Calif.) and 2.5 ng/ml human b-FGF (Promega Corp., Madison, Wis.). Cells were then plated into 75 cm$^2$ flasks and incubated for 24 hrs to allow for attachment of viable cells. Cultures were washed 3× with PBS to remove non-adherent cells and debris. Cells were then resuspended and plated onto commercially available MEAS (Multichannel Systems) at a density of 100,000-300,000 cells/cm$^2$ depending on the experiment in differentiation medium consisting of Neurobasal medium including 2% B-27 Supplement, 1% Penicillin/Streptomycin and 1% GlutaMAX (all from Invitrogen, Carlsbad, Calif.). Prior to seeding, surfaces were coated with laminin (Sigma Aldritch, St. Louis) at 40 μg/ml. Recordings were made using a standard MCS recording array, sampling the extracellular voltage from 60 contact pads at 20,000 Hz. Contact pad spacing was 200 μm and diameter was 10 μm. Recordings were made throughout the development of cultures to observe a wide variety of behaviors.

Event Detection

The detection of unsorted spike events is typically performed by amplitude thresholding in which all instances where the EVT exceeds a certain threshold are recorded as potential spikes. An adaptive thresholding technique was used, in which the spike-threshold is set to a multiple of the SD for the entire data segment. Additionally, because myotubes are expected to depolarize over a variable length of time, a variable "blanking window" was imposed after each instance where the threshold was broken. After an event is detected, the blanking window prevents the identification of subsequent events for a set time.

Feature Generation

Features representing spike characteristics can be generated based on a wide variety of techniques. Some draw from very obvious morphological characteristics which are apparent to the naked eye, such as amplitude and duration or template matching. Others draw on computational techniques to generate less obvious characteristics, involving Fourier and wavelet transforms. Principal Component Analysis (PCA) was selected for our algorithm because of the high degree of flexibility it provides relative to its computational simplicity. PCA identifies variance between sets of vectors and returns basis-vectors that explain this observed variance in rank order of importance, known as the principal components (PCs). In other words, it is a way of automatically generating features based on the variability in the dataset it is run on. This means that a custom set of PCs is created for each electrode's EVT recording rather than needing a set that is applied to all EVTs equally.

The first step of PCA is creating the set of vectors it is run on. This is done by taking each fragment of the full EVT that was identified as a likely spike and aligning them. In various embodiments this is a multi-step process which 1) identifies an instance of where the EVT breaks the spike-threshold, 2) establishes an investigation window around that point, 3) identifies the maximum amplitude of the EVT within that window, 4) assigns the point of maximum amplitude as the event center, and 5) realigns each event to that point.

Figure 10C:
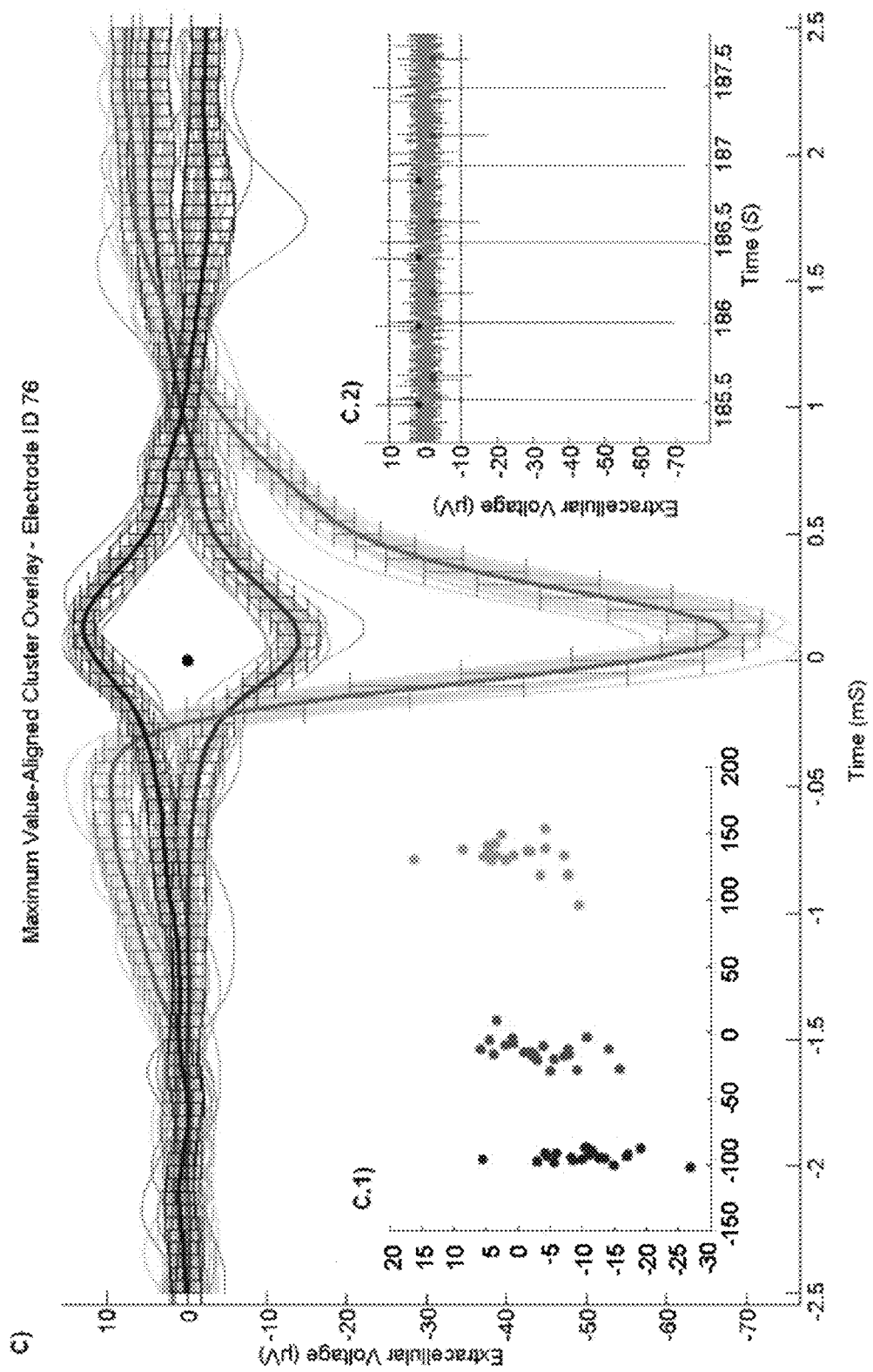
FIG. 10 illustrates spike-sorting by principal component analysis (PCA).

FIG. 10(A) shows example data (same as from FIG. 9 (B)), now showing the location of the placement window (bold red bar) and the blanking window (dashed red bar), relative to the point at which the EVT crosses the spike threshold (black dashed line). FIG. 10(B) shows EVT spikes following alignment to their point of maximum displacement (red lines) along with the first two PCs identified by the PCA process (dashed and dotted blue lines, respectively). C) Spike assignment by clustering. FIG. 10(C) shows spikes after clustering. Each individual trace appears in the faded color, while the average of all spikes in that cluster and their standard deviation appear in darker lines. In FIG. 10(C.1) each spike is represented by a point at a unique location in PC-space (PC1=x-axis, PC2=y-axis), based on it's similarity to the PCs shown in panel B. Clusters identified by K-means algorithm are color coded, and correspond to the colors shown in panel C. These spikes can then be identified by location in the full EVT (FIG. 10(C.2)). This returns the information on the firing sequence of three individual neurons, even though they are all recorded on only one electrode.

FIG. 10(A) shows three example incidences where the spike threshold was broken and establishment of the interrogation window (thick red line) and blanking window (dashed red line) around that point. The size of the interrogation window (both lead time and lag time) can be adjusted as needed. FIG. 10(B) shows all incidences from 60 S of example data aligned to maximum deflection point, as described above. PCA is then run on the set of aligned spike vectors and the first two PCs (FIG. 10(B) blue lines) are used to generate a 2 dimensional feature space.

Clustering

While a number of alternative clustering algorithms are available, an embodiment program uses either K-means or a Guassian mixture (GM) algorithm, depending on what phase of operation the program is in. Automatic analysis utilizes the K-means approach, while user-assisted analysis takes advantage of the GM process. In either approach the process progresses as a series of trial-and-error attempts to identify the correct number of clusters that best explains the data followed by an assessment of how successful the effort was.

During user-assisted analysis, the user defines the number of clusters the GM process should look for, using any suitable input means coupled to the computer and from which the processor can obtain corresponding user input data. Then, based on these clusters, the user may select clusters to split or join until optimal sorting is achieved as defined by the user. Each time a cluster is split, it is reanalyzed in its own PC space rather than the PC space of the full data set, which resulted in the original poor clustering. During automatic clustering the K-means algorithm is used. The embodiment program successively identifies 1-8 clusters in the data and scores the efficacy of the clustering based on a measure of the distance between all points in each cluster. Cluster sets where all points in each cluster are close to each other and far from the points in the other clusters are scored well, while cluster sets where points in each cluster are closer to the points from other clusters than they are to each other are scored poorly. The cluster set receiving the highest score is assumed to be the most appropriate clustering of the data and is passed to the next step in the process. FIG. 10(C.1) shows example data that has been clustered (3 clusters were identified).

Post-processing and Recombination of Correlated Clusters

Following clustering, groups are "tightened" by shifting the time stamp for all events to the location where they are all maximally correlated with the first instance in their cluster. The cluster average and SD are then calculated. All events in the cluster are therefore maximally correlated with this mean curve. The time at which the cluster average breaks the threshold is then assigned as the event time for all events in that group. Finally, all curves are aligned to this break point and are cross-correlated. Spike groups where the correlation between their shapes is above a threshold value are then combined. FIG. 10(C) shows the three traces from FIG. 10(B) after they have been assigned to clusters, corresponding to the activity of individual cells. Once this has been successfully completed, the firing sequence of each of these cells can be observed in the original EVT (FIG. 10(C.2)).

Recursive Evaluation and Workflow

Once all data have been sorted automatically, the program allows the user to "proof" the spike identification process by showing the clusters obtained on each electrode. The user then has the opportunity to accept the sorting, exclude the electrode altogether (as would be done with nonfunctional/noise electrodes), or to mark the electrode for revision analysis. The program uses the information to build a list of electrodes which need to be revisited and then allows the user to perform spike sorting by hand on these electrodes.

Discussion and Results:

Either K-means or GM clustering methods perform well. GM works best in the hands of a human because the distribution of the points when non-stationarity is a problem is largely non-Gaussian. Most large scale variance is caused by non-stationarity effects and causes slurring of the clusters along some manifold. Of particular note in the clustering step is the reanalysis of split clusters in their own PC space. This creates a higher definition feature space in which other clusters do not reduce the ability to distinguish more "closely" related clusters by creating a false relative proximity. This makes the process of splitting and joining clusters accurate and comparatively bias-free, as points are still always clustered based on either of the two algorithms above.

Another unique aspect of this embodiment algorithm relative to many currently in use, is the consolidation of clusters and time shifting to align them to the threshold breakpoint.

Muscle cell APs can go on for over 10 μs and can have multiple peaks and valleys, which means considerable delays are possible between the onset of an AP and the point of maximum deflection. Identifying the time stamp for an event that allows for accurate identification of event onset will facilitate the identification of an accurate firing sequence, and therefore, potentially causal relationships within a network.

Conclusion:

The embodiment program is successfully able to sort spikes based on the EVT morphology. A fully-automated (i.e., unsupervised) analysis of 1 min of data recorded on 60 channels requires ~3 hr to complete but does not require any user intervention. By hand analysis of this same data segment typically takes ~5 hrs of user-intensive labor. While automated clustering is successful in ~50% of cases, the embodiment program is unable to appropriately group the spikes in the more complicated channels. Therefore, by hand analysis is still generally desirable to correct deficiencies in the automated spike-sorting process. Once channels requiring hand sorting have been identified, the program provides enough structure to assist the user in the logical grouping of spikes but also enough flexibility to adequately guide the grouping process. Because the automated process correctly deals with ~50% of the channels, however, it reduces the time it takes to analyze these large data sets by half. Most importantly, it provides an accurate measure of spike morphology, which can be used in subsequent analysis, and also an accurate firing sequence for all identified units, which will provide appropriate input for subsequent network identification processes.

Figure 11:
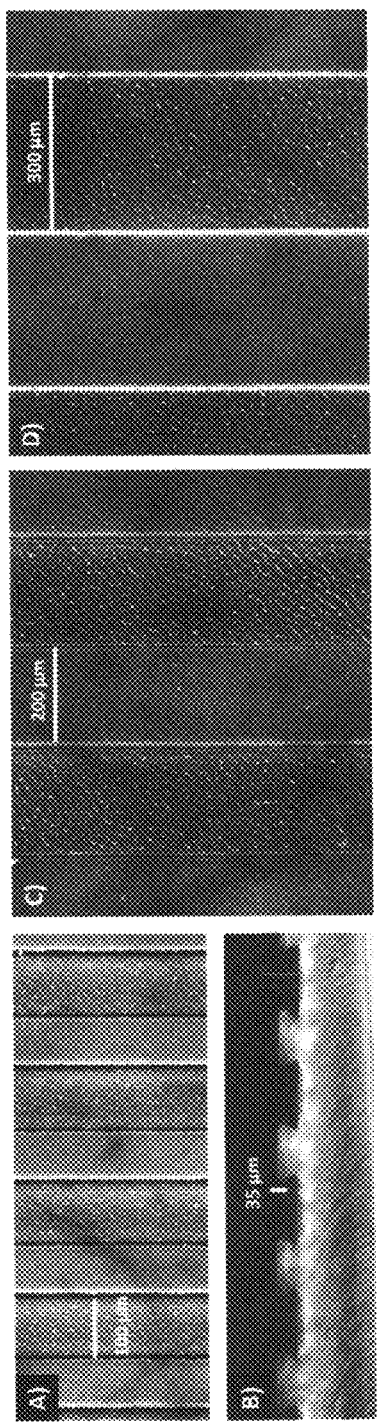
FIG. 11 shows characterization of a PDMS substrate.

The effect of microscale grooves on skeletal myotube alignment and independence in a 2D culture system Substrate Fabrication and Characterization Referring now to FIG. 11, FIG. 11(A) is a top-down microscopic view of an embodiment PDMS substrate with 100 μm trench width and spacing. FIG. 11(B) is a side view of the substrate from (A). Similar substrates with different geometries were produced using the same technique with trench spacing an width of up to 500 μm (200 μm and 300 μm shown in FIG. 11(C) and FIG. 11(D), respectively).

Polydimethylsiloxane (PDMS) monomer (Dow Corning, Sylgard 184) was mixed 10:1 with curing agent. The solution was poured over a silicon wafer, which had been coated with SU-8, into which the negative pattern of embodiment groove geometries had been developed. After degassing under vacuum for 30 min, the PDMS was cured overnight at 37° C. The PDMS was then peeled from the surface of the silicon SU-8 master, resulting in a positive pattern of grooves. The geometry of the grooves on the resulting substrates was characterized using bright field microscopy (FIG. 11). Sample substrates were imaged top down (FIG. 11 (A)), and in cross section following transaction (FIG. 11(B)). The size of each feature in pixels was counted using ImageJ software (NIH, Bethesda Md.)] and converted into μm using a known conversion factor specific to the microscope objective. A pattern of parallel grooves with equal pitch and width were selected for an embodiment geometry so that each viewing field contained an equal quantity of groove and plateau surface area.

Myotube Isolation and Culture

Myoblasts were isolated and cultured as previously described. Briefly, pregnant Sprague Dawley rats were sacrificed by $CO_2$ inhalation at gestational day 21, and pups were removed by Cesarean section. Hind limb muscles were removed, and tissue was finely minced and digested (20 min at 37° C.) in PBS containing 1.5 U/ml collagenase (type D, Roche, Mannheim, Germany) and 2.5 U/ml dispase (type II, Roche, Mannheim, Germany). Single cells were separated from debris, pelleted by centrifugation, and resuspended in growth medium consisting of Ham's F-10 medium plus 20% fetal bovine serum, 1% Penicillin/Streptomycin, (all from Invitrogen, Carlsbad, Calif.) and 2.5 ng/ml human b-FGF (Promega Corporation, Madison, Wis.). Cells were then plated into 75 $cm^2$ flasks and incubated for 24 hrs. Adherent cells were resuspended and plated onto PDMS substrates in differentiation medium consisting of Neurobasal medium including 2% B-27 supplement, 1% Penicillin/Streptomycin and 1% GlutaMAX (all from Invitrogen, Carlsbad, Calif.) at a surface density of 200,000 cells/$cm^2$. Prior to seeding, surfaces were plasma treated ($O_2$ plasma for 120 S at 50 Watts) and adsorbed overnight with 40 μg/ml laminin (Sigma Aldrich, St. Louis, Mo.). Medium changes were performed every other day.

Quantification of Myoblast and Myotube Alignment

Myoblasts were seeded onto PDMS substrates bearing either 100 μm×100 μm, 200 μm×200 μm, or 400 μm×400 μm trenches (trench width μm×separation μm). PDMS substrates with a smooth surface were used as an unaltered control, and each surface was prepared in triplicate. Two randomly selected fields, showing 0.55 $mm^2$, from each myoblast-seeded substrate were imaged using a phase contrast microscope at 12 hrs post seeding and every 24 hours after that until DIV 8. Myoblast alignment in these images was assessed using a modification of the image intensity gradient algorithm. Briefly, each image was broken into square tiles. The intensity gradient of each pixel in this square interrogation window in both the X direction ($\delta_x$) and Y direction ($\delta_y$) is calculated and then averaged across the field. An angle, θ, is then calculated based on the arctan of $\delta_y/\delta_x$, which represents the average orientation of optical density within that field. This series of operations is repeated for every square tile and the distribution of resultant θ's provides a measure of bulk culture alignment. Squares located on trench edges were excluded to prevent the introduction of substrate-based alignment bias.

Quantification of Myotube Contractility

To dynamically analyze contractile activity of myotubes, videos of cell behavior were acquired after the onset of spontaneous contractility and were analyzed as described above. Briefly, videos were analyzed using a series of image processing and pattern recognition steps, which made it possible to identify regions of synchronized contractility within videos of myotube cultures. This analysis provided the number and location of the contractile myotubes. An additional step was added to this process in which the orientation and locations of the trenches were identified in each video, allowing additional analysis examining the spatial relationship of spontaneous contractility to the trenches.

Three measures relating contractility and trench location were examined. The first was the percentage of the contractile activity that is located in the trenches, calculated as the sum of all contractile area located inside of the trenches divided by the total area identified as contractile in the video. The second metric was the average number of trenches spanned by each myotube, where at least 5% of the myotube must be located in a trench in order for it to be counted. The final metric was the average number of myotubes that exist in each trench, again where at least 5% of the myotube must be located in a trench in order for it to be counted. Because there were no trenches on the smooth control surfaces, videos of myotubes on trenches were compared to smooth surfaces on which the same orientation and trench pattern had been artificially imposed. Thirty second videos of myotube behavior were acquired over 200 frames using a 10× objective and 512×640 pixel resolution, recording an area of 0.55 $mm^2$. Two videos for each triplicate replication of PDMS substrates bearing 100 μm, 200 μm, and 400 μm trench geometries as well as a smooth control were analyzed.

Myotube Morphology on PDMS Substrates with Microscale Topographical Trenches

FIG. 12(A) shows myotubes at DIV 11 grown on unpatterned (top) and laminin-striped (middle and bottom) glass. FIG. 12(B) shows myotubes at DIV 11 grown on PDMS substrates topographically modified with 30 μm grooves (left), 50 μm grooves (middle) and 150 μm grooves (right). Striations in myotubes at DIV 14 grown in the plateau region FIG. 12(C) and groove regions FIG. 12(D) of a topographically modified PDMS substrate.

Figure 12:
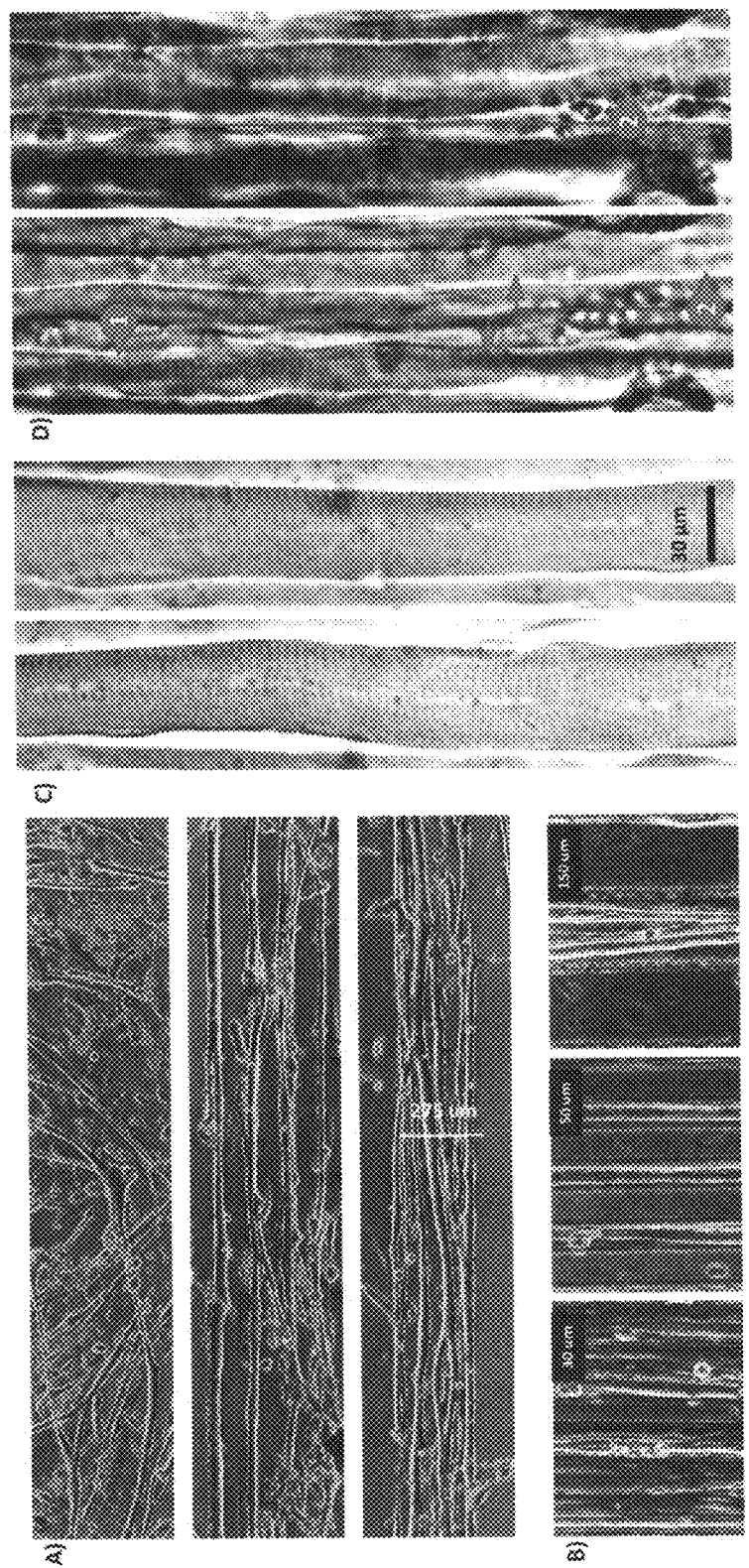
FIG. 12 shows myotube morphology on embodiment chemically and topographically patterned substrates.

It was found that both microscale chemical and topographical patterning techniques were effective at directing myotube alignment (FIGS. 12(A and B)). Conditions affecting the rate of fusion and the final myotube morphology (shape and size) include seeding density and surface chemistry. Surfaces adsorbed with profusion proteins, such as laminin, promoted myotube differentiation while those adsorbed with non-bioactive adhesion promoters such as polyethyleneimine (PEI) or poly-D-lysine (PDL) did not (data not shown).

On laminin adsorbed surfaces, myoblast fusion and maturation into striated myotubes was robust. Myotubes in the intertrench plateau regions tended to be flattened out and non-overlapping, pushing more of the myotube into one focal plane and facilitating visualization of the striations (FIG. 12(C)). Cell growth in the trench regions tended to be more three-dimensional and allowed for multi-layered growth, requiring images from serial Z-planes to show myotube striations (FIG. 12(D)). While this produced local changes in cell density, each low magnification image contained a constant cell density because it contained equal portions of trench and plateau regions regardless of trench geometry, due to our selection of substrates with equal trench width and spacing.

It was also found that there is an optimal width for creating patterns of physically isolated, unbranching myotubes (FIG. 12(A)). For chemical patterns, it has been observed previously that as the feature size is reduced below this critical size, myotubes either connect between features or fail to adhere and mature, and as feature size is increased over the critical size, several myotubes are able to associate within each feature. Optimal trench spacing for achieving a 1:1 trench-to-myotybe relationship was similar to the dimensions for chemical spacing. FIG. 12 (B) shows primary myocyte cultures on trench widths of 30 μm, 50 μm, and 150 μm. On 50 μm trench geometry, each feature contained a single myotube. In the larger groove geometries, multiple myotubes co-localized within the same feature, and on smaller trench geometries, myotubes were able to reach across trenches. The width of individual myotubes, however, appeared largely unchanged between these different scenarios. Trench width may therefore preferably be between 30 μm and 100 μm, and more preferably still between 30 μm and 70 μm, such as 50 μm.

Figure 13C:
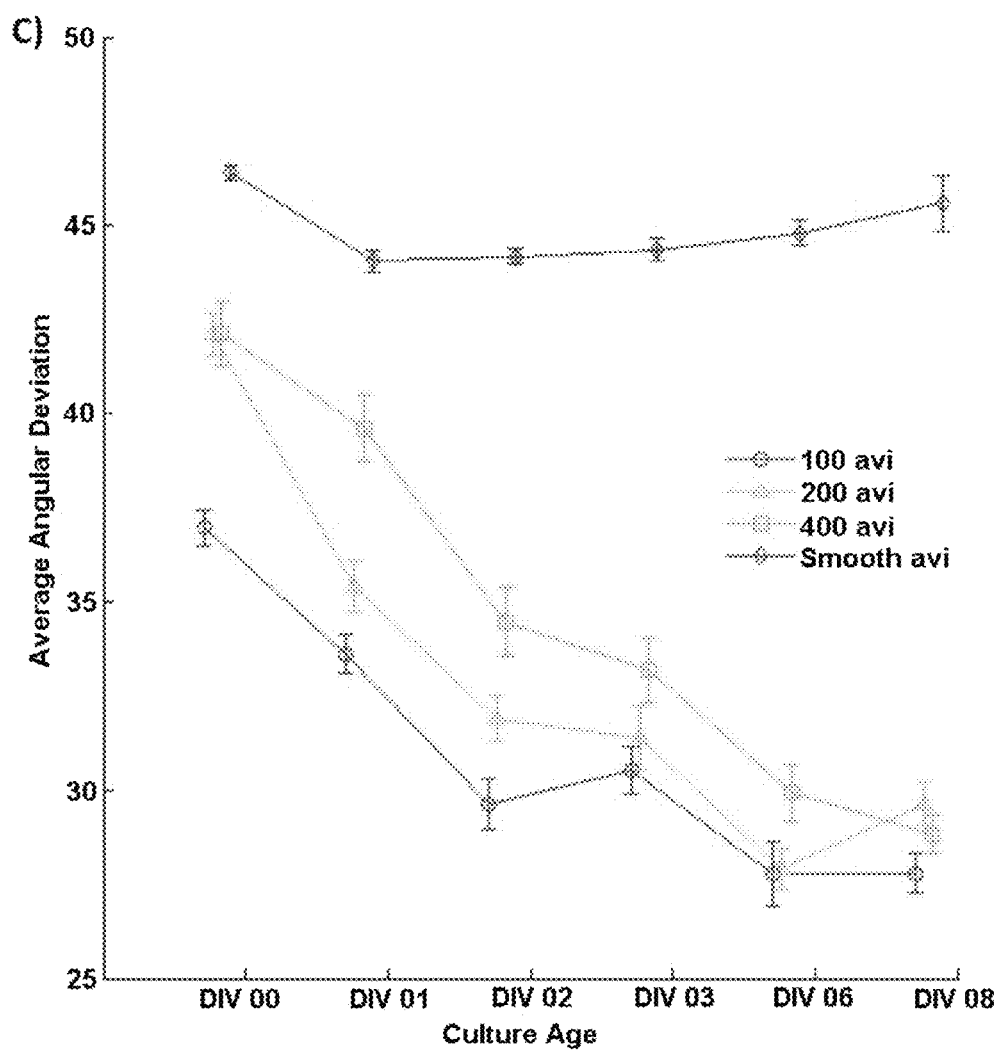
FIG. 13 illustrates myoblast alignment with major trench axis in DIV 0-DIV 8.

FIG. 13(A) shows angular deviation distribution (top) of local alignment fields detected using gradient method (example field bottom) for myoblasts on 100 μm trenches 12 hr after seeding. FIG. 13(B) shows angular deviation distribution (top) of local alignment fields detected using gradient method (example field bottom) for myoblasts on an unpatterned PDMS substrate. FIG. 13(C) shows average amplitude of angular deviation from the major trench axis for substrates with 100 μm, 200 μm, 400 μm and unpatterned control for timepoints from 12 hr after seeding to DIV 8.

In one embodiment the optical gradient method was used to identify the effective angle of alignment for each square field of the microscope image based on the average X- and Y-intensity gradients of the pixels therein (FIG. 13(A and B-bottom, red bars)). Orientation of each square field can then be compared to the orientation of the trenches. The distribution of orientations for the entire image relative to the primary trench direction will be highly concentrated around zero for cultures that are highly aligned with trench axis (FIG. 13(A-top)) or will be flat for cultures with random growth (FIG. 13(B-top)). To characterize this distribution, the average angular deviation from the trench axis can be calculated, which will be approximately 45° in the case of random growth and will be lower in the cases of more organized growth.

Analysis of myoblast and myotube alignment using this method showed that myotube alignment was induced by topographical guidance cues, consistent with prior studies on guidance cues of similar size. Myotube cultures seeded on PDMS substrates with trenches had an average angular deviation noticeably lower than that observed in cultures grown on smooth PDMS substrates, which was approximately equal to the 45° expected from truly random growth (FIG.(13 C)).

Analysis over the timescale of DIV 0 through DIV 8, however, showed a number of additional trends in myoblast alignment and fusion into myotubes. While myotubes on all grooved substrates ultimately reach the same degree of directed orientation by DIV 8, there are transient differences between substrates bearing 100 μm, 200 μm, and 400 μm trench geometries during early time points (FIG.(13 C)). Alignment of myoblasts, even before they have begun to fuse into myotubes, occurs sooner on the narrower trench geometries, as exhibited by the alignment of unfused myoblasts as early as 12 hours after seeding on 100 μm trenches (FIG. 13 (A)) relative to an unpatterned control (FIG. 13(B)).

Myotube Contractility on PDMS Substrates with Microscale Topographical Trenches

Spontaneous contractility is observed in many myotube culture systems. With the recent development of an algorithm for quantifying myotube association based on videos of spontaneous contractility as discussed above, it is possible to look at the effects of topographical guidance cues on this measure of myotube function in addition to simple morphological examination. Myotubes in culture underwent an early period of maturation during which spontaneous activity increased as myotubes fused and matured, followed by a gradual decrease in activity. The exact time course of these events is a product of factors specific to each culture system, ranging from medium composition, cell source, cell density, and various characteristics of the extracellular environment. In an embodiment culture system, spontaneous twitches have been observed as early as DIV 5 and can continue through 3 weeks in culture. When this spontaneous activity is quantified, a similar trend is seen as is observed in the myotube alignment data. While myotube cultures on grooved substrates exhibited a greater number of spontaneously contractile cells during early time points (i.e., DIV 8-13), the myotube cultures on smooth substrates ultimately caught up to them and produced similar quantities of spontaneously contractile cells (i.e., DIV 15-17).

The embodiment contraction identification algorithm also shows the physical location of contractile myotubes. This analysis shows trends in the spatial distribution of contractile activity that is dependent on trench geometry. Qualitatively, myotube contractility appears to be directed to, aligned with, and confined largely within the trenches. The highest degree of order is achieved at 100 μm, with disorder increasing as the length of uninterrupted trench width increases. On the 100 μm trench geometry, myobutes aligned along the trench axis, and typically, there was only 1 myotube per trench. When the trenches were this close together, however, it was possible for one myotube to bridge multiple trenches. On the 200 μm trench geometry contractility was still largely directed to the trenches but it became possible for multiple myotubes to be active in a single trench. On 400 μm trench geometry myotubes increasingly spilled out of the trenches, there was an increase in overlapping activity, and there was diminished alignment and elongation of contractile areas within the trenches. Finally, on smooth substrates, there was no order to the myotube activity, and myotube contractility was distributed in random locations and with random orientations.

Myotube Contractility Selectively Guided to Trenches

Figure 14A:
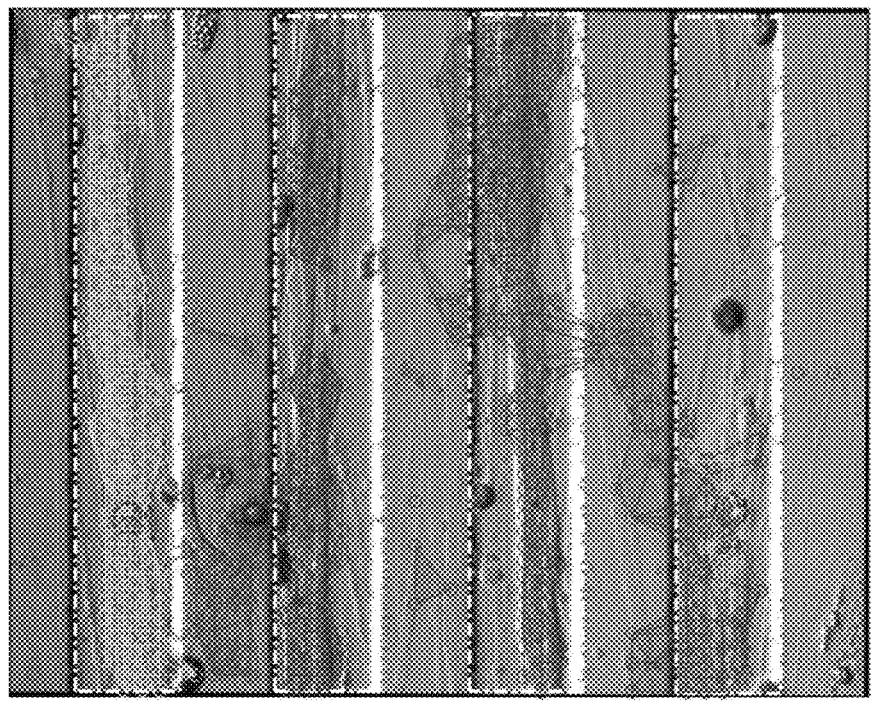
FIG. 14 illustrates myotube contractility spatial relationship with embodiment trenches.
Figure 14B:
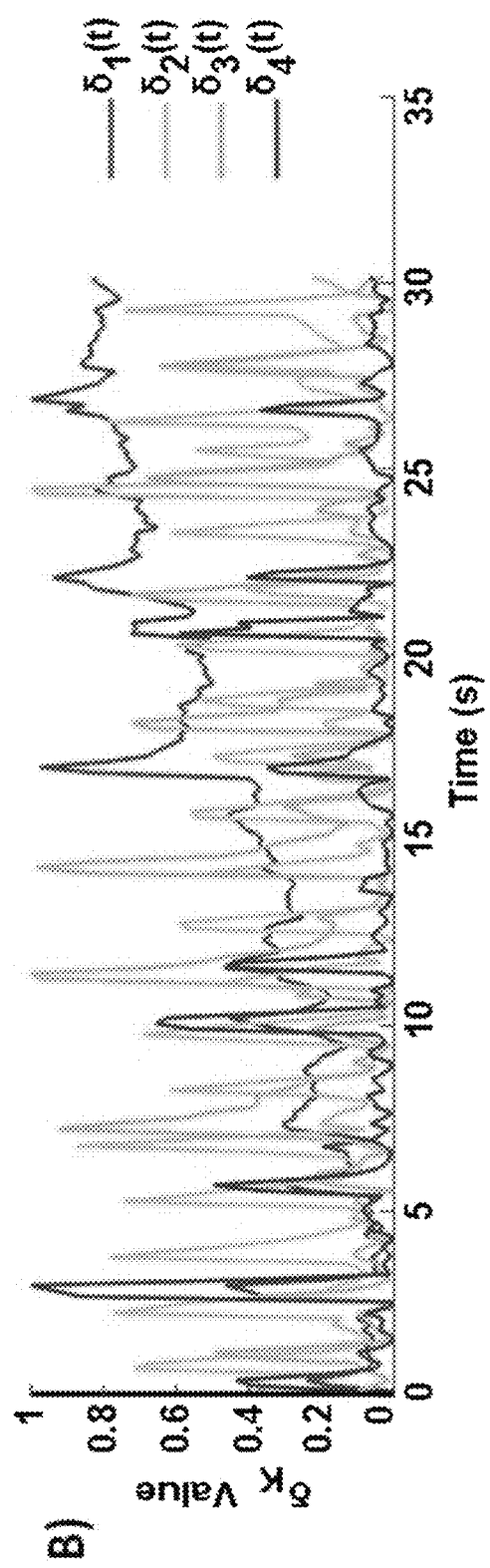

FIG. 214A) shows an example image of contractile myotubes at DIV8 on 100 μm groove spacing. FIG. 14(B) shows activity pattern of myotubes indicated in FIG. 14(A). Percentage of total contractile area located in trenches for FIG. 14(C), the average number of trenches spanned by each myotube FIG. 14(D), and the average number of myotubes found in each trench FIG. 14(E), is quantified for 100 μm, 200 μm and 400 μm trench geometries (filled points) relative to unpatterned control for each case (empty points). Error bars represent the standard error of the mean.

By superimposing a map of contractile activity on the location of trenches (FIG. 14(A)) for each video, it is possible to quantify the relationships between contractility distribution and trench location. Because it is possible that trench distribution itself may create a sorting effect, each video of myotube behavior on patterned substrates was compared to videos of unpatterned cultures on which the trench pattern from the video being analyzed was superimposed. For some of the metrics examined, there was a slight trend, suggesting a dependence on trench spacing. However a much greater effect was clearly present between each patterned substrate and its unpatterned control.

FIG. 14(C) confirms the observation that contractile activity is directed largely to the trenches. In each of the trench geometries substantially more contractile activity appeared in a trench region compared to the smooth control surfaces. Because trench spacing and width are equal in all geometries, 50% of the surface shown in each video is trench and 50% is the intertrench plateau region. This means that in the case where myotube activity is randomly distributed, we would expect to find ~50% in the trenches, which is the case in the embodiment system.

Not only is contractile activity directed generally to the trenches, but trench location correlated with contractile activity with some degree of specificity depending on trench geometry. For example, in the 100 μm trench geometry, a single trench typically only contained a single myotube, while many myotubes were able to span multiple trenches. By comparison, in the larger trench geometries, the wider trenches were more likely to contain multiple myotubes while it is more difficult for single myotubes to span the larger distance between trenches. This observation is reflected in FIG. 14(D and E) where the closely spaced and narrow trenches of the 100 μm case resulted in a larger number of trenches spanned per myotube, and a lower number of myotubes found in each trench, as compared to the other patterns. More important than a comparison between trench geometries however, is the clear difference between each geometry and the unpatterned controls. Relative to unpatterned controls, myotube formation is directed to the trenches in a selective manner that preserves functional independence of myotubes from those in neighboring trenches.

Conclusions

Changes in myotube behavior in response to microscale trenches are largely a product of early events in myoblast spreading and alignment. Myotube alignment increases through DIV 8, but a large and substrate geometry-dependent difference in cell alignment on patterned and unpatterned substrates was observed as early as 12 hours following seeding. This was likely because in the early stages of myoblast attachment, cell spreading was partially guided by the grooves. The effect was most notable in the narrower trench geometries because these features have spatial dimensions on the same order of magnitude as the myoblasts themselves. Because myoblasts are polarized cells, which are spindle shaped, this head start in alignment reduces the amount of time they need to spend migrating under their own power to achieve the end-to-end alignment thought to be required for fusion and differentiation into myotubes.

While the effects of microscale topographical trenches on myotube alignment are relatively straightforward, their effect on myotube independence is more complicated. Based on the static images that the morphological studies are based on, guidance cue geometries above or below a critical size resulted in communication between myotubes within the same feature or between features, respectively. This was visualized as branching myotubes that were unexpectedly capable of maintaining independence from neighboring cells even when they overlap extensively. This is supported by the observation that the use of microscale topographical guidance cues resulted in earlier alignment and onset of spontaneous activity but did not increase the final number of independent cells. These observations support a conceptual model where myoblast fusion and differentiation is primarily controlled by intrinsic factors rather than the extrinsic factors delivered by the static mechanical cues found in the extracellular environment of the synthetic microscale trenches. While the small boost in myoblast alignment provided by the microscale trenches is sufficient to give the fusion/maturation process a head start, it does not alter myotube cellular physiology, and the functional endpoint reached is ultimately the same.

While microscale topographical features do not have any effect on cellular independence, they can serve the useful purpose of controlling culture mechanics. Micro-scale grooves can be used not only to drive culture-level myotube alignment but also to direct contractile activity to specific regions and encourage contraction in specific directions. Microscale patterning techniques may be used to generate controlled anisotropy, as exists in native tissue architecture, and to direct formation of myotubes to specific locations, as would be desirable for microdevices incorporating an engineered skeletal muscle component.

The embodiment myotube guidance technique may be integrated with multi-modality bio-MEMS devices with substrate embedded electrodes for the purpose of recording bio-electrical activity or selectively triggering contraction of myotubes located in specific regions. Developing such bio-interfaces for tissue engineered skeletal muscle constructs may improve the performance of skeletal myotube-integrated lab-on-a-chip or biorobotic devices by increasing their degrees of freedom for actuation or detection. Additionally, such device may be clinically useful within the context of a microscale adaptation of the targeted muscle reinnervation (TMR) technique, which uses surface EMG to control prosthetic devices in amputees. Making signal acquisition a process that occurs on the scale of single muscle fibers detected with microscale implantable electrodes, rather than course surface electrodes, may increase the number of independent signals that can be recorded, thereby increasing the bandwidth for communication with the user.

Spatially Selective Detection of Extracellular Action Potentials and Neurite Outgrowth in Spinal Cord Explant Culture vs. Dissociated Neuronal Culture Isolation and Culture of Spinal Cord Explants and Dissociated Neurons Spinal cord explants are prepared using procedures known in the art. Briefly, pregnant Sprague Dawley rats were sacrificed by $CO_2$ inhalation at gestational day 15, and pups were removed by Cesarean section. Spinal cord was removed posteriorly and transferred to a PDMS-lined petri dish in a drop of medium. The cord is then bisected longitudinally and finely minced transversely into sections 200-300 µm thick. Sections were suspended in NB medium plus 1% GlutaMAX supplement and 2% B27 supplement. Explants were then plated onto chemically or topographically patterned glass substrates or MEAS, all of which had been adsorbed overnight with laminin at 40 µg/ml in 10 µL of medium. Explants can be precisely positioned on the growth substrate during this step. In this experiment, explants were positions with the explant body over three contacts in the top row of the MEA, allowing space for axonal outgrowth over the other contacts. After 5 min, allowing for initial adhesion, enough medium was added to just cover the explant, and it was placed in an incubator at 5% $CO_2$ and 37 deg C. Medium was replaced every 2 days.

Because spontaneous EAP activity and culture survivability was low in dissociated spinal cord cultures, cortical neurons were used as a proxy to determine spatial distribution of EAPs in dissociated neuronal culture. Cortical neurons were isolated as known in the art. Briefly, pregnant Sprague Dawley rats were sacrificed by $CO_2$ inhalation at gestational day 18, and pups were removed by Cesarean section. Cortex was isolated, meninges were removed and a single-cell suspension was prepared by triturating the cortex with a flame-polished glass pipette. Cortical cells were then seeded onto MEAS in MEM medium plus 1% penicillin/streptomycin, 10% horse serum, and 3% v/v of 20% glucose solution at a surface density of 225,000 cells/cm$^2$. Prior to use, the medium was glutamate depleted by 24 hr exposure to astrocytes in culture, and the MEA surface was treated overnight with 3% PEI dissolved in borate buffer.

Immunostaining

Explants were fixed and stained on DIV 13 to identify axonal and dendritic outgrowth. Explants were fixed in a PBS plus 4% PFA and 4% sucrose solution for 15 min at room temperature. After washing 3 times in PBS, explants were then permeablized and blocked for 1 hr at room temperature in PBS plus 2% FBS, 0.2% Triton, and 0.02% sodium azide. Explants were rinsed 3 times with PBS, and incubated in primary antibody solution for 2 hr at room temperature (1:500 mouse anti-Tau and 1:200 rabbit anti-MAP2). Primary antibody solution was removed, and explants were washed 3 times with PBS before incubation in secondary antibody solution for 1 hr at room temperature (1:300 donkey Cy2-conjugated anti-mouse and 1:300 goat Cy3-conjugated anti-rabbit). Secondary antibody was removed, and explants were washed 3 times with PBS before imaging using an epifloures-cent microscope. Five well-attached explants were imaged in each condition, and their outgrowth was quantified using ImageJ software (NIH, Bethesda Md.).

Chemical Patterning

Laminin patterns were produced using a technique called microscale plasma-initiated patterning. Briefly, PDMS stamps bearing the negative of the desired pattern were created using standard soft lithography techniques. These stamps were then brought into contact with glass coverslips. Surfaces where the PDMS makes contact with the glasswere sealed with dry surface tension. The stamps were left in contact with the glass coverslips while they were exposed to 120 seconds of $O_2$ plasma treatment at a power of 50 W. During this time, the plasma makes contact with the glass everywhere except for the regions obscured by the PDMS stamp. The $O_2$ plasma alters the glass surface chemistry making it more hydrophilic in these exposed regions. After treatment, the stamps were removed, and a solution of 40 µg/ml laminin was added to the glass coverslip. The differential surface hydrophilicity resulting from the plasma exposure is sufficient to drive laminin deposition selectively on the plasma-treated regions, generating a surface pattern of laminin adsorbed from the solution.

Topographical Patterning

Topographical patterns were created on 1 mm thick glass slides in SU-8 2025 photoresist (PR) using standard photolithography processes. Briefly, glass substrates were cleaned with sequential 10 min washes in acetone, isopropanol, and DI water, and dehydrated in a convection oven for 30 min at 130° C. PR was spin-coated onto the glass substrate to a depth of 40 µm. The chips were soft-baked for 1 hr at 45° C., at which point the temperature was cycled twice from 95° C. to 45° C. for min each before being held at 95° C. for 2 hr and slowly cooled to 25° C. Photoresist was then exposed to 5 cycles of UV light at a dosage of 45 mJ/cm$^2$ through a transparency mask bearing the topographical pattern. Post-exposure bake consisted of a slow ramp to 95° C. for 30 min, followed by a slow cool to room temperature. The pattern was developed in SU-8 developer followed by a quick rinse in acetone, and chips were completed by hard baking them for 1 hr at 150° C. All heating steps were performed on a programmable hot-plate unless otherwise stated. A pattern of open-ended parallel grooves was used.

MEA Recording and Data Analysis

Recordings of spontaneous cellular activity were made on a heat-controlled stage at 37° C. in room atmosphere using a standard MCS recording array, sampling extracellular voltage from 60 contact pads at 20,000 Hz. In dissociated neuronal culture, contact pad spacing was 200 µm and diameter was 10 µm. For recording from explants, more spatial specificity was achieved by using an MEA with contact pad spacing of 100 µm and diameter of 10 µm. Recordings of dissociated cultures have been made from DIV 14 to DIV 35. Results from a 2 min section of data recorded on DIV 21, by which point spontaneous activity has fully developed, are shown. Recordings from explant culture were collected from DIV 7 to DIV 21. Data are shown from DIV 7 to emphasize how rapidly spontaneous activity appears in explant culture.

Individual EAPs were identified in the extracellular voltage trace (EVT) recorded on each electrode using a thresholding algorithm. The threshold was set by hand for each channel to account for the different levels of background noise. While the time of each EAP was recorded, PCA-based spike sorting was not performed because the primary interest is in the location of each spike in the 8×8 electrode grid rather than in its biological origin. The relative activity recorded by each electrode contact is calculated as the total number of spikes recorded on that electrode. This information is displayed as a color-scaled heat map for each culture type in which each square represents an electrode's position in the 8×8 grid, and its color encodes its activity level.

Spatial Localization of EAPs in Dissociated Cortical vs. Spinal Cord Explant Culture FIG. 22(A) shows dissociated cortical neurons at 225,000 cells/cm$^2$ on an embodiment MEA (contact spacing=200 µm). FIG. 22(B) is a raster plot showing 30 sec. of activity of culture in A at DIV 21. FIG. 22(C) shows the spatial distribution of activity shown in B. FIG. 22(D) shows a spinal cord explant culture in which the explant has been positioned such that cell bodies overlie three electrodes in the top row of an embdoiemnt MEA (contact spacing=100 μm), and axonal outgrowth extends over the rest of the contacts. FIG. 22(E) is a raster plot showing 30 sec. of activity of culture in D. FIG. ww(F) shows the spatial distribution of activity shown in E.

There is a morphological difference between dissociated cultures and explant cultures. In dissociated culture, both neuronal cell bodies and neuritic extensions are evenly and randomly distributed over entire recording surface (FIG. 15(A)), while in explant culture the neuronal cell bodies and neuritic outgrowth overlie separate recording sites (FIG. 15(D)). Both culture types exhibit primarily bursting activity, in which spike trains of closely spaced EAPs are generated on several electrodes simultaneously (FIG. 15(B and E)). Spontaneous bursting activity appears noticeably sooner in explant culture (as early as DIV 7) compared to dissociated cultures, which typically begin showing spontaneous activity around DIV 14. This difference is likely caused by neurons in the explant body being much more closely associated with one another and their respective support cells than is the case in dissociated culture.

Within the context of structured co-cultures, the most important difference between the two culture systems is apparent in the spatial distribution of EAP activity. Dissociated culture shows activity at a variety of locations randomly spread over the recording surface (FIG. 15(C)). This is because cell bodies are located near each recording site and are capable of synaptic communication with essentially any other cell in culture. As a result, any two electrodes may be a part of a network. In comparison explant EAP detection is limited to those electrodes directly underneath the explant body (FIG. 15(F)). While the neuronal signals generated by these neurons are certainly transmitted along the axonal outgrowth, they do not produce a large enough EAP to be detected using planar electrode arrays. As a consequence, EAP detection is limited to a single, highly localized area associated with the explant body.

Axonal and Dendritic Outgrowth from Spinal Cord Explants

FIG. 16(A) shows an SC explant isolated from E15 rat embryo. Explants were fixed on DIV 8, and stained with antibodies to MAP2 (green) and Tau46 (red). FIG. 16(B) is a graph of the average distance of maximum axonal extension from explant body in standard NB medium and NB containing 1 μM Ara-C. Error bars represent standard error of the mean.

Although the neuritic outgrowth from the spinal cord explant does not generate detectable EAPs, it is desirable to determine their axonal or dendritic identity in order to confirm whether these processes are likely to conduct information to distant targets and to estimate how distant these targets can be while still hoping to make synaptic contact. Following staining for axonal and dendritic markers (FIG. 16(A)), it is observed that the vast majority of outgrowth is axonal, and these axons fasciculate in similar fashion to their behavior in situ. This ordered and semi-directed outgrowth is not observable in dissociated cultures, where axons from individual cells tend to grow independently. Furthermore, the extent of axonal projection was far greater than that observed for dissociated neuronal culture with an average of 1.4 mm maximum axonal outgrowth (FIG. 16(B)).

As the intended use of the explants will be in co-cultures of primary cells, Ara-C can be used to knock down the number of contaminating fibroblasts or other proliferative cell types, thereby enriching for post-mitotic neurons and myotubes. As such axonal outgrowth length was quantified in both the presence and absence of 1 μm Ara-C, which was added to the medium. After 13 days in culture the presence of Ara-C in the medium did not appreciably reduce axonal outgrowth (FIG. 16(B)).

Figure 17:
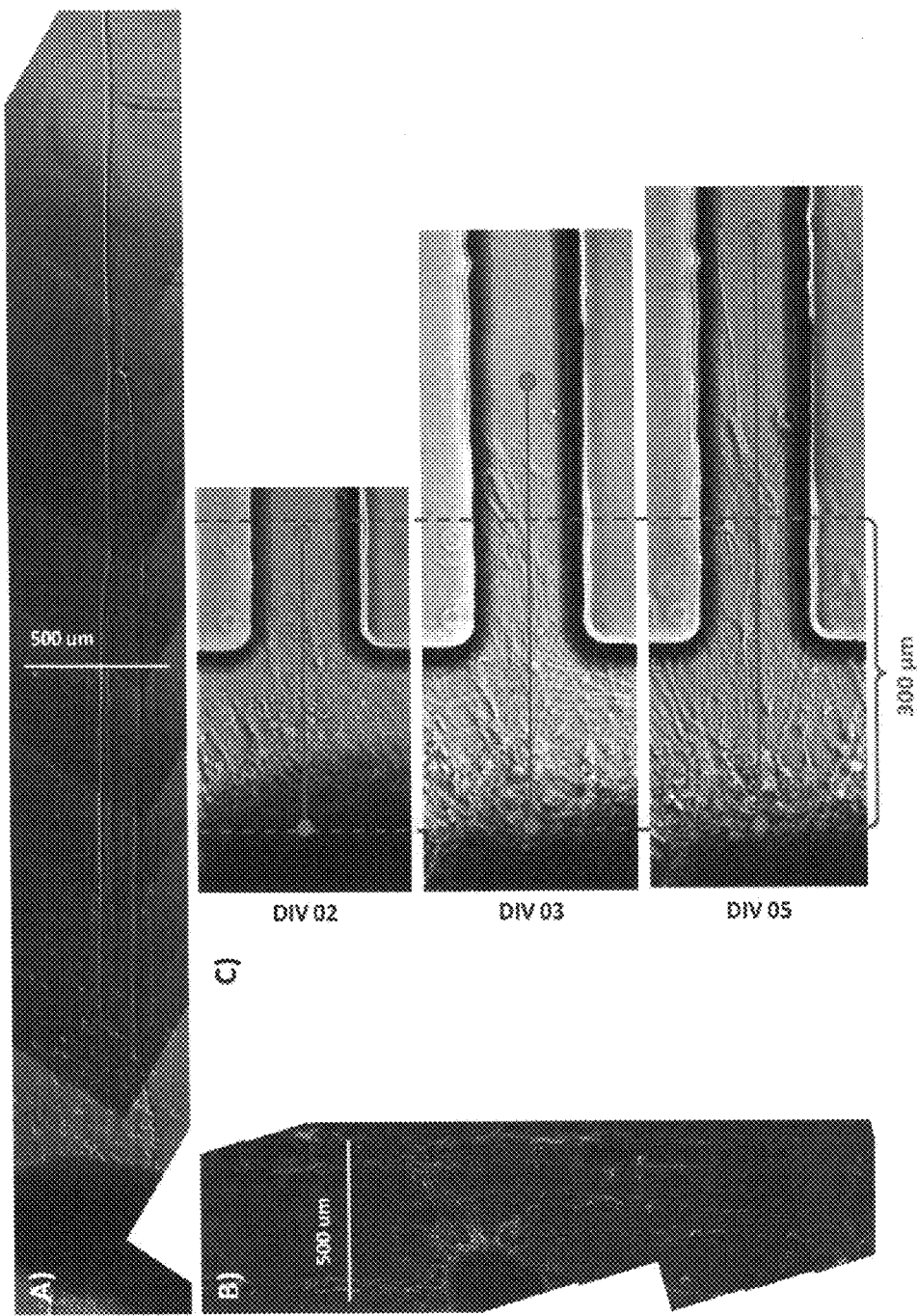
FIG. 17 shows topographical and chemical guidance of explant outgrowth.

FIG. 17(A) shows hippocampal explant at DIV12 interacting with laminin stripes deposited on a PEI-coated glass coverslip using a microfluidics/evaporation based technique. FIG. 17(B) shows spinal cord explant culture at DIV 11 grown on laminin stripes in NB prepared using a combined microfluidic/evaporation procedure rather than the traditional u-PIP plasma-based procedure. FIG. 17(C) shows explant outgrowth on topographically patterned substrate.

Chemical or topographical cues may be required to create structured co-cultures, so the feasibility of both techniques in directing axonal extension was examined qualitatively. Chemical cues are able to guide the direction of axonal outgrowth. However, axons are able to cross the space between the patterned lines, especially in the region close to the explant (FIG. 17(A and B)). Topographical cues are also able to guide neurite outgrowth and show less crossing between lanes than present on the chemical patterns, likely because the large physical obstruction represents a greater barrier to growth (FIG. 17(C)).

Skeletal Myotube Integration with Planar Microelectrode Arrays In Vitro for Spatially Selective Recording and Stimulation Myotube and Neuronal Isolation and Culture Myoblasts were isolated and cultured as known in the art. Briefly, pregnant Sprague Dawley rats were sacrificed by $CO_2$ inhalation at gestational day 21 and pups were removed by Cesarean section. Hind limb muscles were removed, and tissue was finely minced and digested (20 min at 37° C.) in PBS containing 1.5 U/ml collagenase (type D, Roche, Mannheim, Germany) and 2.5 U/ml dispase (type II, Roche, Mannheim, Germany). Single cells were separated from debris, pelleted by centrifugation, and resuspended in growth medium consisting of Ham's F-10 medium plus 20% fetal bovine serum, 1% Penicillin/Streptomycin, (all from Invitrogen, Carlsbad, Calif.) and 2.5 ng/ml human b-FGF (Promega Corporation, Madison, Wis.). Cells were then plated into 75 $cm^2$ flasks and incubated for 24 hrs. Adherent cells were resuspended and plated onto MEAS (Multichannel Systems) in differentiation medium consisting of Neurobasal medium including 2% B-27 Supplement, 1% Penicillin/Streptomycin, and 1% GlutaMAX (all from Invitrogen, Carlsbad, Calif.) at a surface density of 300,000 or 200,000 cells/$cm^2$ for recording and stimulation experiments, respectively. Prior to seeding, surfaces were coated overnight with 40 μg/ml laminin (Sigma Aldritch, St. Louis, Mo.).

Cortical neurons were isolated as known in the art. Briefly, pregnant Sprague Dawley rats were sacrificed by $CO_2$ inhalation at gestational day 18 and pups were removed by Cesarean section. Cortex was isolated, meninges removed and a single cell suspension was prepared by triturating the cortex with a flame-polished glass pipette. Cortical cells were then seeded onto MEAS in MEM medium plus 1% penicillin/streptomycin, 10% horse serum, and 3% v/v of 20% glucose solution at a surface density of 225,000 cells/$cm^2$. Prior to use, the medium was glutamate-depleted by 24 hr exposure to astrocytes in culture, and the MEA surface was treated overnight with 3% PEI dissolved in borate buffer.

Acquisition and Analysis of Electrophysiological Data

Recordings of spontaneous cellular activity were made on a heat-controlled stage at 37° C. at room atmosphere using a standard MCS recording array, sampling extracellular voltage from 60 contact pads at 20,000 Hz. Contact pad spacing was 200 μm, and diameter was 10 μm. Recordings of myocyte cultures were made at DIV 12 and 14, a window during which spontaneous contractile activity was maximal. Recordings of cortical neurons were made on DIV 21 after neurons have had time to establish mature synapses and network dynamics.

Spike sorting was performed using custom algorithms composed in a MATLAB environment. Briefly, potential spikes were identified using a voltage threshold of 5× the RMS noise for each channel. All spikes were aligned to their point of maximal deflection based on a window 2 ms preceding and 4 ms following the threshold break-point, and principal component analysis PCA was performed on the resulting set of vectors. Using their position in a 2D space based on the first two PCs, likely spike events were then clustered using a K-means algorithm. The clustering process was user-guided, where the experimenter identified the starting number of clusters, and was then able to split and join clusters iteratively until spikes were correctly classified based on visual investigation. Because each cell produces action potentials with a unique shape, each of the resulting clusters represents the activity of a single cell (or "unit") as its activity is recorded in the extracellular voltage trace (EVT) from a single electrode. Metrics of spike characteristics were then calculated based on the morphology of the average spike shape for each unit. In our case, SNR is the ratio of the peak-to-valley amplitude of a spike shape to the RMS noise recorded on that electrode, and the Unit SD is the average SD along the 6 ms window surrounding the point of maximal deflection.

Analysis of Contractile Activity

An unordered myotube culture was grown on a commercially available MEA. On DIV 7 stimulation at selected electrode sites was delivered using an MCS signal generator and associated software. 10 Cycles of a 2V biphasic pulse with a 40 μs duration was delivered across sets of 2 or 4 electrodes. This regime was repeated with a frequency of 1 Hz. Videos of cells were acquired using the Qcapture-pro software at a frame rate of frames per second. Automated localization of contractile activity was performed as discussed above. Briefly, videos were analyzed using a series of image processing steps and pattern recognition steps, which make it possible to identify regions of synchronized contractility within videos of myotube cultures, returning the location of the contractile myotubes as well as their pattern of contractions.

Myotube vs. Neuronal Extracellular Action Potentials

Myoblast differentiation into myotubes occurred on MEA surfaces. The myotubes form long, overlapping tubular structures, approximately 20 μm to 40 μm across and up to several mm in length (FIG. 18(A)). By comparison, neurons are in the range of 20 μm in diameter, with an accompanying neuritic arbor which can reach longer lengths (FIG. 18(B)). Both cell types are electrogenic, creating transmembrane currents through roughly similar processes. The unique membrane composition, morphology, and behavior of each cell type, however, results in different EAP characteristics.

FIG. 18(A) shows myotube morphology on an embodiment MEA at DIV 12. A single myotube is outlined in red dashes, and the area over which it's EAP is likely detectable is shaded in red. FIG. 18(A1-A3) show representative myotube EAP shapes following spike sorting (6 ms shown, variable y-axis scale). FIG. 18(B) shows neuronal morphology on an embodiment MEA at DIV 21. FIG. 18(B1-B3) show representative neuronal EAP shapes following spike sorting (6 ms shown, variable y-axis scale). FIG. 18(C) is a scatter plot showing maximum positive deflection vs. maximum negative deflection for each unit. FIG. 18(D) illustrates average positive and negative deflections over all units. FIG. 18 (E) illustrates average signal to noise ratio (SNR) over all units. FIG. 18(F) illustrates average unit standard deviation over all units. All error bars represent the standard error of the mean.

The shape of the EAP is primarily a result of the spatial relationship between the cell and the electrode contact. Neurons have static surface interactions over short periods of time, and recordable EAPs are primarily generated by the soma, which results in stereotyped EAP shapes like that pictured in FIG. 18(B.3). The predominance of EAPs that are negative and essentially unipolar is shown in FIG. 18(C) by the large number of neuronal points appearing below the dashed line. Bipolar (FIG. 18(B2)) and unipolar (FIG. 18(B3)) EAP shapes may also be seen by recording from proximal neurites, but the vast majority of neurites are too small to produce a detectable signal without special modifications. In comparison, the EAPs generated by myotubes are far more variable. Standard unipolar and bipolar EAPs are possible (FIG. 18(A1-red and green)) but arbitrary shapes are more frequent (FIG. 18(A1-3). This is likely due to the longer period over which the depolarization occurs, the propagation of the intracellular action potential along the myotube, and the changing shape and location of the myotube during excitation and contraction. This variability is reflected in the greater scatter of the myotube points in FIG. 18(C). Despite the variability in spike shape, spikes generated by a single biological unit are remarkably reproducible, as evidenced by the small within-unit variability (FIG. 18(F)).

Myotubes and neurons produce EAPs with similar amplitudes (FIG. 18(D)). However, due to the variability between cultures, and even between electrodes within the same device, a direct comparison between myotube and neuronal EAP signal strength can only be made by normalizing the peak-to-valley amplitude of each unit by the noise associated with the electrode contact on which it is recorded. This analysis shows that myotube spikes tend to have a higher SNR than neuronal spikes. Current theories suggest that this is due to a combination of two effects stemming from the increased size of myotubes relative to neurons: 1) increased extracellular voltage change caused by the larger ionic movement accompanying depolarization and 2) improved electrode sealing and coverage due to the larger surface area contacted by myotubes.

Myotube Network vs. Neuronal Network Activity Patterns

A striking feature of culture behavior for each cell type is the synchronous activation of multiple units, which appears as vertical bands of events in FIG. 19. This culture-level behavior has different root causes for myotubes and for neurons. Many myotubes are large enough to pass within recording distance of multiple electrodes (FIG. 18(A)). Therefore a single myotube will frequently create EAPs that register as units on multiple electrodes. When the myotube depolarizes, each of these units registers a single event at the same time, causing the vertical banding in the raster plot of culture activity. The vertical banding therefore exists as a line of single events occurring at essentially the same time (FIG. 19(C)).

In contrast, single neurons will only ever be within recording distance of a single electrode (FIG. 18(B—red field)). Because of their far-reaching processes, however, it is possible for neurons to be synaptically connected with other neurons. As waves of activity travel through these multicellular networks, it produces synchronous activation of multiple electrodes as multiple neurons, each one within the recording field of a different contact, are activated. As such, the precise activation pattern of each unit in the network is unique (FIG. 19(D)). Overall activity is driven by the network, so the activity of all net-worked units generally overlaps, but there is a much less clear cause-and-effect relationship between individual events on separate electrodes than exists with myotubes.

In FIG. 19, rast plot axes show the time (X-axis) and unit number (Y-axis) of each EAP as a point. The raster plots of FIG. 19 show 30 sec. of data recorded from a myotube culture at DIV 12 FIG. 19(A), 30 sec. of data recorded from a neuronal culture at DIV 21 FIG. 19(B) and an expanded view of 1 sec of data segments from within A and B as indicated by the red rectangle FIG. 19(C) and FIG. 19(D) taken from FIG. 19(A) and FIG. 19(B), respectively). Two example networks are shown in each case.

It is noted that multiple networks coexist in the same culture (both in myotube cultures and neuronal cultures) as do units that are active independently from any other units. Each network's activity is observable as the synchronous activation of a different set of units (FIG. 19(B-C-blue and green rectangles)). Coexisting networks in neuronal culture are expected, due to the large number of available neurons and the structured and specific way synapses are formed and pruned. The behavior is surprising in myotubes, however, where disordered culture tends to produce multipolar or branching myotubes that contract as single entities and where the precedent set by cardiac myocytes is the formation of mass syncitia. If myotubes fused with all other contacted myotubes, the result would be a single contractile entity, as in cardiac myotubes. The existence of multiple myotube networks within an unstructured culture suggests that myotube fusion is a directed process which proceeds with some specificity.

Selective Stimulation of Myotube Networks

Figure 20A:
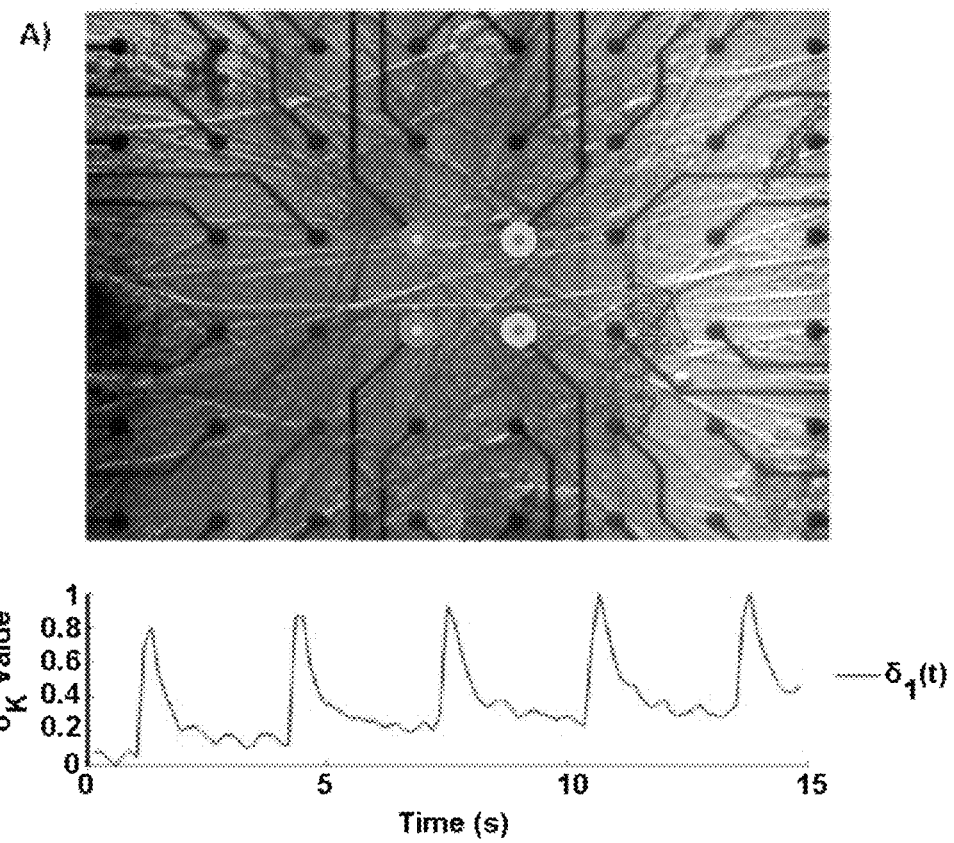
FIG. 20 illustrates stimulation of myotube networks using an embodiment substrate-embedded MEA.

The discovery that multiple independent myotubes are identifiable by their pattern of spontaneous bio-electrical activity, and that their independence is conserved even when they may partially overlap, led to an investigation of whether the myotube networks can be selectively stimulated. Stimulation of a central region of the culture resulted in contraction of multiple myotubes within the culture (FIG. 20(A)), paced along with the stimulus. Stimulation of more peripheral regions, however, triggered contraction only of selected cells within the culture (FIG. 20(B-D)). Stimulation of an intermediate area between two of these cells resulted in simultaneous activation of both (FIG. 20(E)).

In FIG. 20, active myotubes are identified based on automated analysis of video-micrographs, and indicated by the colored meshwork, and the electrodes used for stimulation are indicated by the orange and yellow dots. FIG. 20 (A) shows stimulation in a central region, triggering contraction in a large area of the overlying myotube layer. FIG. 20(B-D) shows stimulation at peripheral sites, showing activation of subsets of myotubes. FIG. 20(D) shows stimulation at an intermediate site, showing activation of the myotubes from FIG. 20(C) and FIG. 20(D).

Temporally selective myotube stimulation has been demonstrated, as has the spatially selective stimulation of neuronal preparations. However this is the first demonstration of spatially selective stimulation of myotubes and the subsequent contraction of a selected subset of cells in the culture. This finding reinforces the notion that multiple independently active myotubes can coexist in the same culture, even when they may be in direct physical contact with one another at points along their length. It also confirms the ability to use MEA technology to selectively stimulate contraction in specific myotube net-works without stimulating those around them. Spatially-selective stimulation frees researchers from dependence on spontaneous contractility or bulk stimulation as a means of observing contractile activity in skeletal muscle cell preparations.

Conclusions:

By integrating a skeletal myotube culture with a substrate embedded MEA, spontaneously contractile myotubes are capable of producing activity that is detectable both optically and electrically. Skeletal myotubes have EAPs with SNR similar to those recorded from neuronal somata cultured under similar conditions. However, myotube EAPs are longer in duration and can be multiphasic, while neuronal depolarizations are rapid, small, and predictably monophasic. The activity of each cell can be identified based on its unique EAP signature, and the activity of single myotubes spanning multiple electrode contacts can be observed as linked activity between these units. Additionally, multiple independently active myotubes exist in the same culture despite physical contact with other myotubes and can be distinguished optically based on contraction or on the network-like behavior of the underlying electrodes.

Microdevices with integrated cellular components can be classified based on whether they are used to sense or induce cellular activity and on the whether they have clinical or laboratory applications. The integration of skeletal myotubes with MEAS has implications in each of the categories above. The ability to monitor myotube excitation and contraction during development and over extended periods provides new insight into development and diseases of the neuromuscular system. The ability to trigger specific myotubes in a culture provides a method of control over microscale biorobotic actuation. Most interesting is the ability to combine skeletal myotube cultures with neuronal cultures on MEAS. Integration of motoneuron-myotube co-cultures with an MEA substrate provides researchers with a sensitive means of observing the NMJ, unraveling the complicated trophic communication occurring between motor neurons and myotubes and observing simple neuronal circuit formation, such as the spinal reflex arc.

It also opens the door to new approaches to neural interfaces. One can conceptualize a neural interface designed to restore conscious motor control of prosthetic devices based on using individual myotubes as biological signal amplifiers for motor intention carried along regenerated motor fibers. Using a myotube-integrated MEA provides regenerating motor axons with a neurotrophin-secreting target for reinnervation. Recording EAPs from myotubes onto which PNS axons had successfully regenerated solves problems associated with recording from peripheral motor axons because of their small size, inducing and maintaining neurite ingrowth into regenerative electrodes, and isolation of a large number of motor signals from other neural activity carried in the PNS. Such an approach increases the communication bandwidth of the targeted muscle reinnervation approach by reducing it to a single cell scale. Other embodiments include the integration of an MEA with topographical guidance cues in order to create structured myotube cultures, and ultimately, facilitate the formation of structured motor neuron-myotube co-cultures.

Figure 21:
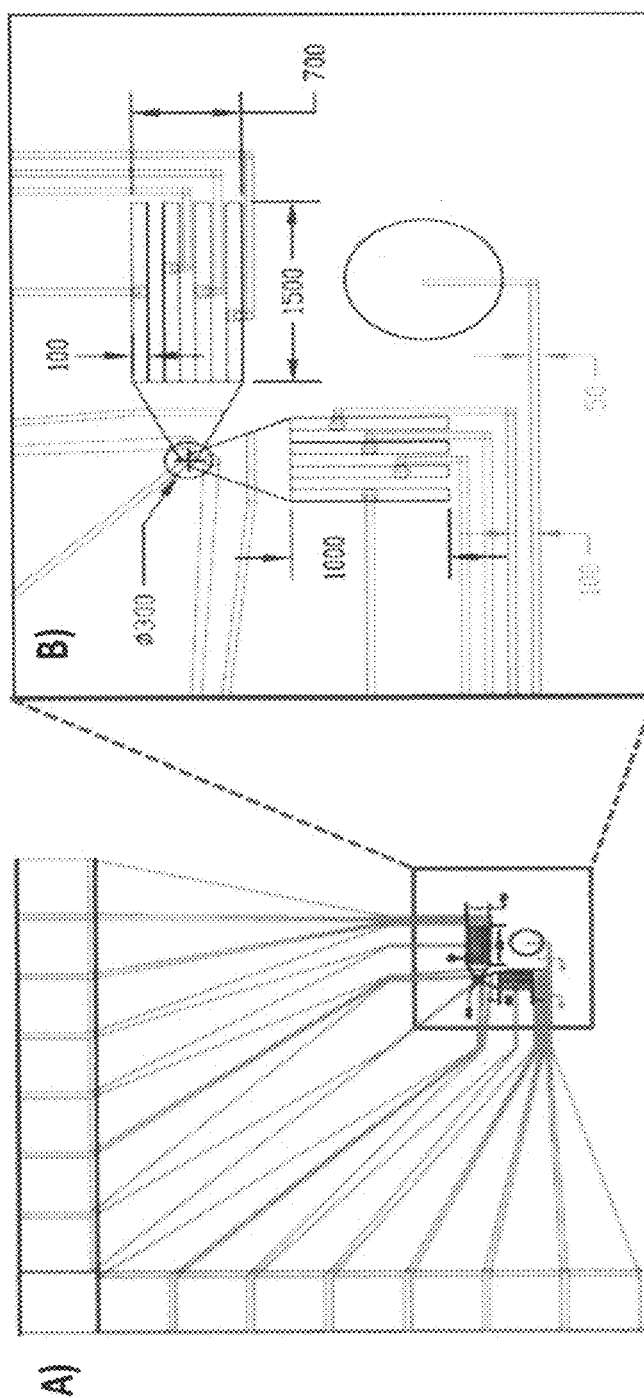
FIG. 21 is a schematic of an embodiment myo-MEA.

Topographically Modified Substrate-embedded MEA for Directed Myotube Formation at Electrode Contact Sites Device Fabrication FIG. 21 (A) illustrates an upper-left quadrant of an embodiment device, showing connections between 1 of the 4 recording fields and the external electrical contact pads. FIG. 21(B) is a detailed view of a recording field from FIG. 21(A). Gold conducting features are shown in orange, while SU-8 topographical features are shown in blue. All units are in $\mu$m.

An embodiment device was designed incorporating topographical modifications that direct myotube formation and spinal cord explant (SCE) outgrowth with a substrate embedded MEA. Specifically, two regions of trenches used to direct myotube formation to specific electrode sites are connected to a central field for a spinal cord explant (SCE), which is spatially separated from the grooves to allow neuron/myotube contact only through axonal outgrowth (FIG. 21(B)). The two wing regions, oriented horizontally and vertically, include four grooves with a single electrode contact at the bottom. The central field contains 5 recording electrodes to record from multiple points beneath the explant body and axonal outgrowth. A large pad is included as an internal reference electrode (not shown). The electrodes are patterned to interface with a Multi-channel Systems MEA recording head-stage through external con-tact pads located around the periphery of the chip (FIG. 21(A)).

The electrode contact and lead pattern can be produced using a lift-off technique. Briefly, a layer of photoresist (PR) bearing the electrode pattern is produced using standard optical lithography. The PR is then undercut using a short hydrofluoric acid (HF) etch followed by sputtering of a 200/700 Å thick chromium/gold (Cr/Au) conducting electrode layer. The PR is dissolved in acetone removing the conducting layer everywhere except the electrode pattern. A SU-8 PR layer is spin-coated on the electrode-patterned surface, exposed and developed using a topographical feature mask to generate topographical trenches and central confinement regions and selectively exposing the electrode contact pads located at the bottom of both while leaving the electrode leads electrically insulated from the culture environment. A PDMS ring is affixed to the surface, creating a culture chamber around four recording fields, enabling multiple simultaneous experiments.

Myoblast Isolation and Culture

Myoblasts were isolated and cultured as known in the art. Briefly, pregnant Sprague Dawley rats were sacrificed by $CO_2$ inhalation at gestational day 21 and pups were removed by Cesarean section. Hind limb muscles were removed, and tissue was finely minced and digested (20 min at 37° C.) in PBS containing 1.5 U/ml collagenase (type D, Roche, Mannheim, Germany) and 2.5 U/ml dispase (type II, Roche, Mannheim, Germany). Single cells were separated from debris, pelleted by centrifugation, and resuspended in growth medium consisting of Ham's F-10 medium plus 20% fetal bovine serum, 1% Penicillin/Streptomycin, (all from Invitrogen, Carlsbad, Calif.) and 2.5 ng/ml human b-FGF (Promega Corporation, Madison, Wis.). Cells were then plated into 75 $cm^2$ flasks and incubated for 24 hrs. Adherent cells were resuspended and plated onto MEAS (Multichannel Systems) in differentiation medium consisting of Neurobasal medium including 2% B-27 Supplement, 1% Penicillin/Streptomycin, and 1% GlutaMAX (all from Invitrogen, Carlsbad, Calif.) at a surface density of 300,000 cells/$cm^2$. Prior to seeding, surfaces were coated overnight with 40 μg/ml laminin (Sigma Aldritch, St. Louis, Mo.).

Electrophysiological and Optical Data Acquisition and Analysis

Recordings of spontaneous cellular activity were made on a heat-controlled stage at 37° C. at room atmosphere using a standard MCS recording array, sampling extracellular voltage from 60 contact pads at 20,000 Hz. Contact pad spacing was 200 μm, and diameter was 10 μm. Recordings of myocyte cultures were made at DIV 14, when spontaneous contractile activity is maximal. Spike sorting was performed using custom algorithms composed in a MATLAB environment and based in part on the algorithms discussed in Adamos, et al., *Comp Meth Prog. Biomed.*, 91(3), 232-244 (2008). Briefly, potential spikes were identified using a voltage threshold of 5× the RMS noise for each channel. All spikes were aligned to their point of maximal deflecttion based on a window 2 ms preceding and 4 ms following the threshold break-point, and principal component analysis (PCA) was performed on the resulting set of vectors.

Using their position in a 2D space based on the first two PCs, likely spike events were then clustered using a K-means algorithm. The clustering process was user-guided, where the experimenter identified the starting number of clusters, and was then able to split and join clusters iteratively until spikes were correctly classified based on visual investigation. Because each cell produces action potentials with a unique shape, each of the resulting clusters represents the activity of a single cell (or "unit") as its activity is recorded in the extracellular voltage trace (EVT) from a single electrode. Metrics of spike characteristics were then calculated based on the morphology of the average spike shape for each unit. In one embodiment, SNR is the ratio of the peak-to-valley amplitude of a spike shape to the RMS noise recorded on that electrode, and the Unit SD is the average SD along the 6 ms window surrounding the point of maximal deflection.

To dynamically analyze contractile activity of myotubes, videos of cell behavior were acquired after the onset of spontaneous contractility and were analyzed as described above. Briefly, videos were analyzed using a series of image processing and pattern recognition steps which made it possible to identify regions of synchronized contractility within videos of myotube cultures. These locations are then taken to be the location of the contractile myotubes.

Device Characterization

Figure 22:
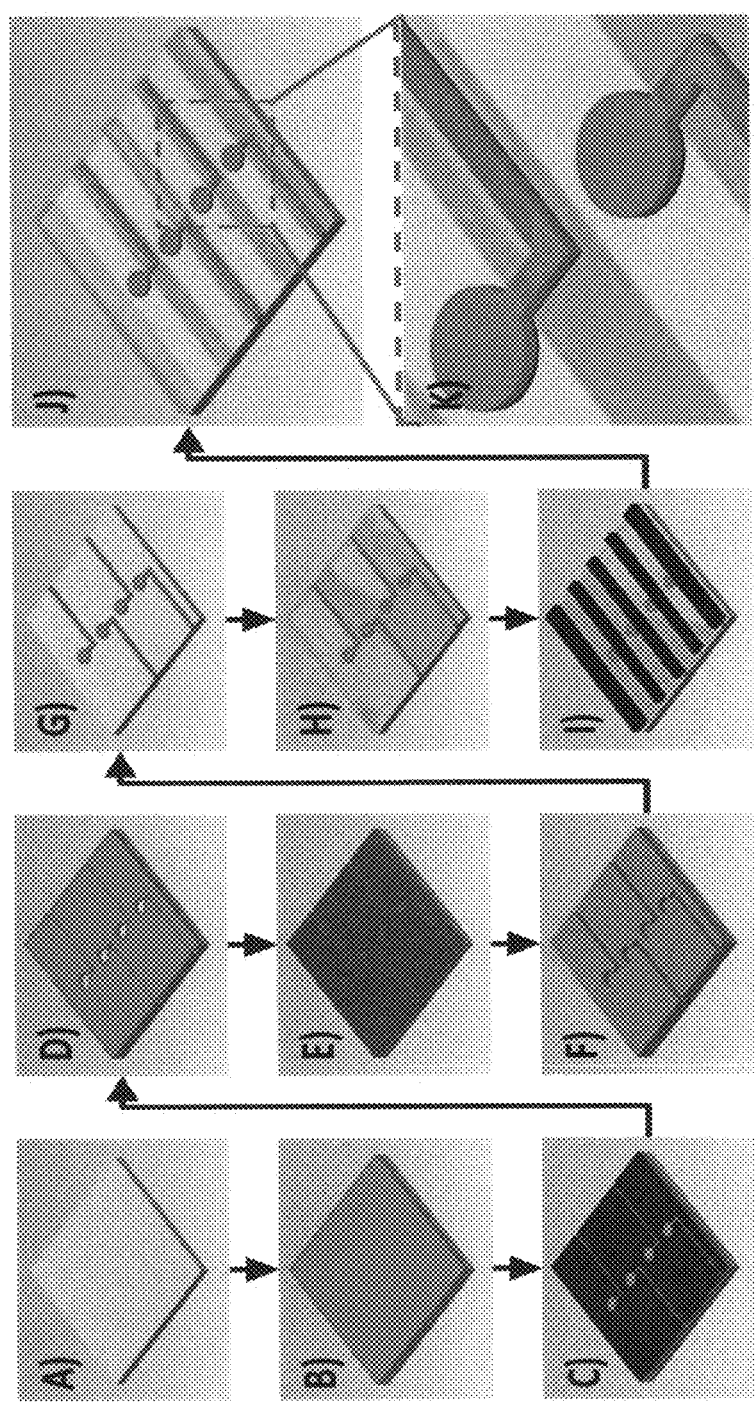
FIG. 22 shows an embodiment myo-MEA device.

FIG. 22(A) is a microscopic view of an embodiment recording field schematized in FIG. 21(B). FIG. 22(B) shows an embodiment prototype, including a PDMS culture chamber. The embodiment fabrication process generates devices capable of recording myotube and explant EAPs and withstands repeated cycles through the sterilization-usage-regeneration processes involved in cell culture (FIG. 22(A-B)). In examinations of the electrode noise-floors (data not shown), it was determined that the gold leads establish electrical continuity between the recording contact sites and the external contacts which interface with the MCS head stage. Electrode noise was low (~3 μV) for functional electrodes, while it was elevated to the maximum noise detectible using the MEA recording array (~40 μV) where electrode continuity with the culture fluid was lost (either by scratching the lead under the SU8 insulating layer or through incomplete development of trenches). The SU8 layer has good adhesion properties, without cracking or delamination flaws (FIG. 22(A)). Additionally the SU8 layer is optically clear, facilitating the observation of culture conditions in and around the experimental fields. Final prototypes have 4 recording fields inside of the PDMS culture ring, enabling parallel experiments (FIG. 22(B)).

Myotube Formation Guided by Trenches

Figure 23:
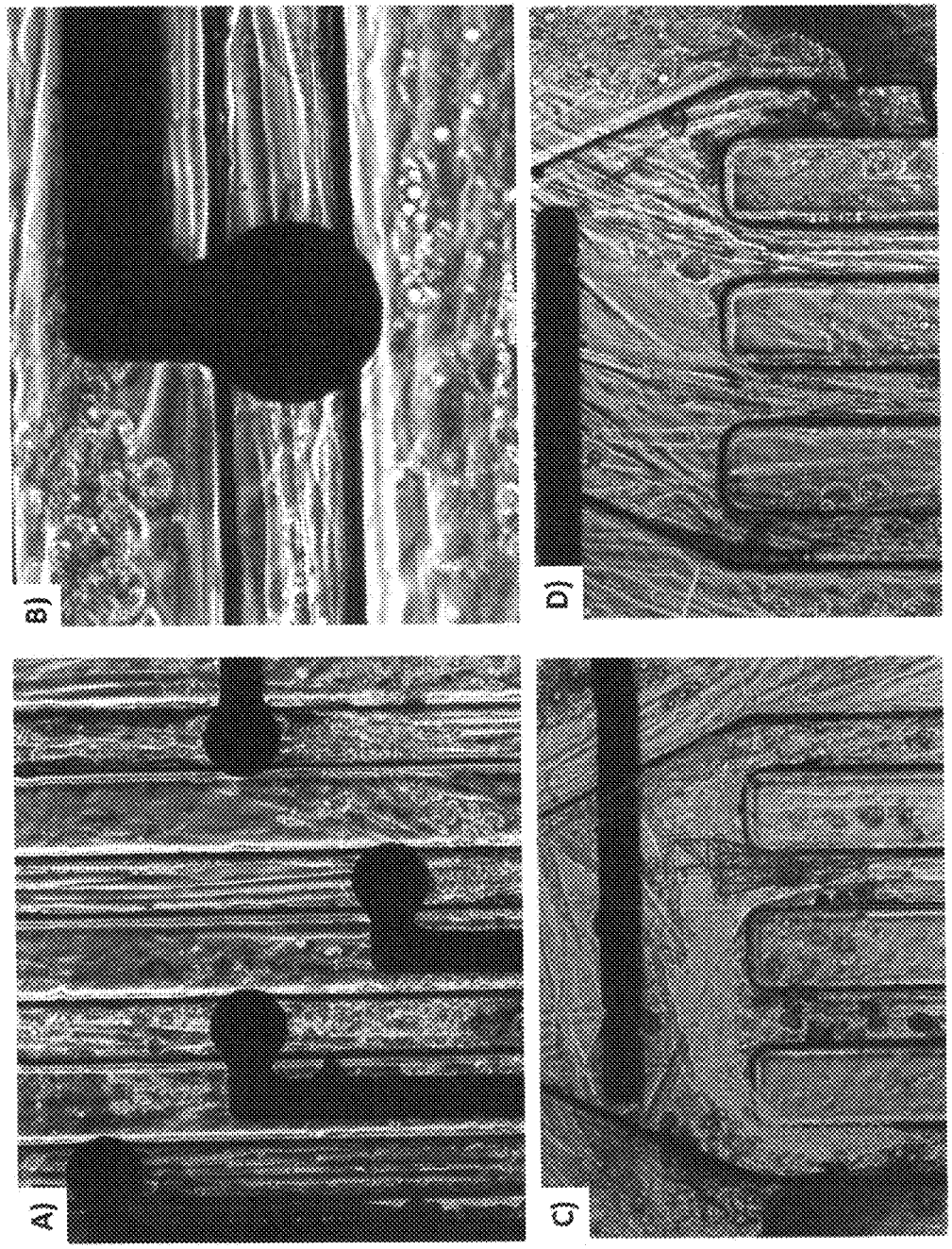
FIG. 23 shows myotube differentiation and guidance on embodiment myo-MEA topographical features.

FIG. 23(A-B) show myotubes lying along the bottom of trenches and on top of electrode contacts in an embodiment "wing" region. FIG. 23(C-D) shows myotube contractility funneled down embodiment trenches. Consistent with the above disclosure of the effects of microscale trenches on myotube morphology, topographical features constructed on top of the substrate embedded MEA direct myotube formation and morphology. Multiple myotubes are observed to form along the bottom of trenches, aligned in parallel with the major trench axis. Similarly, the topographical features are able to direct myotube contractility to the trenches. However, because these trenches are open ended and connect to a large open field, they have the interesting effect of funneling multiple myotubes to a single trench (FIG. 23 (D)), and of funneling separate "fingers" of a single myotube down multiple trenches (FIG. 23(C)).

Detection of Myotube EAPs

Figure 24A:
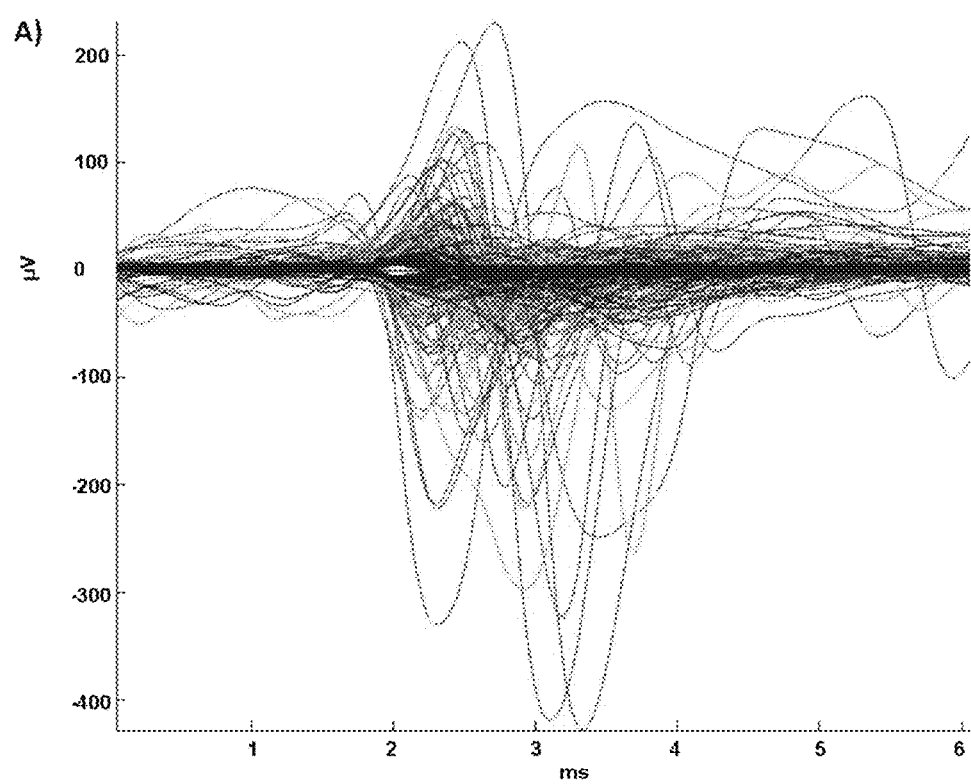
FIG. 24 shows embodiment myo-MEA recordings of myotube EAPs.

In FIG. 24 EAPs are detected from sister cultures grown on topographically patterned embodiment myo-MEA, uninsulated myo-MEA, and commercially available MEA. In the graph of FIG. 24(A) all units for each device are superimposed (6 ms of data shown). In FIG. 24(B) the average positive and negative deflection for all units are measured in μV. FIG. 24(C) shows the average SNR for all units. FIG. 24(D) shows the average unit SD for all units.

Various embodiments are able to use the topographically modified myo-MEA devices to record the bioelectrical activity of spontaneously active myotubes in similar fashion to commercially available MEAS. Spike sorting of the resulting extracellular voltage traces (EVTs) is possible, yielding unit-specific EAPs with high reproducibility and low intra-unit variance (FIG. 28(D)). A comparison was made of myotube EAP qualities measured on three different types of electrode; 1) topographically modified myo-MEAS, 2) the myo-MEA electrode pattern without the insulating topographical SU8 layer, and 3) commercially available MEAS. There is similar EAP morphology recorded on all substrates, exhibiting the characteristic multi-phasic and unpredictable EAP morphologies (FIG. 24(A)).

There is an amplification of EAP amplitude observed on the fully insulated prototypes (FIG. 24(B)) relative to both the uninsulated and the commercially available MEAS. This contributed to the insulated myo-MEA also providing EAP recordings with a larger SNR (FIG. 24(C)), however the effect is less than would be expected based on the larger amplitudes. The finding that the uninsulated myo-MEA electrode pattern also showed increased amplitude and SNR over the commercially available MEA is somewhat surprising, as theory would dictate that current leakage through the uninsulated leads and into solution would diminish the effective voltage recorded. However, in cultures this dense the overlying cell layer may provide some insulation, diminishing this current shunt. When combined with the much larger surface area available for recording, this may explain the increase in amplitude.

Changes in Myotube Dynamics Due to Topographical Modification

FIG. 25(A) shows 5 sec. of activity detected in four fields of a topographically patterned embodiment myo-MEA. FIG. 25(B) shows 3 seconds of data from a single recording field in which repeating activation motifs have been identified by hand. Activity is detected in four fields of an uninsulated embodiment myo-MEA during non-seizure-like (FIG. 25(C)) and seizure-like (FIG. 25(D)) activity. Recordings were made at DIV 14. Each raster plot includes four horizontal fields, representing each of the four recording fields. The electrodes in each field are color-coded according to location.

Using the spike sorted EAP data, it is possible to identify spatial and temporal patterns in myotube activation. These patterns of activity are affected by the topographical patterning of the electrode. FIG. 25(A) shows 5 seconds of data recorded from the 4 fields of a myo-MEA. Total activity is the result of a combination of repeating vertical banding patterns (generated by myotubes that span multiple trenches and the central region), and units that fire in isolation (generated by myotubes confined to a single trench). Obvious repeating activation motifs occurring in 3 seconds of data from a single recording field have been identified by hand (FIG. 25(B)).

The distribution of the synchronous bursting patterns is limited to each of the 4 recording fields (i.e., there is little activity that spans more than 1 recording field). By comparison to the insulated myo-MEA, there are two noteworthy observations about the EAP activity recorded by the uninsulated myo-MEA electrode pattern. There are more units recorded on it (a 20% increase over the insulated myo-MEA), and these units are have a higher activation rate.

This is consistent with the much larger recording field, which in the uninsulated myo-MEA includes the leads as well as the contacts. This larger electrode area records activity of all cells along its path, contributing to the larger number of units detected. Additionally, these units are active more frequently, and are capable of switching between "seizure-like" state, where every unit fires synchronously and rapidly, and more "non-seizure-like" state, where individual units and activation motifs can be identified. One possible explanation is that the culture is able to grow in an uninterrupted sheet in which every cell is mechanically coupled to every other cell. This may create a situation where contraction of a myotube mechanically triggers the contraction of neighboring cells, even though they may remain electrophysiologically distinct. The presence of the topographical cues may be enough to break up the mechanical coupling to the point that culture-wide "epileptic" events are no longer possible.

Structured Myotube Culture on a Topographically Modified Substrate Embedded MEA

To facilitate integration with spinal cord explants for the development of structured motor neuron-myotube cocultures, various embodiments may select topographical modifications in the form of two trench regions (for myotube formation) joined to a central region (designed for spinal cord explant adhesion and spreading). The topographical modifications are able to direct myotube formation and contractility, as detected optically, and the underlying substrate embedded MEA is able to record EAPs from the overlying myotubes, which can then be spike sorted to identify the activity of multiple individual myotubes recorded on a single electrode. Further, the topographical modifications induce a change in the quality of the EAPs observed which is consistent with current theories on cell-electrode interactions, and a change in the behavior of the myotube culture which is caused by the induced structure.

Other Embodiments in Co-culture

Spinal Cord Explant Culture on a Topographically Modified Substrate-embedded MEA Guides Axonal Outgrowth and Facilitates Selective Recording Various embodiment myo-MEA devices may be used as a co-culture system in which it is possible to observe the transmission of action potentials from a neuronal population to a myotube population. An embodiment device is representted schematically in FIG. 26, showing desired spatial relationships of the component cell types (FIG. 26(A)) along with modalities of data to be recorded from each location (FIG. 26(B-D)).

Figure 26A:
FIG. 26 illustrates coculture in an embodiment myo-MEA design.
Figure 26C:
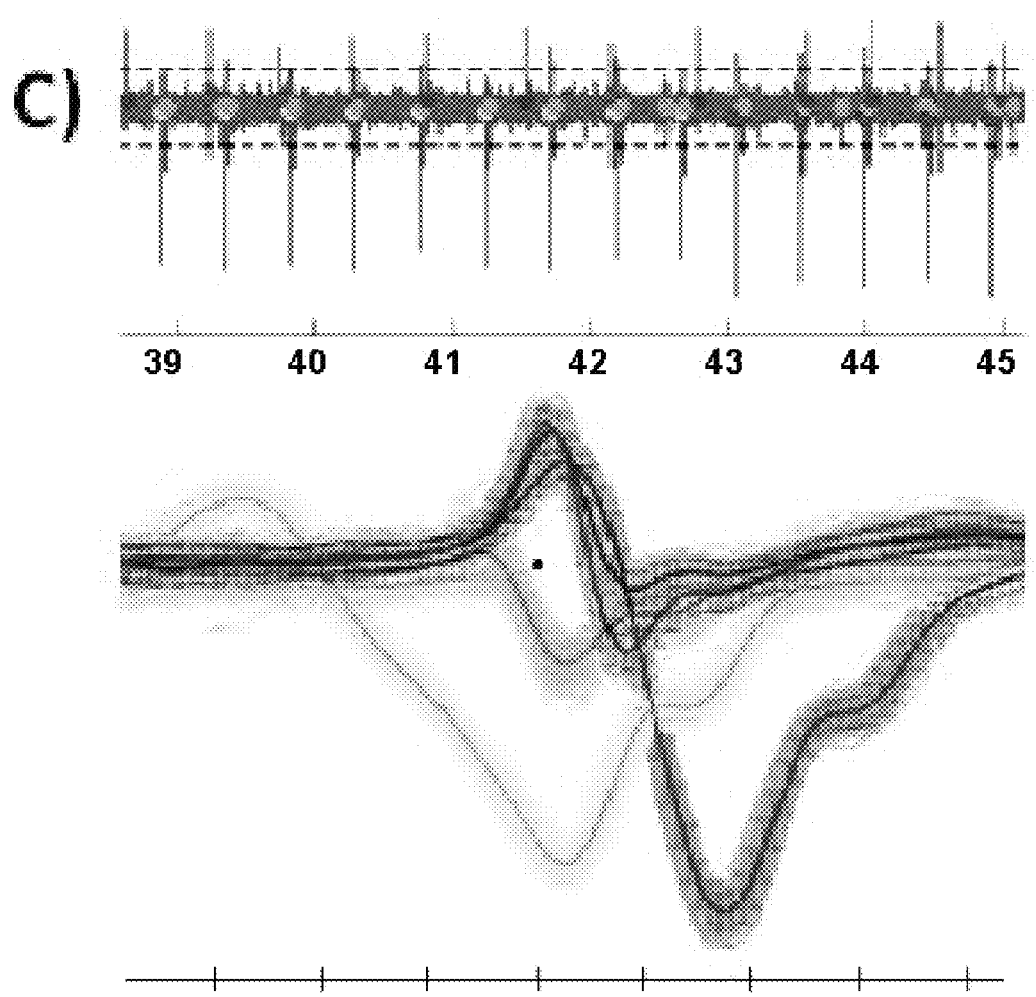
Figure 26D:
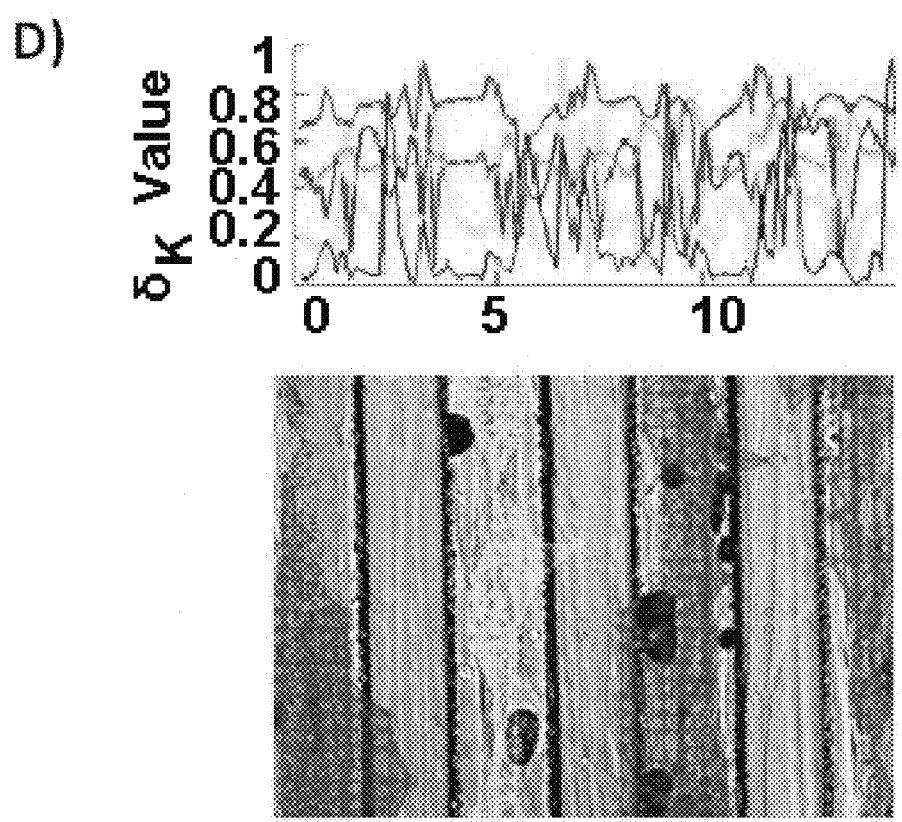

FIG. 26(A) shows the spatial relationship between an embodiment explant and myotube culture zones. FIG. 26(B) shows an example of an MEA-based identification of spatially confined explant EAPs. FIG. 26(C) is an example of identification and spike sorting of embodiment myotube EAPs. FIG. 26(D) shows identification of myotube contractility patterns in embodiment microscale topographical trenches.

A neuronal source with controllable architecture is appropriately selected and deployed in the device demonstrating localized extracellular actions. As discussed above, explants provide an ideal source of neuronal input because of the highly localized EAP activity and aggressive axonal outgrowth. As depicted in FIG. 26(A), these two qualities enable them to synaptically contact the trench-bound myotubes from the central explant region through axonal outgrowth. This enables the selective recording of explant EAPs from the central region, and myotube EAPs and contractions from the trench region. In one embodiment, explants were cultured on the central region of an embodiment myo-MEA recording field and monitored for axonal outgrowth, while recording from all electrodes to determine whether EAP activity is confined to the central region while axons infiltrate the trenches.

Example

Cell Culture

Spinal cord explants are prepared using procedures known in the art. Briefly, pregnant Sprague Dawley rats were sacrificed by $CO_2$ inhalation at gestational day 15, and pups were removed by Cesarean section. Spinal cord was removed posteriorly and transferred to a PDMS-lined petri dish, bisected longitudinally and finely minced transversely into sections 200-300 μm thick. Explants were plated on myo-MEAS, all of which had been adsorbed overnight with laminin at 40 μg/ml in 10 μL of medium, at which point they were precisely positioned in the central explant zone of each recording field. After 5 min, allowing for initial adhesion, enough medium was added to just cover the explant, and it was placed in an incubator at 5% $CO_2$ and 37 deg C. Medium was replaced every 2 days.

Spatial Distribution of Neuronal and Myotube EAP Sources Sources

FIG. 27(A) shows spinal cord explants (SCE) cultured in central region of 2 neighboring embodiment recording fields. FIG. 27(B) shows axonal guidance down embodiment trenches from DIV 2-5. FIG. 27(C) shows 5 seconds of bursting EAP activity recorded from embodiment explants in FIG. 27(A). FIG. 27(D) shows 5 seconds of myotube EAPs recorded from all 4 of an embodiment myo-MEA. In raster plots shown in FIG. 27(C) and FIG. 27(F), units are coded based on electrode location.

SCE adhere to the embodiment myo-MEA surface, with the explant body largely confined to the central region (FIG. 27(A)). By DIV 5, aggressive axonal outgrowth extends along the glass bottom and is guided down the topographical channels (FIG. 27(B)). By DIV 7 explant bodies generate spontaneous bursting activity detectable on the central region electrodes, consisting of multiple, rapid, EAPs (FIG. 27(C)). Bursting behavior was observed from multiple explants on the same myo-MEA, however, the distance between them is sufficient that their activity is not coupled. Additionally, explant EAP activity is bound only to the central region, and even up to an age of 3 weeks in culture explant bursting activity is never detectable on the trench electrodes. By comparison, myotube EAP activity can be observed in the wing regions (red points) as well as the central regions (green points) (FIG. 27(D)).

Feasibility of Detecting Information Transmission from a Neuronal Population to a Myotube Population in Structured Cocultures The neural interfaces described herein (the embodiment myo-MEAs) provide a design that can build on the success of EMG-based and PNS-based approaches. Various embodiment designs are a modification of the traditional cultured probe concept using microscale grooves into which myotubes are cultured, directing interaction of myotubes with specific electrode sites and preserving myotube independence from one another to increase the number of independent signals available per unit surface area. These myotubes are coupled to regenerated motoneuron axons at the NMJ, contracting in response to the extracellular action potentials (EAPs) they transmit, so the embodiment myo-MEA records myotube activity as a proxy for recording from the axonal EAP directly.

This approach to recording motor intent takes advantage of the larger extracellular voltage changes caused by depolarization of muscle cells relative to axons without sacrificing the high degree of cellular specificity available with implantable microscale MEAS. Using myotubes in this capacity represents a shift from current designs, which aim to record directly from neuronal sources on a microscale or from muscle tissue on a macroscale. Such a cultured probe approach to neural interfacing entailing the use of muscle cells is novel. Similarly, the use of topographical cues to effect myotube independence is a unique aspect unconsidered in the prior art.

Figure 28:
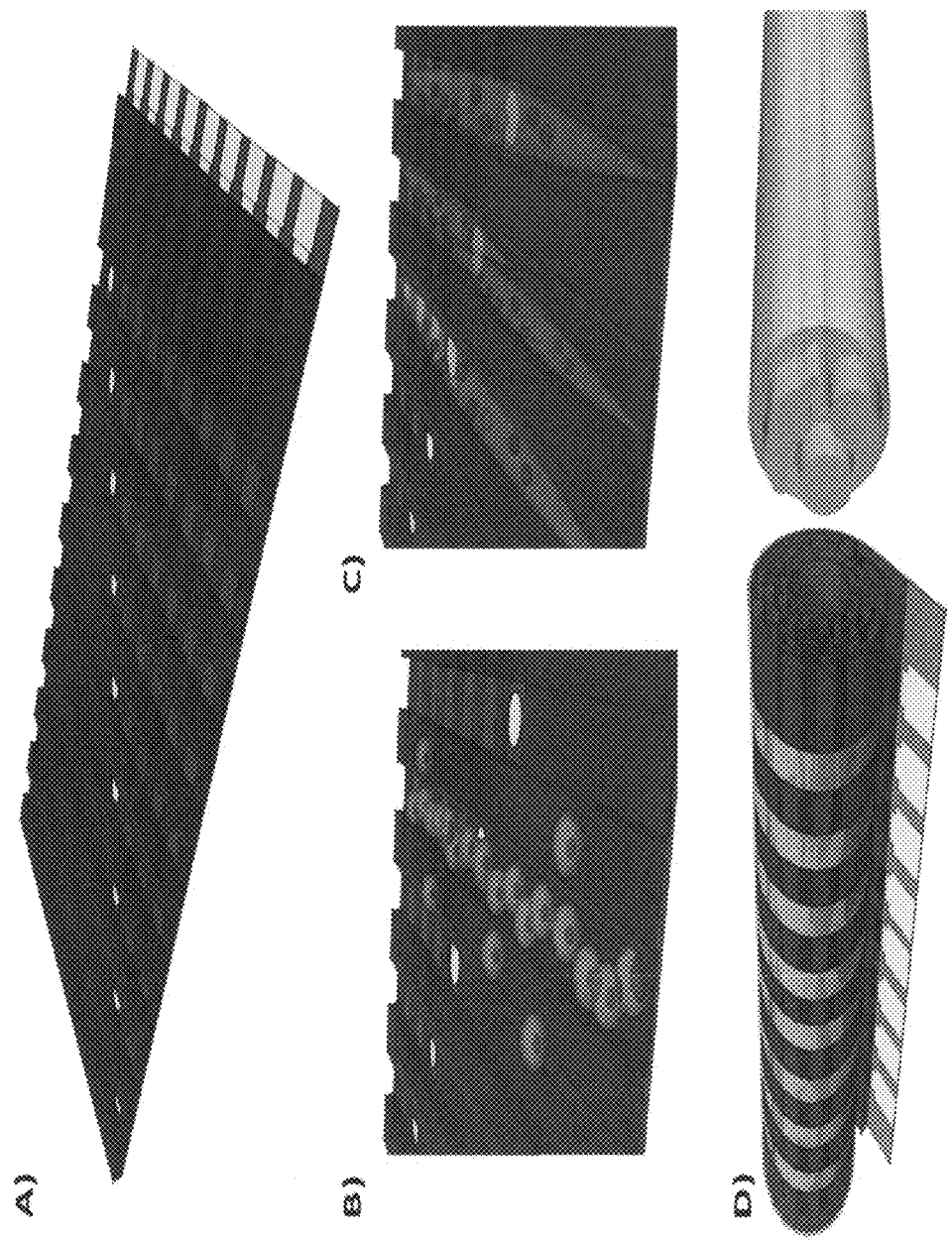
FIG. 28 illustrates another embodiment myo-MEA device and related fabrication method.

Other embodiment devices are possible. For example, in one embodiment, as illustrated in FIG. 28, myotubes are cutured on a flexible electrode array that employs microscale grooves (FIG. 28(A)) to accomplish: 1) directing the formation of myotubes to specific electrode sites, and 2) preserving myotube independence from one another, as discussed earlier. Once the myotubes have formed and settled to electrode sites (FIG. 28(B-C)), the flexible array is rolled into a cylinder (FIG. 28(D)), trapping the myotubes in the resulting channels, and putting the embodiment device in a conformation ready for implantation as a three dimensional peripheral nerve endcap. After attachment to the severed end of a peripheral nerve, motor axons are encouraged to grow into the construct by the indwelling myotubes where they would synapse, forming functional neuromuscular junctions. Action potentials carried along these regenerated motor axons arrive at the myotubes, causing excitation and contraction, and generating a microscopic EMG signal for each activated cell. These EMG signals therefore contain an encoded version of the motor intention carried along the peripheral nerve, which may be decoded in a similar fashion to the decoding involved in the TMR technique by way of corresponding electrode sites, as discussed at length earlier.

FIG. 29 illustrates another embodiment device. FIG. 29(A) is a 3D view of the assembled embodiment myo-MEA. The device has electrodes (preferably gold) patterned onto glass and covered by an insulating layer of PDMS photoresist except at contacts and electrodes in such a way to interface with standard MEA recording equipment. A PDMS ring creates a well in which cells can be cultured (see inlay for cross sectional view). FIG. 29(B) is an expanded view of the red boxed area in FIG. 29(A), showing the co-culture area and electrode wiring routes. Their embodiment design includes a central octagonal area for explant culture, and two grooved wing areas (a long and short wing) for myotube culture. FIG. 29(C) is an expanded view of the red boxed area in FIG. 29(B), showing exposed electrode contacts in the octagon and grooved wing. The octagon and grooves are etched through the PDMS insulating layer, creating topographical modification. These features are, for example, 40 μm deep and are used to confine neurite outgrowth and steer myotube formation. FIG. 29(D) is a schematic view of FIG. 29(C) showing feature dimensions. FIG. 29(E) is a cross-sectional view of the embodiment myo-MEA electrode contacts in the octagon and grooved areas. Gold electrodes are patterned onto the glass substrate and covered with an insulating layer of PDMS.

Topographical features are cut into the PDMS creating the embodiment patterns and exposing electrode contacts where appropriate.

The embodiment of FIG. 29 thus includes the creation of tailored micro-environments to induce ordered myotube/SC explant co-cultures. This facilitates spatial separation of myotubes and motoneurons necessary to precisely observe circuit formation and facilitate the accurate recording of depolarization of individual myotubes.

Briefly, the fabrication process for the above embodiment runs as follows: A) Starting point is a glass slide. Photoresist (PR) is spin-coated to a depth of 1 μm. B) This layer of photoresist is exposed using standard optical lithography techniques (contact printing) with a transparency mask bearing the electrode contact and wiring features. It is then developed to selectively expose the glass substrate at the intended sites of electrode deposition. C) The chip is sputter-coated with gold to a depth of 100 nm. The remaining photoresist is then removed in a technique know as "lift-off" patterning, leaving gold deposited only in the regions indicated by the first transparency mask. D) SU8 PR is then be spin-coated to a depth of 40 μm and baked onto the surface. E) At this point a second transparency mask bearing the pattern of the central octagon and peripheral grooves is used to expose the SU8. F) The SU8 is developed, leaving the topographical features carved into the insulating layer of SU8 with the appropriate electrode contact pattern underneath the entire structure. In some embodiments the SU8 may be replaced with a photopaternable polydimethylsiloxane (PDMS). In other embodiments electrodes meant for neuronal contact can be platinized with platinum black using an electroplating procedure to reduce electrode impedance.

Eventual clinical adaptation of the embodiment myo-MEA devices would bring with it the following benefits: 1) selective regeneration of motor axons onto myotubes provides signals encoding primarily motor intention and largely excludes the sensory information and cognitive information carried by neurons that would not form NMJs with the myotubes, 2) robust growth of myotubes and adhesion to the MEA surface relative to PNS axons provides a more stable long-term recording platform, and 3) the neurotrophic activity of myotubes provides cues directing axonal ingrowth. It is our hope that by creating a neural interface based on a large array of isolated myotubes innervated by regenerated motor axons, clinical adaptations of the myo-MEA will be able to record a greater number of independent signals and improve the recording efficiency of the interface.

The myo-MEA is uniquely designed to take advantage of myotube properties and their interaction with the PNS to specifically target neural signals that are highly tuned to motor intention. In so doing, the design addresses the specific needs of amputees and severe PNS injury patients in a way that other neural interfaces do not and increases the chances of its clinical success in this patient base.

All publications cited in the specification, including the above, both patent publications and non-patent publications, are indicative of the level of skill of those skilled in the art to which this invention pertains. All these publications are herein fully incorporated by reference to the same extent as if each individual publication were specifically and individually indicated as being incorporated by reference.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the following claims.

What is claimed is:

1. A microelectrode array comprising a substrate, the substrate comprising
a plurality of electrical contact pads,
a plurality of grooves each comprising at least one electrode electrically connected to at least one of the electrical contact pads, and
a plurality of myotubes each disposed within a respective groove of the plurality of grooves such that it overlays the at least one electrode of the respective groove and such that it is arranged to contract independently from all other said plurality of myotubes.

2. The microelectrode array of claim 1, wherein at least one of the plurality of myotubes is attached to a peripheral nerve.

3. The microelectrode array of claim 1, further comprising a laminin layer.

4. The microelectrode array of claim 1, wherein the plurality of grooves are connected to a neural explant region on the substrate.

5. The microelectrode array of claim 1, wherein the neural explant region comprises neural tissue that couples to the plurality of myotubes.

6. A microelectrode array comprising a substrate, the substrate comprising a plurality of grooves and a plurality of electrical contact pads, the grooves each comprising at least one electrode electrically connected to at least one of the electrical contact pads, each of the grooves containing at least one myotube that overlays the at least one electrode, wherein the myotubes are independent from one another.

7. The microelectrode array of claim 6, wherein the plurality of grooves have widths that are between 30μm and 150μm.

8. The microelectrode array of claim 7, wherein the plurality of grooves have widths that are between 30μm and 70μm.

9. A microelectrode array comprising a substrate, the substrate comprising a plurality of grooves and a plurality of electrical contact pads, the grooves each comprising at least one electrode electrically connected to at least one of the electrical contact pads, each of the grooves containing at least one myotube that overlays the at least one electrode, wherein the substrate is flexible and rolled into a cylinder such that the myotubes are trapped inside resulting channels.

* * * * *